US009765121B2

(12) United States Patent
Demirel et al.

(10) Patent No.: US 9,765,121 B2
(45) Date of Patent: Sep. 19, 2017

(54) DE NOVO STRUCTURAL PROTEIN DESIGN FOR MANUFACTURING HIGH STRENGTH MATERIALS

(71) Applicant: The Penn State Research Foundation, University Park, PA (US)

(72) Inventors: Melik Demirel, State College, PA (US); Benjamin Allen, State College, PA (US); Huihun Jung, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/137,999

(22) Filed: Apr. 25, 2016

(65) Prior Publication Data

US 2016/0311866 A1 Oct. 27, 2016

Related U.S. Application Data

(60) Provisional application No. 62/152,437, filed on Apr. 24, 2015.

(51) Int. Cl.

| | |
|---|---|
| ***C07K 14/00*** | (2006.01) |
| ***C07K 14/43*** | (2006.01) |
| ***C07K 14/435*** | (2006.01) |

(52) U.S. Cl.

CPC ........ *C07K 14/00* (2013.01); *C07K 14/43504* (2013.01)

(58) Field of Classification Search

None

See application file for complete search history.

(56) References Cited

U.S. PATENT DOCUMENTS

| | | | |
|---|---|---|---|
| 7,288,391 | B2 | 10/2007 | Roth et al. |
| 7,521,228 | B2 | 4/2009 | Lewis et al. |
| 7,723,109 | B2 | 5/2010 | Lewis |
| 7,745,528 | B2 | 6/2010 | Prud'Homme et al. |
| 2012/0022005 | A1 | 1/2012 | Gat et al. |

FOREIGN PATENT DOCUMENTS

| | | |
|---|---|---|
| WO | 2014062134 | 4/2014 |
| WO | 2014160131 | 10/2014 |

OTHER PUBLICATIONS

Demirel, et al., Recent Advances in Nanoscale Bioinspired Materials, Macromolecular Bioscienc, vol. 15, No. 3, pp. 300-311 Dec. 4, 2014.

Pena-Francesch, et al., Pressure Sensitive Adhesion of an Elastomeric Protein Complex Extracted From Squid Ring Teeth, Advanced Functional Materials, vol. 24, No. 39, pp. 6227-6233 Aug. 11, 2014.

Pena-Francesch, et al., Materials Fabrication from Native and Recombinant Thermoplastic Squid Proteins, Advanced Functional Materials, vol. 24, No. 47, pp. 7401-7409 Sep. 11, 2014.

Guerette, et al., Accelerating the design of biomimetic materials by integrating RNA-seq with proteomics and materials science, Nature Biotechnology, vol. 31, No. 10, 11 pages Sep. 8, 2013.

*Primary Examiner* — Suzanne M Noakes

*Assistant Examiner* — Jae W Lee

(74) *Attorney, Agent, or Firm* — Hodgson Russ LLP

(57) ABSTRACT

Provided is a supramolecular polypeptide comprising alternating repeats of crystallite-forming subsequences and amorphous subsequences. The crystallite-forming subsequences form crystallites comprising stacks of one or more β-sheets and the amorphous subsequences form a network of hydrogen bonds. The supramolecular polypeptides are capable of exhibiting self-healing behavior.

8 Claims, 7 Drawing Sheets

SEQUENCE LISTING

```
<160> NUMBER OF SEQ ID NOS: 304

<210> SEQ ID NO 1
<211> LENGTH: 15
<212> TYPE: PRT
<213> ORGANISM: Loligo vulgaris

<400> SEQUENCE: 1

Tyr Tyr Arg Lys Ser Val Ser Thr Val Ser His Gly Ala His Tyr
1               5                   10                  15


<210> SEQ ID NO 2
<211> LENGTH: 14
<212> TYPE: PRT
<213> ORGANISM: Loligo vulgaris
```

<400> SEQUENCE: 2

```
Val Ser Ser Ser Val Ser His Val Ser His Gly Ala His Tyr
1               5                   10
```

<210> SEQ ID NO 3
<211> LENGTH: 14
<212> TYPE: PRT
<213> ORGANISM: Loligo vulgaris

<400> SEQUENCE: 3

```
Ala Ala Thr Ala Val Ser His Thr Thr His Gly Ile His His
1               5                   10
```

<210> SEQ ID NO 4
<211> LENGTH: 9
<212> TYPE: PRT
<213> ORGANISM: Loligo vulgaris

<400> SEQUENCE: 4

```
Ala Ala Thr Thr Ala Val Thr His His
1               5
```

<210> SEQ ID NO 5
<211> LENGTH: 12
<212> TYPE: PRT
<213> ORGANISM: Loligo vulgaris

<400> SEQUENCE: 5

```
His Val Gly Thr Ser Val His Ser Val Ser His Gly
1               5                   10
```

<210> SEQ ID NO 6
<211> LENGTH: 13
<212> TYPE: PRT
<213> ORGANISM: Loligo vulgaris

<400> SEQUENCE: 6

```
His Val Gly Thr Ser Val His Ser Val Ser His Gly Val
1               5                   10
```

<210> SEQ ID NO 7
<211> LENGTH: 9
<212> TYPE: PRT
<213> ORGANISM: Loligo vulgaris

<400> SEQUENCE: 7

```
Val Thr Ser Ala Val His Thr Val Ser
1               5
```

<210> SEQ ID NO 8
<211> LENGTH: 11
<212> TYPE: PRT
<213> ORGANISM: Loligo vulgaris

<400> SEQUENCE: 8

```
Ala Ala Thr Thr Ala Val Thr Gln Thr His His
1               5                   10
```

<210> SEQ ID NO 9
<211> LENGTH: 9
<212> TYPE: PRT
<213> ORGANISM: Loligo vulgaris

<400> SEQUENCE: 9

```
Ala Ala Thr Thr Ala Val Thr His His
1               5


<210> SEQ ID NO 10
<211> LENGTH: 12
<212> TYPE: PRT
<213> ORGANISM: Loligo vulgaris

<400> SEQUENCE: 10

Ala Ala Thr Ala Val Ser His Thr Thr His His Ala
1               5                   10


<210> SEQ ID NO 11
<211> LENGTH: 15
<212> TYPE: PRT
<213> ORGANISM: Loligo vulgaris

<400> SEQUENCE: 11

Ala Val Ser Thr Val Ser His Gly Leu Gly Tyr Gly Leu His His
1               5                   10                  15


<210> SEQ ID NO 12
<211> LENGTH: 10
<212> TYPE: PRT
<213> ORGANISM: Loligo vulgaris

<400> SEQUENCE: 12

Arg Ser Val Ser His Thr Thr His Ser Ala
1               5                   10


<210> SEQ ID NO 13
<211> LENGTH: 15
<212> TYPE: PRT
<213> ORGANISM: Loligo vulgaris

<400> SEQUENCE: 13

Tyr Tyr Arg Arg Ser Phe Ser Thr Val Ser His Gly Ala His Tyr
1               5                   10                  15


<210> SEQ ID NO 14
<211> LENGTH: 13
<212> TYPE: PRT
<213> ORGANISM: Loligo vulgaris

<400> SEQUENCE: 14

Val Ser Ser Val Arg Thr Val Ser His Gly Leu His His
1               5                   10


<210> SEQ ID NO 15
<211> LENGTH: 11
<212> TYPE: PRT
<213> ORGANISM: Loligo vulgaris

<400> SEQUENCE: 15

Ala Ala Thr Ala Val Ser His Thr Thr His His
1               5                   10


<210> SEQ ID NO 16
<211> LENGTH: 10
<212> TYPE: DNA
<213> ORGANISM: Loligo vulgaris

<400> SEQUENCE: 16

vgaavstvhh                                                            10
```

<210> SEQ ID NO 17
<211> LENGTH: 10
<212> TYPE: PRT
<213> ORGANISM: Loligo vulgaris

<400> SEQUENCE: 17

Ala Ala Thr Ala Val Ser His Asn Ser Ser
1 5 10

<210> SEQ ID NO 18
<211> LENGTH: 15
<212> TYPE: PRT
<213> ORGANISM: Loligo vulgaris

<400> SEQUENCE: 18

Tyr Ile Gly Arg Ser Val Ser Thr Val Ser His Gly Ser His Tyr
1 5 10 15

<210> SEQ ID NO 19
<211> LENGTH: 14
<212> TYPE: DNA
<213> ORGANISM: Loligo vulgaris

<400> SEQUENCE: 19
msssvshvsh tahs 14

<210> SEQ ID NO 20
<211> LENGTH: 9
<212> TYPE: PRT
<213> ORGANISM: Loligo vulgaris

<400> SEQUENCE: 20

Val Val Ser His Val Thr His Thr Ile
1 5

<210> SEQ ID NO 21
<211> LENGTH: 14
<212> TYPE: PRT
<213> ORGANISM: Loligo vulgaris

<400> SEQUENCE: 21

Val Gly Ala Ser Val Ser Thr Val Ser His Gly Ile Gly His
1 5 10

<210> SEQ ID NO 22
<211> LENGTH: 14
<212> TYPE: PRT
<213> ORGANISM: Loligo vulgaris

<400> SEQUENCE: 22

Val Gly Gln Ser Val Ser Thr Val Ser His Gly Val His Ala
1 5 10

<210> SEQ ID NO 23
<211> LENGTH: 12
<212> TYPE: PRT
<213> ORGANISM: Loligo vulgaris

<400> SEQUENCE: 23

Thr Gly Ser Ser Ile Ser Thr Val Ser His Gly Val
1 5 10

<210> SEQ ID NO 24
<211> LENGTH: 10

<212> TYPE: PRT
<213> ORGANISM: Loligo vulgaris

<400> SEQUENCE: 24

Val Gly Ala Ala Val Ser Thr Val His His
1 5 10

<210> SEQ ID NO 25
<211> LENGTH: 11
<212> TYPE: PRT
<213> ORGANISM: Loligo vulgaris

<400> SEQUENCE: 25

Ala Ala Thr Ala Val Ser His Thr Thr His His
1 5 10

<210> SEQ ID NO 26
<211> LENGTH: 11
<212> TYPE: PRT
<213> ORGANISM: Loligo vulgaris

<400> SEQUENCE: 26

Gly Ala Ala Ala Tyr Ser His Thr Val His His
1 5 10

<210> SEQ ID NO 27
<211> LENGTH: 11
<212> TYPE: PRT
<213> ORGANISM: Loligo vulgaris

<400> SEQUENCE: 27

Ala Ala Thr Thr Tyr Arg Gln Thr Thr His His
1 5 10

<210> SEQ ID NO 28
<211> LENGTH: 12
<212> TYPE: PRT
<213> ORGANISM: Loligo vulgaris

<400> SEQUENCE: 28

Ala Ala Thr Ala Val Ser His Thr Thr His His Ala
1 5 10

<210> SEQ ID NO 29
<211> LENGTH: 10
<212> TYPE: PRT
<213> ORGANISM: Loligo vulgaris

<400> SEQUENCE: 29

Ala Ala Ala Ser Val Ser Thr Val His His
1 5 10

<210> SEQ ID NO 30
<211> LENGTH: 12
<212> TYPE: PRT
<213> ORGANISM: Loligo vulgaris

<400> SEQUENCE: 30

Ala Ala Thr Ala Val Ser His Thr Thr His His Ala
1 5 10

<210> SEQ ID NO 31
<211> LENGTH: 15
<212> TYPE: PRT
<213> ORGANISM: Loligo vulgaris

<400> SEQUENCE: 31

Ala Val Ser Thr Val Ser His Gly Leu Gly Tyr Gly Leu His His
1 5 10 15

<210> SEQ ID NO 32
<211> LENGTH: 11
<212> TYPE: PRT
<213> ORGANISM: Loligo vulgaris

<400> SEQUENCE: 32

Ala Thr Ala Val Ser His Thr Thr His His Ala
1 5 10

<210> SEQ ID NO 33
<211> LENGTH: 15
<212> TYPE: PRT
<213> ORGANISM: Loligo vulgaris

<400> SEQUENCE: 33

Tyr Ile Gly Arg Ser Val Ser Thr Val Ser His Gly Ser His Tyr
1 5 10 15

<210> SEQ ID NO 34
<211> LENGTH: 14
<212> TYPE: PRT
<213> ORGANISM: Loligo vulgaris

<400> SEQUENCE: 34

Met Ser Ser Ser Val Ser His Val Ser His Thr Ala His Ser
1 5 10

<210> SEQ ID NO 35
<211> LENGTH: 9
<212> TYPE: PRT
<213> ORGANISM: Loligo vulgaris

<400> SEQUENCE: 35

Val Val Ser His Val Thr His Thr Ile
1 5

<210> SEQ ID NO 36
<211> LENGTH: 15
<212> TYPE: PRT
<213> ORGANISM: Loligo vulgaris

<400> SEQUENCE: 36

Thr Gly Ala Ser Val Asn Thr Val Ser His Gly Ile Ser His Ala
1 5 10 15

<210> SEQ ID NO 37
<211> LENGTH: 12
<212> TYPE: PRT
<213> ORGANISM: Loligo vulgaris

<400> SEQUENCE: 37

Ala Ser Thr Ser Val Ser His Thr Thr His Ser Val
1 5 10

<210> SEQ ID NO 38
<211> LENGTH: 14
<212> TYPE: PRT
<213> ORGANISM: Loligo vulgaris

<400> SEQUENCE: 38

Val Gly Ala Ser Val Ser Thr Val Ser His Gly Ile Gly His
1 5 10

<210> SEQ ID NO 39
<211> LENGTH: 9
<212> TYPE: PRT
<213> ORGANISM: Loligo vulgaris

<400> SEQUENCE: 39

His Thr Val Ser His Val Ser His Gly
1 5

<210> SEQ ID NO 40
<211> LENGTH: 13
<212> TYPE: PRT
<213> ORGANISM: Loligo vulgaris

<400> SEQUENCE: 40

Val Ala His His Gly Thr Ile Ser Arg Arg Tyr Ala Ile
1 5 10

<210> SEQ ID NO 41
<211> LENGTH: 13
<212> TYPE: PRT
<213> ORGANISM: Loligo vulgaris

<400> SEQUENCE: 41

Val Thr His Tyr Ser His Val Ser His Asp Val His Gln
1 5 10

<210> SEQ ID NO 42
<211> LENGTH: 11
<212> TYPE: PRT
<213> ORGANISM: Loligo vulgaris

<400> SEQUENCE: 42

Ala Val Gly His Thr Thr Val Thr His Ala Val
1 5 10

<210> SEQ ID NO 43
<211> LENGTH: 13
<212> TYPE: PRT
<213> ORGANISM: Loligo vulgaris

<400> SEQUENCE: 43

Ala Ala Thr Ser Val Lys Thr Val Ser His Gly Phe His
1 5 10

<210> SEQ ID NO 44
<211> LENGTH: 14
<212> TYPE: PRT
<213> ORGANISM: Loligo vulgaris

<400> SEQUENCE: 44

Val Gly Ser Thr Ile Ser His Thr Thr His Gly Val His His
1 5 10

<210> SEQ ID NO 45
<211> LENGTH: 14
<212> TYPE: PRT
<213> ORGANISM: Loligo vulgaris

<400> SEQUENCE: 45

Ala Ala Thr Ser Val Ser His Thr Thr His Gly Val His His

```
1               5                   10


<210> SEQ ID NO 46
<211> LENGTH: 14
<212> TYPE: PRT
<213> ORGANISM: Loligo vulgaris

<400> SEQUENCE: 46

Ala Ala Ser Ser Val Thr His Thr Thr His Gly Val Ala His
1               5                   10


<210> SEQ ID NO 47
<211> LENGTH: 17
<212> TYPE: PRT
<213> ORGANISM: Euprymna scolopes

<400> SEQUENCE: 47

Gly Leu Leu Gly Ala Ala Ala Thr Thr Tyr Lys His Thr Thr His His
1               5                   10                  15

Ala


<210> SEQ ID NO 48
<211> LENGTH: 12
<212> TYPE: PRT
<213> ORGANISM: Euprymna scolopes

<400> SEQUENCE: 48

Ala Ala Thr Thr Tyr Ser His Thr Ala His His Ala
1               5                   10


<210> SEQ ID NO 49
<211> LENGTH: 11
<212> TYPE: PRT
<213> ORGANISM: Euprymna scolopes

<400> SEQUENCE: 49

Ala Ala Ala Ser Thr Val Ser Thr Val His His
1               5                   10


<210> SEQ ID NO 50
<211> LENGTH: 11
<212> TYPE: PRT
<213> ORGANISM: Euprymna scolopes

<400> SEQUENCE: 50

Ala Ala Thr Tyr Ser His Thr Thr His His Ala
1               5                   10


<210> SEQ ID NO 51
<211> LENGTH: 10
<212> TYPE: PRT
<213> ORGANISM: Euprymna scolopes

<400> SEQUENCE: 51

Ala Ala Ala Ser Val Ser Thr Ala His His
1               5                   10


<210> SEQ ID NO 52
<211> LENGTH: 11
<212> TYPE: PRT
<213> ORGANISM: Euprymna scolopes

<400> SEQUENCE: 52

Ala Ala Thr Ser Tyr Ser His Ala Leu His His
```

1 5 10

<210> SEQ ID NO 53
<211> LENGTH: 17
<212> TYPE: PRT
<213> ORGANISM: Euprymna scolopes

<400> SEQUENCE: 53

Gly Leu Leu Gly Ala Ala Ala Thr Thr Tyr Lys His Thr Thr His His
1 5 10 15

Ala

<210> SEQ ID NO 54
<211> LENGTH: 12
<212> TYPE: PRT
<213> ORGANISM: Euprymna scolopes

<400> SEQUENCE: 54

Ala Ala Thr Thr Tyr Ser His Thr Ala His His Ala
1 5 10

<210> SEQ ID NO 55
<211> LENGTH: 11
<212> TYPE: PRT
<213> ORGANISM: Euprymna scolopes

<400> SEQUENCE: 55

Ala Ala Ala Ser Thr Val Ser Thr Val His His
1 5 10

<210> SEQ ID NO 56
<211> LENGTH: 11
<212> TYPE: PRT
<213> ORGANISM: Euprymna scolopes

<400> SEQUENCE: 56

Ala Ala Thr Tyr Ser His Thr Thr His His Ala
1 5 10

<210> SEQ ID NO 57
<211> LENGTH: 11
<212> TYPE: DNA
<213> ORGANISM: Euprymna scolopes

<400> SEQUENCE: 57
aaaasvstvh h 11

<210> SEQ ID NO 58
<211> LENGTH: 12
<212> TYPE: PRT
<213> ORGANISM: Euprymna scolopes

<400> SEQUENCE: 58

Ala Ala Thr Ser Phe Ser His Thr Ala His His Ala
1 5 10

<210> SEQ ID NO 59
<211> LENGTH: 11
<212> TYPE: PRT
<213> ORGANISM: Euprymna scolopes

<400> SEQUENCE: 59

Ala Ala Ala Ser Thr Val Ser Thr Val His His
1 5 10

<210> SEQ ID NO 60
<211> LENGTH: 11
<212> TYPE: PRT
<213> ORGANISM: Euprymna scolopes

<400> SEQUENCE: 60

```
Ala Ala Thr Tyr Ser His Thr Thr His His Ala
1               5                   10
```

<210> SEQ ID NO 61
<211> LENGTH: 9
<212> TYPE: PRT
<213> ORGANISM: Loligo Palei

<400> SEQUENCE: 61

```
Ser Val Ala Thr Arg Arg Val Val Tyr
1               5
```

<210> SEQ ID NO 62
<211> LENGTH: 9
<212> TYPE: PRT
<213> ORGANISM: Loligo Palei

<400> SEQUENCE: 62

```
Ala Val Ser His Val Thr His Thr Ile
1               5
```

<210> SEQ ID NO 63
<211> LENGTH: 12
<212> TYPE: PRT
<213> ORGANISM: Loligo Palei

<400> SEQUENCE: 63

```
Ala Ala Thr Ser Val Ser His Thr Thr His Ser Val
1               5                   10
```

<210> SEQ ID NO 64
<211> LENGTH: 14
<212> TYPE: PRT
<213> ORGANISM: Loligo Palei

<400> SEQUENCE: 64

```
Val Gly Ala Ser Val Ser Thr Val Ser His Gly Val His Ala
1               5                   10
```

<210> SEQ ID NO 65
<211> LENGTH: 15
<212> TYPE: PRT
<213> ORGANISM: Loligo Palei

<400> SEQUENCE: 65

```
Val Ile His Gly Gly Ala Thr Leu Ser Thr Val Ser His Gly Val
1               5                   10                  15
```

<210> SEQ ID NO 66
<211> LENGTH: 12
<212> TYPE: PRT
<213> ORGANISM: Loligo Palei

<400> SEQUENCE: 66

```
Thr Gly Thr Ser Val Ser Thr Val Ser His Gly Val
1               5                   10
```

<210> SEQ ID NO 67
<211> LENGTH: 10
<212> TYPE: PRT
<213> ORGANISM: Loligo Palei

<400> SEQUENCE: 67

His Ser Val Ser Thr Val Ser His Gly Ala
1 5 10

<210> SEQ ID NO 68
<211> LENGTH: 14
<212> TYPE: PRT
<213> ORGANISM: Loligo Palei

<400> SEQUENCE: 68

Ala Gly Ser Ser Ile Ser Thr Val Ser His Gly Val His Ala
1 5 10

<210> SEQ ID NO 69
<211> LENGTH: 14
<212> TYPE: PRT
<213> ORGANISM: Loligo Palei

<400> SEQUENCE: 69

Thr Gly Ser Ser Ile Ser Thr Val Ser His Gly Val His Ser
1 5 10

<210> SEQ ID NO 70
<211> LENGTH: 13
<212> TYPE: PRT
<213> ORGANISM: Loligo Palei

<400> SEQUENCE: 70

His Ile Gly Thr Ser Val Ser Ser Val Ser His Gly Ala
1 5 10

<210> SEQ ID NO 71
<211> LENGTH: 13
<212> TYPE: PRT
<213> ORGANISM: Loligo Palei

<400> SEQUENCE: 71

His Val Gly Thr Ser Val His Ser Val Ser His Gly Val
1 5 10

<210> SEQ ID NO 72
<211> LENGTH: 11
<212> TYPE: PRT
<213> ORGANISM: Loligo Palei

<400> SEQUENCE: 72

His Ala Ser Thr Thr Thr His Ser Ile Gly Leu
1 5 10

<210> SEQ ID NO 73
<211> LENGTH: 9
<212> TYPE: PRT
<213> ORGANISM: Loligo Palei

<400> SEQUENCE: 73

His Ser Val Ser His Val Ser His Gly
1 5

<210> SEQ ID NO 74
<211> LENGTH: 13

<212> TYPE: PRT
<213> ORGANISM: Loligo Palei

<400> SEQUENCE: 74

Val Ala His His Gly Thr Ile Ser Arg Arg Tyr Ala Ile
1 5 10

<210> SEQ ID NO 75
<211> LENGTH: 9
<212> TYPE: PRT
<213> ORGANISM: Loligo Palei

<400> SEQUENCE: 75

His Ser Val Ser His Val Ser His Gly
1 5

<210> SEQ ID NO 76
<211> LENGTH: 13
<212> TYPE: PRT
<213> ORGANISM: Loligo Palei

<400> SEQUENCE: 76

Val Ala His His Gly Thr Ile Ser Arg Arg Tyr Ala Ile
1 5 10

<210> SEQ ID NO 77
<211> LENGTH: 14
<212> TYPE: PRT
<213> ORGANISM: Loligo Palei

<400> SEQUENCE: 77

Ser His Gly Val Ser His Thr Ala Gly Tyr Ser Ser His Tyr
1 5 10

<210> SEQ ID NO 78
<211> LENGTH: 10
<212> TYPE: PRT
<213> ORGANISM: Loligo Palei

<400> SEQUENCE: 78

Gly His Ala Val Thr His Thr Val His His
1 5 10

<210> SEQ ID NO 79
<211> LENGTH: 14
<212> TYPE: PRT
<213> ORGANISM: Loligo Palei

<400> SEQUENCE: 79

Ser Ala Gly Gly Thr Thr Val Ser His Ser Thr His Gly Val
1 5 10

<210> SEQ ID NO 80
<211> LENGTH: 11
<212> TYPE: PRT
<213> ORGANISM: Loligo Palei

<400> SEQUENCE: 80

Ala Val Ser His Val Thr His Thr Ile His Ala
1 5 10

<210> SEQ ID NO 81
<211> LENGTH: 11
<212> TYPE: PRT
<213> ORGANISM: Loligo Palei

<400> SEQUENCE: 81

His Ala Val Ser Thr Val Ala His Gly Ile His
1 5 10

<210> SEQ ID NO 82
<211> LENGTH: 12
<212> TYPE: PRT
<213> ORGANISM: Loligo Palei

<400> SEQUENCE: 82

Ala Ala Thr Ser Val Ser His Thr Thr His Ser Val
1 5 10

<210> SEQ ID NO 83
<211> LENGTH: 11
<212> TYPE: DNA
<213> ORGANISM: Loligo Palei

<400> SEQUENCE: 83
avrhttvtha v 11

<210> SEQ ID NO 84
<211> LENGTH: 13
<212> TYPE: PRT
<213> ORGANISM: Loligo Palei

<400> SEQUENCE: 84

Ala Ala Thr Ser Val Lys Thr Val Ser His Gly Tyr His
1 5 10

<210> SEQ ID NO 85
<211> LENGTH: 15
<212> TYPE: PRT
<213> ORGANISM: Loligo Palei

<400> SEQUENCE: 85

Val Gly Ser Thr Ser Val Ser His Thr Thr His Gly Val His His
1 5 10 15

<210> SEQ ID NO 86
<211> LENGTH: 14
<212> TYPE: PRT
<213> ORGANISM: Loligo Palei

<400> SEQUENCE: 86

Ala Ala Thr Thr Val Ser His Thr Thr His Gly Ala His His
1 5 10

<210> SEQ ID NO 87
<211> LENGTH: 14
<212> TYPE: PRT
<213> ORGANISM: Loligo Palei

<400> SEQUENCE: 87

Ala Ala Ser Ser Val Thr His Thr Thr His Gly Val Ala His
1 5 10

<210> SEQ ID NO 88
<211> LENGTH: 17
<212> TYPE: PRT
<213> ORGANISM: Loligo Palei

<400> SEQUENCE: 88

Ser Ser Tyr Tyr Gly Arg Ser Ala Ser Thr Val Ser His Gly Thr His
1 5 10 15

Tyr

<210> SEQ ID NO 89
<211> LENGTH: 12
<212> TYPE: PRT
<213> ORGANISM: Loligo Palei

<400> SEQUENCE: 89

Thr Ser Val Ser Gln Val Ser His Thr Ala His Ser
1 5 10

<210> SEQ ID NO 90
<211> LENGTH: 10
<212> TYPE: PRT
<213> ORGANISM: Loligo Palei

<400> SEQUENCE: 90

Val Arg Tyr His Gly Tyr Ser Ile Gly His
1 5 10

<210> SEQ ID NO 91
<211> LENGTH: 11
<212> TYPE: PRT
<213> ORGANISM: Loligo Palei

<400> SEQUENCE: 91

Ala Val Ser His Val Thr His Thr Ile His Ala
1 5 10

<210> SEQ ID NO 92
<211> LENGTH: 12
<212> TYPE: PRT
<213> ORGANISM: Loligo Palei

<400> SEQUENCE: 92

Ala Ala Thr Ser Val Ser His Thr Thr His Ser Val
1 5 10

<210> SEQ ID NO 93
<211> LENGTH: 14
<212> TYPE: PRT
<213> ORGANISM: Loligo Palei

<400> SEQUENCE: 93

Val Gly Ala Ser Val Ser Thr Val Ser His Gly Val His Ala
1 5 10

<210> SEQ ID NO 94
<211> LENGTH: 12
<212> TYPE: PRT
<213> ORGANISM: Loligo Palei

<400> SEQUENCE: 94

Thr Gly Thr Ser Val Ser Thr Val Ser His Gly Val
1 5 10

<210> SEQ ID NO 95
<211> LENGTH: 12
<212> TYPE: PRT
<213> ORGANISM: Loligo Palei

<400> SEQUENCE: 95

```
Thr Gly Ala Ser Val Ser Thr Val Ser His Gly Leu
1               5                   10


<210> SEQ ID NO 96
<211> LENGTH: 14
<212> TYPE: PRT
<213> ORGANISM: Loligo Palei

<400> SEQUENCE: 96

Ala Gly Ser Ser Ile Ser Thr Val Ser His Gly Val His Ala
1               5                   10


<210> SEQ ID NO 97
<211> LENGTH: 14
<212> TYPE: PRT
<213> ORGANISM: Loligo Palei

<400> SEQUENCE: 97

Ala Thr Ala Ser Val Ser His Thr Thr His Gly Val His His
1               5                   10


<210> SEQ ID NO 98
<211> LENGTH: 12
<212> TYPE: PRT
<213> ORGANISM: Loligo Palei

<400> SEQUENCE: 98

Ala Ala Thr Thr Val Ser His Ser Thr His Ala Val
1               5                   10


<210> SEQ ID NO 99
<211> LENGTH: 12
<212> TYPE: PRT
<213> ORGANISM: Loligo Palei

<400> SEQUENCE: 99

Ala Ala Thr Thr Val Ser His Ser Thr His Ala Val
1               5                   10


<210> SEQ ID NO 100
<211> LENGTH: 12
<212> TYPE: PRT
<213> ORGANISM: Loligo Palei

<400> SEQUENCE: 100

Gly Ala Thr Thr Tyr Ser His Thr Thr His Ala Val
1               5                   10


<210> SEQ ID NO 101
<211> LENGTH: 9
<212> TYPE: PRT
<213> ORGANISM: Loligo Palei

<400> SEQUENCE: 101

Ala Val Ser His Val Thr His Thr Ile
1               5


<210> SEQ ID NO 102
<211> LENGTH: 12
<212> TYPE: PRT
<213> ORGANISM: Loligo Palei

<400> SEQUENCE: 102

Ala Ala Thr Ser Val Ser His Thr Thr His Ser Val
1               5                   10
```

<210> SEQ ID NO 103
<211> LENGTH: 20
<212> TYPE: PRT
<213> ORGANISM: Loligo Palei

<400> SEQUENCE: 103

```
Val Ile His Gly Gly Ala Thr Leu Ser Thr Val Ser His Gly Val Ser
1               5                   10                  15

Glu Gln Ile Asp
            20
```

<210> SEQ ID NO 104
<211> LENGTH: 14
<212> TYPE: PRT
<213> ORGANISM: Loligo Palei

<400> SEQUENCE: 104

```
Ala Gly Ser Ser Ile Ser Thr Val Ser His Gly Val His Ala
1               5                   10
```

<210> SEQ ID NO 105
<211> LENGTH: 10
<212> TYPE: PRT
<213> ORGANISM: Loligo Palei

<400> SEQUENCE: 105

```
Gly His Ala Val Thr His Thr Val His His
1               5                   10
```

<210> SEQ ID NO 106
<211> LENGTH: 14
<212> TYPE: PRT
<213> ORGANISM: Loligo Palei

<400> SEQUENCE: 106

```
Ser Ala Gly Gly Thr Thr Val Ser His Ser Thr His Gly Val
1               5                   10
```

<210> SEQ ID NO 107
<211> LENGTH: 11
<212> TYPE: PRT
<213> ORGANISM: Loligo Palei

<400> SEQUENCE: 107

```
Ala Val Arg His Thr Thr Val Thr His Ala Val
1               5                   10
```

<210> SEQ ID NO 108
<211> LENGTH: 13
<212> TYPE: PRT
<213> ORGANISM: Loligo Palei

<400> SEQUENCE: 108

```
Ala Ala Thr Ser Val Lys Thr Val Ser His Gly Tyr His
1               5                   10
```

<210> SEQ ID NO 109
<211> LENGTH: 15
<212> TYPE: PRT
<213> ORGANISM: Loligo Palei

<400> SEQUENCE: 109

```
Val Gly Ser Thr Ser Val Ser His Thr Thr His Gly Val His His
```

1 5 10 15

<210> SEQ ID NO 110
<211> LENGTH: 6
<212> TYPE: PRT
<213> ORGANISM: Loligo Palei

<400> SEQUENCE: 110

Gly Ala Ala Phe His Tyr
1 5

<210> SEQ ID NO 111
<211> LENGTH: 14
<212> TYPE: PRT
<213> ORGANISM: Loligo Palei

<400> SEQUENCE: 111

Ala Ala Thr Thr Val Ser His Thr Thr His Gly Ala His His
1 5 10

<210> SEQ ID NO 112
<211> LENGTH: 14
<212> TYPE: PRT
<213> ORGANISM: Loligo Palei

<400> SEQUENCE: 112

Ala Ala Ser Ser Val Thr His Thr Thr His Gly Val Ala His
1 5 10

<210> SEQ ID NO 113
<211> LENGTH: 11
<212> TYPE: PRT
<213> ORGANISM: Loligo Palei

<400> SEQUENCE: 113

Ala Ala Ala Val Ser His Thr Thr His His Ala
1 5 10

<210> SEQ ID NO 114
<211> LENGTH: 11
<212> TYPE: PRT
<213> ORGANISM: Loligo Palei

<400> SEQUENCE: 114

Ala Ala Thr Ala Val Ser His Thr Thr His His
1 5 10

<210> SEQ ID NO 115
<211> LENGTH: 10
<212> TYPE: PRT
<213> ORGANISM: Loligo Palei

<400> SEQUENCE: 115

Val Gly Ala Ala Val Ser Thr Val His His
1 5 10

<210> SEQ ID NO 116
<211> LENGTH: 10
<212> TYPE: PRT
<213> ORGANISM: Loligo Palei

<400> SEQUENCE: 116

Val Gly Gly Ala Val Ser Thr Val His His
1 5 10

<210> SEQ ID NO 117
<211> LENGTH: 11
<212> TYPE: PRT
<213> ORGANISM: Loligo Palei

<400> SEQUENCE: 117

Gly Val Ala Ala Tyr Ser His Ser Val His His
1 5 10

<210> SEQ ID NO 118
<211> LENGTH: 13
<212> TYPE: PRT
<213> ORGANISM: Loligo Palei

<400> SEQUENCE: 118

Val Ser Ser Val Ser Thr Val Ser His Gly Leu His His
1 5 10

<210> SEQ ID NO 119
<211> LENGTH: 10
<212> TYPE: PRT
<213> ORGANISM: Loligo Palei

<400> SEQUENCE: 119

Val Gly Ala Ala Val Ser Thr Val His His
1 5 10

<210> SEQ ID NO 120
<211> LENGTH: 10
<212> TYPE: PRT
<213> ORGANISM: Loligo Palei

<400> SEQUENCE: 120

Val Gly Gly Ala Val Ser Thr Val His His
1 5 10

<210> SEQ ID NO 121
<211> LENGTH: 11
<212> TYPE: PRT
<213> ORGANISM: Loligo Palei

<400> SEQUENCE: 121

Gly Val Ala Ala Tyr Ser His Ser Val His His
1 5 10

<210> SEQ ID NO 122
<211> LENGTH: 14
<212> TYPE: PRT
<213> ORGANISM: Todarodes pacificu

<400> SEQUENCE: 122

Val Ala Ser Ser Val Ser His Thr Thr His Gly Val His His
1 5 10

<210> SEQ ID NO 123
<211> LENGTH: 12
<212> TYPE: PRT
<213> ORGANISM: Todarodes pacificu

<400> SEQUENCE: 123

Ala Ala Thr Thr Val Ser Arg Thr Thr His His Ala
1 5 10

<210> SEQ ID NO 124

<211> LENGTH: 12
<212> TYPE: PRT
<213> ORGANISM: Todarodes pacificu

<400> SEQUENCE: 124

Ala Ala Thr Ala Val Ser His Val Thr His His Ala
1 5 10

<210> SEQ ID NO 125
<211> LENGTH: 12
<212> TYPE: PRT
<213> ORGANISM: Todarodes pacificu

<400> SEQUENCE: 125

Ala Ala Thr Ser Val Ser Arg Thr Thr His His Ala
1 5 10

<210> SEQ ID NO 126
<211> LENGTH: 12
<212> TYPE: PRT
<213> ORGANISM: Todarodes pacificu

<400> SEQUENCE: 126

Ala Thr Ala Ala Val Ser His Thr Thr His His Ala
1 5 10

<210> SEQ ID NO 127
<211> LENGTH: 12
<212> TYPE: PRT
<213> ORGANISM: Todarodes pacificu

<400> SEQUENCE: 127

Ala Ala Thr Ala Val Ser His Thr Thr His His Ala
1 5 10

<210> SEQ ID NO 128
<211> LENGTH: 12
<212> TYPE: PRT
<213> ORGANISM: Todarodes pacificu

<400> SEQUENCE: 128

Ala Ala Thr Ala Val Ser His Thr Thr His His Ala
1 5 10

<210> SEQ ID NO 129
<211> LENGTH: 12
<212> TYPE: PRT
<213> ORGANISM: Todarodes pacificu

<400> SEQUENCE: 129

Ala Ala Thr Thr Val Ser Arg Thr Thr His His Ala
1 5 10

<210> SEQ ID NO 130
<211> LENGTH: 11
<212> TYPE: PRT
<213> ORGANISM: Todarodes pacificu

<400> SEQUENCE: 130

Ala Ala Ala Val Ser His Val Thr His His Ala
1 5 10

<210> SEQ ID NO 131
<211> LENGTH: 12
<212> TYPE: PRT

<213> ORGANISM: Todarodes pacificu

<400> SEQUENCE: 131

Ala Ala Thr Ser Val Ser His Thr Thr His His Ala
1 5 10

<210> SEQ ID NO 132
<211> LENGTH: 12
<212> TYPE: PRT
<213> ORGANISM: Todarodes pacificu

<400> SEQUENCE: 132

Ala Ala Thr Ala Val Ser His Thr Thr His His Ala
1 5 10

<210> SEQ ID NO 133
<211> LENGTH: 12
<212> TYPE: PRT
<213> ORGANISM: Todarodes pacificu

<400> SEQUENCE: 133

Ala Ala Thr Ala Val Ser His Thr Thr His His Ala
1 5 10

<210> SEQ ID NO 134
<211> LENGTH: 12
<212> TYPE: PRT
<213> ORGANISM: Todarodes pacificu

<400> SEQUENCE: 134

Ala Ala Thr Ser Val Ser Arg Thr Thr His His Ala
1 5 10

<210> SEQ ID NO 135
<211> LENGTH: 12
<212> TYPE: PRT
<213> ORGANISM: Todarodes pacificu

<400> SEQUENCE: 135

Ala Thr Ala Ala Val Ser His Thr Thr His His Ala
1 5 10

<210> SEQ ID NO 136
<211> LENGTH: 12
<212> TYPE: PRT
<213> ORGANISM: Todarodes pacificu

<400> SEQUENCE: 136

Ala Ala Thr Ala Val Ser His Thr Thr His His Ala
1 5 10

<210> SEQ ID NO 137
<211> LENGTH: 12
<212> TYPE: PRT
<213> ORGANISM: Todarodes pacificu

<400> SEQUENCE: 137

Ala Ala Thr Ala Val Ser His Val Thr His His Ala
1 5 10

<210> SEQ ID NO 138
<211> LENGTH: 9
<212> TYPE: PRT
<213> ORGANISM: Todarodes pacificu

<400> SEQUENCE: 138

His Thr Val Ser His Val Ser His Gly
1               5

<210> SEQ ID NO 139
<211> LENGTH: 13
<212> TYPE: PRT
<213> ORGANISM: Todarodes pacificu

<400> SEQUENCE: 139

Val Ala His His Ser Val Val Ser Arg Arg Tyr Ala Ile
1               5                   10

<210> SEQ ID NO 140
<211> LENGTH: 12
<212> TYPE: PRT
<213> ORGANISM: Todarodes pacificu

<400> SEQUENCE: 140

Ala Ala Thr Ser Val Ser His Thr Thr His His Ala
1               5                   10

<210> SEQ ID NO 141
<211> LENGTH: 12
<212> TYPE: PRT
<213> ORGANISM: Todarodes pacificu

<400> SEQUENCE: 141

Ala Ala Thr Ala Val Ser His Thr Thr His His Ala
1               5                   10

<210> SEQ ID NO 142
<211> LENGTH: 12
<212> TYPE: PRT
<213> ORGANISM: Todarodes pacificu

<400> SEQUENCE: 142

Ala Ala Thr Ala Val Ser His Thr Thr His His Ala
1               5                   10

<210> SEQ ID NO 143
<211> LENGTH: 12
<212> TYPE: PRT
<213> ORGANISM: Todarodes pacificu

<400> SEQUENCE: 143

Ala Ala Thr Ala Val Ser His Thr Thr His His Ala
1               5                   10

<210> SEQ ID NO 144
<211> LENGTH: 11
<212> TYPE: PRT
<213> ORGANISM: Todarodes pacificu

<400> SEQUENCE: 144

Ala Ala Ala Val Ser His Val Thr His His Ala
1               5                   10

<210> SEQ ID NO 145
<211> LENGTH: 11
<212> TYPE: PRT
<213> ORGANISM: Todarodes pacificu

<400> SEQUENCE: 145

Ala Ala Thr Ala Val His Thr Thr His His Ala
1 5 10

<210> SEQ ID NO 146
<211> LENGTH: 12
<212> TYPE: PRT
<213> ORGANISM: Todarodes pacificu

<400> SEQUENCE: 146

Val Gly Ala Ala Val Ser His Val Thr His His Ala
1 5 10

<210> SEQ ID NO 147
<211> LENGTH: 12
<212> TYPE: PRT
<213> ORGANISM: Todarodes pacificu

<400> SEQUENCE: 147

Val Ala Thr Ser Val Ser Arg Thr Thr His His Ala
1 5 10

<210> SEQ ID NO 148
<211> LENGTH: 12
<212> TYPE: PRT
<213> ORGANISM: Todarodes pacificu

<400> SEQUENCE: 148

Ala Ala Thr Ala Val Ser His Thr Thr His His Ala
1 5 10

<210> SEQ ID NO 149
<211> LENGTH: 10
<212> TYPE: PRT
<213> ORGANISM: Todarodes pacificu

<400> SEQUENCE: 149

Ser Ala Thr Ala Val Ser His Thr Ser His
1 5 10

<210> SEQ ID NO 150
<211> LENGTH: 11
<212> TYPE: PRT
<213> ORGANISM: Todarodes pacificu

<400> SEQUENCE: 150

Ala Ser Ser Ala Val Ser His Thr Ser His His
1 5 10

<210> SEQ ID NO 151
<211> LENGTH: 12
<212> TYPE: PRT
<213> ORGANISM: Todarodes pacificu

<400> SEQUENCE: 151

Val Ala Thr Val Thr Ser Gln Thr Ser His His Val
1 5 10

<210> SEQ ID NO 152
<211> LENGTH: 10
<212> TYPE: PRT
<213> ORGANISM: Todarodes pacificu

<400> SEQUENCE: 152

Ala Ala Ser Ala Val Ser Thr Ser Thr His
1 5 10

<210> SEQ ID NO 153
<211> LENGTH: 12
<212> TYPE: PRT
<213> ORGANISM: Todarodes pacificu

<400> SEQUENCE: 153

Val Ala Thr Ser Val Ser Arg Thr Thr His His Ala
1 5 10

<210> SEQ ID NO 154
<211> LENGTH: 12
<212> TYPE: PRT
<213> ORGANISM: Todarodes pacificu

<400> SEQUENCE: 154

Ala Ala Thr Ala Val Ser His Val Thr His His Ala
1 5 10

<210> SEQ ID NO 155
<211> LENGTH: 13
<212> TYPE: PRT
<213> ORGANISM: Todarodes pacificu

<400> SEQUENCE: 155

Val Ala His His Ser Val Val Ser Arg Arg Tyr Ala Ile
1 5 10

<210> SEQ ID NO 156
<211> LENGTH: 11
<212> TYPE: PRT
<213> ORGANISM: Todarodes pacificu

<400> SEQUENCE: 156

His Ala Val Gly Ala Val Ser Thr Leu His His
1 5 10

<210> SEQ ID NO 157
<211> LENGTH: 9
<212> TYPE: PRT
<213> ORGANISM: Todarodes pacificu

<400> SEQUENCE: 157

His Ser Val Ala Val Gly Val His His
1 5

<210> SEQ ID NO 158
<211> LENGTH: 12
<212> TYPE: PRT
<213> ORGANISM: Todarodes pacificu

<400> SEQUENCE: 158

Ala Ala Thr Ala Val Ser His Thr Thr His His Ala
1 5 10

<210> SEQ ID NO 159
<211> LENGTH: 12
<212> TYPE: PRT
<213> ORGANISM: Todarodes pacificu

<400> SEQUENCE: 159

Ala Ala Thr Ala Val Ser His Val Thr His His Ala
1 5 10

<210> SEQ ID NO 160
<211> LENGTH: 13
<212> TYPE: PRT
<213> ORGANISM: Todarodes pacificu

<400> SEQUENCE: 160

Val Ala His His Ser Val Val Ser Arg Arg Tyr Ala Ile
1 5 10

<210> SEQ ID NO 161
<211> LENGTH: 35
<212> TYPE: PRT
<213> ORGANISM: Loligo vulgaris

<400> SEQUENCE: 161

Gly Tyr Gly Leu Gly Gly Leu Tyr Gly Gly Tyr Gly Leu Gly Gly Leu
1 5 10 15

His Tyr Gly Gly Tyr Gly Leu Gly Gly Leu His Tyr Gly Gly Tyr Gly
20 25 30

Leu His Tyr
35

<210> SEQ ID NO 162
<211> LENGTH: 31
<212> TYPE: PRT
<213> ORGANISM: Loligo vulgaris

<400> SEQUENCE: 162

Gly Val Gly Gly Leu Tyr Gly Gly Tyr Gly Leu Gly Gly Leu His Gly
1 5 10 15

Gly Tyr Gly Leu Gly Gly Ile Tyr Gly Gly Tyr Gly Ala His Tyr
20 25 30

<210> SEQ ID NO 163
<211> LENGTH: 27
<212> TYPE: PRT
<213> ORGANISM: Loligo vulgaris

<400> SEQUENCE: 163

Gly Val Gly Gly Tyr Gly Met Gly Gly Leu Tyr Gly Gly Tyr Gly Leu
1 5 10 15

Gly Gly Val Tyr Gly Gly Tyr Gly Leu Gly Gly
20 25

<210> SEQ ID NO 164
<211> LENGTH: 8
<212> TYPE: PRT
<213> ORGANISM: Loligo vulgaris

<400> SEQUENCE: 164

Gly Tyr Gly Leu Gly Val Gly Leu
1 5

<210> SEQ ID NO 165
<211> LENGTH: 28
<212> TYPE: PRT
<213> ORGANISM: Loligo vulgaris

<400> SEQUENCE: 165

Leu Gly Leu Gly Tyr Gly Gly Tyr Gly Leu Gly Leu Gly Tyr Gly Leu
1 5 10 15

Gly His Gly Tyr Gly Leu Gly Leu Gly Ala Gly Ile
20 25

<210> SEQ ID NO 166
<211> LENGTH: 15
<212> TYPE: PRT
<213> ORGANISM: Loligo vulgaris

<400> SEQUENCE: 166

Gly Leu Gly Leu Gly Tyr Gly Tyr Gly Leu Gly His Gly Leu Gly
1 5 10 15

<210> SEQ ID NO 167
<211> LENGTH: 12
<212> TYPE: PRT
<213> ORGANISM: Loligo vulgaris

<400> SEQUENCE: 167

Gly Leu Gly Leu Gly Tyr Gly Leu Gly Leu Gly Leu
1 5 10

<210> SEQ ID NO 168
<211> LENGTH: 30
<212> TYPE: PRT
<213> ORGANISM: Loligo vulgaris

<400> SEQUENCE: 168

Met Gly Gly Leu Tyr Gly Gly Tyr Gly Leu Gly Gly Val Tyr Gly Gly
1 5 10 15

Tyr Gly Leu Gly Gly Ile Tyr Gly Gly Tyr Gly Ala His Tyr
20 25 30

<210> SEQ ID NO 169
<211> LENGTH: 40
<212> TYPE: PRT
<213> ORGANISM: Loligo vulgaris

<400> SEQUENCE: 169

Gly Val Gly Gly Leu Tyr Gly Gly Tyr Gly Leu Gly Gly Leu Tyr Gly
1 5 10 15

Gly Tyr Gly Leu Gly Gly Leu His Gly Gly Tyr Ser Leu Gly Gly Leu
20 25 30

Tyr Gly Gly Tyr Gly Ala His Tyr
35 40

<210> SEQ ID NO 170
<211> LENGTH: 33
<212> TYPE: PRT
<213> ORGANISM: Loligo vulgaris

<400> SEQUENCE: 170

Gly Val Gly Gly Leu Tyr Gly Gly Tyr Gly Leu Gly Gly Leu His Tyr
1 5 10 15

Gly Gly Tyr Gly Leu Gly Gly Leu His Tyr Gly Gly Tyr Gly Leu His
20 25 30

Tyr

<210> SEQ ID NO 171
<211> LENGTH: 15
<212> TYPE: PRT
<213> ORGANISM: Loligo vulgaris

<400> SEQUENCE: 171

Tyr Gly Tyr Gly Gly Leu Tyr Gly Gly Leu Tyr Gly Gly Leu Gly 1 5 10 15

<210> SEQ ID NO 172
<211> LENGTH: 15
<212> TYPE: PRT
<213> ORGANISM: Loligo vulgaris

<400> SEQUENCE: 172

Tyr Gly Tyr Gly Gly Leu Tyr Gly Gly Leu Tyr Gly Gly Leu Gly
1 5 10 15

<210> SEQ ID NO 173
<211> LENGTH: 41
<212> TYPE: PRT
<213> ORGANISM: Loligo vulgaris

<400> SEQUENCE: 173

Val Ala Tyr Gly Gly Trp Gly Tyr Gly Leu Gly Gly Leu His Gly Gly
1 5 10 15

Trp Gly Tyr Gly Leu Gly Gly Leu His Gly Gly Trp Gly Tyr Ala Leu
20 25 30

Gly Gly Leu Tyr Gly Gly Leu His Tyr
35 40

<210> SEQ ID NO 174
<211> LENGTH: 14
<212> TYPE: PRT
<213> ORGANISM: Loligo vulgaris

<400> SEQUENCE: 174

Val Gly Leu Gly Tyr Gly Gly Leu Tyr Gly Gly Leu His Tyr
1 5 10

<210> SEQ ID NO 175
<211> LENGTH: 19
<212> TYPE: PRT
<213> ORGANISM: Loligo vulgaris

<400> SEQUENCE: 175

Val Gly Tyr Gly Gly Phe Gly Leu Gly Phe Gly Gly Leu Tyr Gly Gly
1 5 10 15

Leu His Tyr

<210> SEQ ID NO 176
<211> LENGTH: 21
<212> TYPE: PRT
<213> ORGANISM: Loligo vulgaris

<400> SEQUENCE: 176

Ser Leu Gly Ala Tyr Gly Gly Tyr Gly Leu Gly Gly Leu Ile Gly Gly
1 5 10 15

His Ser Val Tyr His
20

<210> SEQ ID NO 177
<211> LENGTH: 21
<212> TYPE: PRT
<213> ORGANISM: Loligo vulgaris

<400> SEQUENCE: 177

Ser Leu Gly Ala Tyr Gly Gly Tyr Gly Leu Gly Gly Ile Val Gly Gly
1 5 10 15

Tyr Gly Ala Tyr Asn
20

<210> SEQ ID NO 178
<211> LENGTH: 19
<212> TYPE: PRT
<213> ORGANISM: Loligo vulgaris

<400> SEQUENCE: 178

Val Gly Tyr Gly Gly Phe Gly Leu Gly Phe Gly Gly Leu Tyr Gly Gly
1 5 10 15

Leu His Tyr

<210> SEQ ID NO 179
<211> LENGTH: 21
<212> TYPE: PRT
<213> ORGANISM: Loligo vulgaris

<400> SEQUENCE: 179

Val Gly Leu Gly Tyr Gly Gly Phe Gly Leu Gly Tyr Gly Gly Leu Tyr
1 5 10 15

Gly Gly Phe Gly Tyr
20

<210> SEQ ID NO 180
<211> LENGTH: 12
<212> TYPE: PRT
<213> ORGANISM: Loligo vulgaris

<400> SEQUENCE: 180

Val Ala Tyr Gly Gly Leu Gly Tyr Gly Phe Gly Phe
1 5 10

<210> SEQ ID NO 181
<211> LENGTH: 13
<212> TYPE: PRT
<213> ORGANISM: Loligo vulgaris

<400> SEQUENCE: 181

Gly Tyr Gly Gly Leu Tyr Gly Gly Leu Gly Tyr His Tyr
1 5 10

<210> SEQ ID NO 182
<211> LENGTH: 16
<212> TYPE: PRT
<213> ORGANISM: Loligo vulgaris

<400> SEQUENCE: 182

Tyr Gly Tyr Gly Gly Leu Tyr Gly Gly Leu Tyr Gly Gly Leu Gly Tyr
1 5 10 15

<210> SEQ ID NO 183
<211> LENGTH: 22
<212> TYPE: PRT
<213> ORGANISM: Loligo vulgaris

<400> SEQUENCE: 183

Val Gly Tyr Gly Gly Tyr Gly Leu Gly Ala Tyr Gly Ala Tyr Gly Leu
1 5 10 15

Gly Tyr Gly Leu His Tyr
20

<210> SEQ ID NO 184

<211> LENGTH: 22
<212> TYPE: PRT
<213> ORGANISM: Loligo vulgaris

<400> SEQUENCE: 184

Val Gly Tyr Gly Gly Tyr Gly Leu Gly Ala Tyr Gly Ala Tyr Gly Leu
1 5 10 15

Gly Tyr Gly Leu His Tyr
20

<210> SEQ ID NO 185
<211> LENGTH: 9
<212> TYPE: PRT
<213> ORGANISM: Loligo vulgaris

<400> SEQUENCE: 185

Val Gly Tyr Ala Gly Tyr Gly Leu Gly
1 5

<210> SEQ ID NO 186
<211> LENGTH: 9
<212> TYPE: PRT
<213> ORGANISM: Loligo vulgaris

<400> SEQUENCE: 186

Tyr Gly Gly Phe Gly Tyr Gly Leu Tyr
1 5

<210> SEQ ID NO 187
<211> LENGTH: 20
<212> TYPE: PRT
<213> ORGANISM: Loligo vulgaris

<400> SEQUENCE: 187

Gly Tyr Gly Gly Leu Tyr Gly His Tyr Gly Gly Tyr Gly Leu Gly Gly
1 5 10 15

Ala Tyr Gly His
20

<210> SEQ ID NO 188
<211> LENGTH: 51
<212> TYPE: PRT
<213> ORGANISM: Loligo vulgaris

<400> SEQUENCE: 188

Gly Ile Gly Gly Val Tyr Gly His Gly Ile Gly Gly Leu Gly Gly Val
1 5 10 15

Tyr Gly His Gly Ile Gly Gly Val Tyr Gly His Gly Ile Gly Gly Leu
20 25 30

Tyr Gly His Gly Phe Gly Gly Ala Tyr Gly Gly Tyr Gly Gly Tyr Gly
35 40 45

Ile Gly Gly
50

<210> SEQ ID NO 189
<211> LENGTH: 53
<212> TYPE: PRT
<213> ORGANISM: Loligo vulgaris

<400> SEQUENCE: 189

Val Thr Tyr Gly Gly Leu Gly Leu Gly Gly Leu Gly Tyr Gly Gly Leu
1 5 10 15

-continued

```
Gly Tyr Gly Gly Leu Gly Tyr Gly Gly Leu Gly Tyr Gly Gly Leu Gly
            20                  25                  30

Tyr Gly Gly Leu Gly Tyr Gly Gly Leu Gly Tyr Gly Gly Leu Gly Ala
        35                  40                  45

Gly Gly Leu Tyr Gly
    50


<210> SEQ ID NO 190
<211> LENGTH: 21
<212> TYPE: PRT
<213> ORGANISM: Loligo vulgaris

<400> SEQUENCE: 190

Gly Ala Val Gly Leu Gly Tyr Gly Leu Gly Gly Gly Tyr Gly Gly Leu
1               5                   10                  15

Tyr Gly Leu His Leu
            20


<210> SEQ ID NO 191
<211> LENGTH: 12
<212> TYPE: PRT
<213> ORGANISM: Loligo vulgaris

<400> SEQUENCE: 191

Ala Leu Gly Leu Gly Leu Tyr Gly Gly Ala His Leu
1               5                   10


<210> SEQ ID NO 192
<211> LENGTH: 12
<212> TYPE: PRT
<213> ORGANISM: Loligo vulgaris

<400> SEQUENCE: 192

Gly Leu Gly Leu Asn Tyr Gly Val Tyr Gly Leu His
1               5                   10


<210> SEQ ID NO 193
<211> LENGTH: 20
<212> TYPE: PRT
<213> ORGANISM: Loligo vulgaris

<400> SEQUENCE: 193

Gly Tyr Gly Gly Trp Gly Tyr Gly Leu Gly Gly Trp Gly His Gly Leu
1               5                   10                  15

Gly Gly Leu Gly
            20


<210> SEQ ID NO 194
<211> LENGTH: 17
<212> TYPE: PRT
<213> ORGANISM: Loligo palei

<400> SEQUENCE: 194

Tyr Gly Gly Ile Gly Leu Gly Gly Leu Tyr Gly Gly Tyr Gly Ala His
1               5                   10                  15

Phe


<210> SEQ ID NO 195
<211> LENGTH: 21
<212> TYPE: PRT
<213> ORGANISM: Loligo palei

<400> SEQUENCE: 195
```

```
His Ser Val Gly Trp Gly Leu Gly Gly Trp Gly Gly Tyr Gly Leu Gly
1               5                   10                  15

Tyr Gly Val His Ala
            20


<210> SEQ ID NO 196
<211> LENGTH: 21
<212> TYPE: PRT
<213> ORGANISM: Loligo palei

<400> SEQUENCE: 196

Ala Leu Gly Ala Tyr Gly Gly Tyr Gly Phe Gly Gly Ile Val Gly Gly
1               5                   10                  15

His Ser Val Tyr His
            20


<210> SEQ ID NO 197
<211> LENGTH: 16
<212> TYPE: PRT
<213> ORGANISM: Loligo palei

<400> SEQUENCE: 197

Ala Leu Gly Gly Tyr Gly Gly Tyr Gly Leu Gly Gly Ile Val Gly Gly
1               5                   10                  15


<210> SEQ ID NO 198
<211> LENGTH: 21
<212> TYPE: PRT
<213> ORGANISM: Loligo palei

<400> SEQUENCE: 198

Ala Leu Gly Ala Tyr Gly Gly Tyr Gly Leu Gly Gly Leu Val Gly Gly
1               5                   10                  15

Phe Gly Ala Tyr His
            20


<210> SEQ ID NO 199
<211> LENGTH: 39
<212> TYPE: PRT
<213> ORGANISM: Loligo palei

<400> SEQUENCE: 199

Val Gly Phe Gly Gly Tyr Gly Leu Gly Gly Tyr Gly Leu Gly Gly Tyr
1               5                   10                  15

Gly Leu Gly Gly Tyr Gly Leu Gly Gly Tyr Gly Leu Gly Gly Leu Val
            20                  25                  30

Gly Gly Tyr Gly Ser Tyr His
        35


<210> SEQ ID NO 200
<211> LENGTH: 25
<212> TYPE: PRT
<213> ORGANISM: Loligo palei

<400> SEQUENCE: 200

Val Gly Tyr Gly Gly Tyr Gly Leu Gly Gly Tyr Gly Gly Tyr Gly Leu
1               5                   10                  15

Gly Gly Leu Thr Gly Gly Tyr Gly Val
            20                  25


<210> SEQ ID NO 201
```

<211> LENGTH: 15
<212> TYPE: PRT
<213> ORGANISM: Loligo palei

<400> SEQUENCE: 201

Gly Tyr Gly Leu Gly Leu Gly Tyr Gly Leu Gly Leu Gly Ala Gly
1 5 10 15

<210> SEQ ID NO 202
<211> LENGTH: 21
<212> TYPE: PRT
<213> ORGANISM: Loligo palei

<400> SEQUENCE: 202

Leu Gly Leu Gly Tyr Gly Tyr Gly Leu Gly Leu Gly Tyr Gly Leu Gly
1 5 10 15

Leu Gly Ala Gly Ile
20

<210> SEQ ID NO 203
<211> LENGTH: 17
<212> TYPE: PRT
<213> ORGANISM: Loligo palei

<400> SEQUENCE: 203

His Leu Gly Leu Gly Leu Gly Tyr Gly Tyr Gly Leu Gly His Gly Leu
1 5 10 15

Gly

<210> SEQ ID NO 204
<211> LENGTH: 16
<212> TYPE: PRT
<213> ORGANISM: Loligo palei

<400> SEQUENCE: 204

Gly Leu Gly Leu Gly Tyr Gly Leu Gly Leu Gly Tyr Gly Tyr Gly Val
1 5 10 15

<210> SEQ ID NO 205
<211> LENGTH: 15
<212> TYPE: PRT
<213> ORGANISM: Loligo palei

<400> SEQUENCE: 205

Gly Tyr Gly Leu Gly Leu Gly Leu Gly Gly Ala Gly Tyr Gly Tyr
1 5 10 15

<210> SEQ ID NO 206
<211> LENGTH: 19
<212> TYPE: PRT
<213> ORGANISM: Loligo palei

<400> SEQUENCE: 206

Val Gly Gly Tyr Gly Gly Phe Gly Leu Gly Gly Tyr Gly Gly Tyr Gly
1 5 10 15

Leu Gly Gly

<210> SEQ ID NO 207
<211> LENGTH: 58
<212> TYPE: PRT
<213> ORGANISM: Loligo palei

<400> SEQUENCE: 207

```
Val Gly Tyr Gly Gly Leu Tyr Gly His Tyr Gly Gly Tyr Gly Leu Gly
1               5                   10                  15

Gly Val Tyr Gly His Gly Val Gly Leu Gly Gly Val Tyr Gly His Gly
            20                  25                  30

Ile Gly Gly Ala Tyr Gly Gly Tyr Gly Leu Gly Val Gly Gly Leu Tyr
        35                  40                  45

Gly Gly Tyr Gly Gly Tyr Gly Ile Gly Gly
    50                  55


<210> SEQ ID NO 208
<211> LENGTH: 19
<212> TYPE: PRT
<213> ORGANISM: Loligo palei

<400> SEQUENCE: 208

Val Gly Gly Tyr Gly Gly Phe Gly Leu Gly Gly Tyr Gly Gly Tyr Gly
1               5                   10                  15

Leu Gly Gly


<210> SEQ ID NO 209
<211> LENGTH: 41
<212> TYPE: PRT
<213> ORGANISM: Loligo palei

<400> SEQUENCE: 209

Val Gly Tyr Gly Gly Leu Tyr Gly His Tyr Gly Gly Tyr Gly Leu Gly
1               5                   10                  15

Gly Val Tyr Gly His Gly Val Gly Leu Gly Gly Val Tyr Gly His Gly
            20                  25                  30

Val Gly Leu Gly Gly Val Tyr Ser His
        35                  40


<210> SEQ ID NO 210
<211> LENGTH: 27
<212> TYPE: PRT
<213> ORGANISM: Loligo palei

<400> SEQUENCE: 210

Gly Ile Gly Gly Ala Tyr Gly Gly Tyr Gly Leu Gly Val Gly Gly Leu
1               5                   10                  15

Tyr Gly Gly Tyr Gly Gly Tyr Gly Ile Gly Gly
            20                  25


<210> SEQ ID NO 211
<211> LENGTH: 19
<212> TYPE: PRT
<213> ORGANISM: Loligo palei

<400> SEQUENCE: 211

Val Leu Ser Gly Gly Leu Gly Leu Ser Gly Leu Ser Gly Gly Tyr Gly
1               5                   10                  15

Thr Tyr Arg


<210> SEQ ID NO 212
<211> LENGTH: 27
<212> TYPE: PRT
<213> ORGANISM: Loligo palei

<400> SEQUENCE: 212

Gly Tyr Gly Gly Val Gly Tyr Gly Gly Leu Gly Tyr Gly Gly Leu Gly
1               5                   10                  15
```

```
Tyr Gly Val Gly Gly Leu Tyr Gly Leu Gln Tyr
            20                  25


<210> SEQ ID NO 213
<211> LENGTH: 26
<212> TYPE: PRT
<213> ORGANISM: Loligo palei

<400> SEQUENCE: 213

Gly Tyr Gly Gly Trp Gly Tyr Gly Leu Gly Gly Trp Gly His Gly Leu
1               5                   10                  15

Gly Gly Leu Gly Ser Tyr Gly Leu His Tyr
            20                  25


<210> SEQ ID NO 214
<211> LENGTH: 21
<212> TYPE: PRT
<213> ORGANISM: Loligo palei

<400> SEQUENCE: 214

His Ser Val Gly Trp Gly Leu Gly Gly Trp Gly Gly Tyr Gly Leu Gly
1               5                   10                  15

Tyr Gly Val Arg Ser
            20


<210> SEQ ID NO 215
<211> LENGTH: 19
<212> TYPE: PRT
<213> ORGANISM: Loligo palei

<400> SEQUENCE: 215

Tyr Gly Asp Val Tyr Gly Gly Leu Tyr Gly Gly Leu Tyr Gly Gly Leu
1               5                   10                  15

Leu Gly Ala


<210> SEQ ID NO 216
<211> LENGTH: 35
<212> TYPE: PRT
<213> ORGANISM: Loligo palei

<400> SEQUENCE: 216

Val Ala Tyr Gly Gly Leu Gly Leu Gly Ala Leu Gly Tyr Gly Gly Leu
1               5                   10                  15

Gly Tyr Gly Gly Leu Gly Tyr Gly Gly Leu Gly Ala Gly Gly Leu Tyr
            20                  25                  30

Gly Leu His
        35


<210> SEQ ID NO 217
<211> LENGTH: 13
<212> TYPE: PRT
<213> ORGANISM: Loligo palei

<400> SEQUENCE: 217

Gly Tyr Gly Leu Gly Leu Gly Leu Tyr Gly Ala His Leu
1               5                   10


<210> SEQ ID NO 218
<211> LENGTH: 26
<212> TYPE: PRT
<213> ORGANISM: Loligo palei
```

<400> SEQUENCE: 218

Ala Tyr Gly Gly Trp Gly Tyr Ser Leu Gly Arg Trp Gly Gln Gly Leu
1 5 10 15

Gly Gly Leu Gly Thr Tyr Gly Leu His Tyr
20 25

<210> SEQ ID NO 219
<211> LENGTH: 21
<212> TYPE: PRT
<213> ORGANISM: Loligo palei

<400> SEQUENCE: 219

His Ser Val Gly Trp Gly Leu Gly Gly Trp Gly Gly Tyr Gly Leu Gly
1 5 10 15

Tyr Gly Val His Ala
20

<210> SEQ ID NO 220
<211> LENGTH: 21
<212> TYPE: PRT
<213> ORGANISM: Loligo palei

<400> SEQUENCE: 220

Ala Leu Gly Gly Tyr Gly Gly Tyr Gly Leu Gly Gly Ile Val Gly Gly
1 5 10 15

His Ser Val Tyr His
20

<210> SEQ ID NO 221
<211> LENGTH: 17
<212> TYPE: PRT
<213> ORGANISM: Loligo palei

<400> SEQUENCE: 221

Ala Leu Gly Glu Tyr Gly Gly Tyr Gly Leu Gly Gly Ile Val Gly Gly
1 5 10 15

His

<210> SEQ ID NO 222
<211> LENGTH: 20
<212> TYPE: PRT
<213> ORGANISM: Loligo palei

<400> SEQUENCE: 222

Gly Phe Gly Gly Tyr Gly Leu Gly Gly Tyr Gly Leu Gly Gly Tyr Gly
1 5 10 15

Leu Gly Gly Tyr
20

<210> SEQ ID NO 223
<211> LENGTH: 33
<212> TYPE: PRT
<213> ORGANISM: Loligo palei

<400> SEQUENCE: 223

Ile Gly Phe Gly Gly Trp Gly His Gly Tyr Gly Tyr Ser Gly Leu Gly
1 5 10 15

Phe Gly Gly Trp Gly His Gly Leu Gly Gly Trp Gly His Gly Tyr Gly
20 25 30

Tyr

<210> SEQ ID NO 224
<211> LENGTH: 33
<212> TYPE: PRT
<213> ORGANISM: Loligo palei

<400> SEQUENCE: 224

Ile Gly Phe Gly Gly Trp Gly His Gly Tyr Gly Tyr Ser Gly Leu Gly
1 5 10 15

Phe Gly Gly Trp Gly His Gly Leu Gly Gly Trp Gly His Gly Tyr Gly
20 25 30

Tyr

<210> SEQ ID NO 225
<211> LENGTH: 14
<212> TYPE: PRT
<213> ORGANISM: Loligo palei

<400> SEQUENCE: 225

His Ala Val Gly Phe Gly Gly Trp Gly His Gly Phe Gly Tyr
1 5 10

<210> SEQ ID NO 226
<211> LENGTH: 19
<212> TYPE: PRT
<213> ORGANISM: Loligo palei

<400> SEQUENCE: 226

His Ser Val Ser Tyr Gly Gly Trp Gly Phe Gly His Gly Gly Leu Tyr
1 5 10 15

Gly Leu His

<210> SEQ ID NO 227
<211> LENGTH: 16
<212> TYPE: PRT
<213> ORGANISM: Loligo palei

<400> SEQUENCE: 227

His Ala Asp Tyr Gly Val Ser Gly Leu Gly Gly Tyr Val Ser Ser Tyr
1 5 10 15

<210> SEQ ID NO 228
<211> LENGTH: 21
<212> TYPE: PRT
<213> ORGANISM: Loligo palei

<400> SEQUENCE: 228

His Ser Val Gly Trp Gly Leu Gly Gly Trp Gly Gly Tyr Gly Leu Gly
1 5 10 15

Tyr Gly Val His Ala
20

<210> SEQ ID NO 229
<211> LENGTH: 21
<212> TYPE: PRT
<213> ORGANISM: Loligo palei

<400> SEQUENCE: 229

Ala Leu Gly Ala Tyr Gly Gly Tyr Gly Phe Gly Gly Ile Val Gly Gly
1 5 10 15

His Ser Val Tyr His
20

```
<210> SEQ ID NO 230
<211> LENGTH: 39
<212> TYPE: PRT
<213> ORGANISM: Loligo palei

<400> SEQUENCE: 230

Val Gly Phe Gly Gly Tyr Gly Leu Gly Gly Tyr Gly Leu Gly Gly Tyr
1               5                   10                  15

Gly Leu Gly Gly Tyr Gly Leu Gly Gly Tyr Gly Leu Gly Gly Val Val
            20                  25                  30

Gly Gly Phe Gly Gly Tyr His
        35


<210> SEQ ID NO 231
<211> LENGTH: 28
<212> TYPE: PRT
<213> ORGANISM: Loligo palei

<400> SEQUENCE: 231

Phe Gly Tyr Gly Gly Val Gly Tyr Gly Gly Leu Gly Tyr Gly Gly Leu
1               5                   10                  15

Gly Tyr Gly Val Gly Gly Leu Tyr Gly Leu Gln Tyr
            20                  25


<210> SEQ ID NO 232
<211> LENGTH: 31
<212> TYPE: PRT
<213> ORGANISM: Loligo palei

<400> SEQUENCE: 232

Val Ala Tyr Gly Gly Leu Gly Leu Gly Ala Leu Gly Tyr Gly Gly Leu
1               5                   10                  15

Gly Tyr Gly Gly Leu Gly Ala Gly Gly Leu Tyr Gly Leu His Tyr
            20                  25                  30


<210> SEQ ID NO 233
<211> LENGTH: 18
<212> TYPE: PRT
<213> ORGANISM: Loligo palei

<400> SEQUENCE: 233

Ala Gly Leu Gly Tyr Gly Leu Gly Gly Val Tyr Gly Gly Tyr Gly Leu
1               5                   10                  15

His Ala


<210> SEQ ID NO 234
<211> LENGTH: 29
<212> TYPE: PRT
<213> ORGANISM: Loligo palei

<400> SEQUENCE: 234

Tyr Gly Tyr Gly Gly Leu Tyr Gly Gly Leu Gly Tyr His Ala Gly Tyr
1               5                   10                  15

Gly Leu Gly Gly Tyr Gly Leu Gly Tyr Gly Leu His Tyr
            20                  25


<210> SEQ ID NO 235
<211> LENGTH: 14
<212> TYPE: PRT
<213> ORGANISM: Loligo palei

<400> SEQUENCE: 235
```

```
Val Gly Trp Gly Leu Gly Gly Leu Tyr Gly Gly Leu His His
1               5                   10


<210> SEQ ID NO 236
<211> LENGTH: 18
<212> TYPE: PRT
<213> ORGANISM: Loligo palei

<400> SEQUENCE: 236

Gly Tyr Gly Gly Tyr Gly Leu Gly Leu Gly Gly Leu Tyr Gly Gly Leu
1               5                   10                  15

His Tyr


<210> SEQ ID NO 237
<211> LENGTH: 18
<212> TYPE: PRT
<213> ORGANISM: Loligo palei

<400> SEQUENCE: 237

Gly Tyr Gly Gly Tyr Gly Leu Gly Phe Gly Gly Leu Tyr Gly Gly Phe
1               5                   10                  15

Gly Tyr


<210> SEQ ID NO 238
<211> LENGTH: 24
<212> TYPE: PRT
<213> ORGANISM: Loligo palei

<400> SEQUENCE: 238

Ala Tyr Gly Tyr Gly Tyr Gly Leu Gly Gly Tyr Gly Gly Tyr Gly Leu
1               5                   10                  15

Tyr Gly Gly Tyr Gly Leu His His
            20


<210> SEQ ID NO 239
<211> LENGTH: 29
<212> TYPE: PRT
<213> ORGANISM: Loligo palei

<400> SEQUENCE: 239

Val Ala Tyr Gly Gly Trp Gly Tyr Gly Leu Gly Gly Leu His Gly Gly
1               5                   10                  15

Trp Gly Tyr Gly Leu Gly Gly Leu Tyr Gly Gly Leu His
            20                  25


<210> SEQ ID NO 240
<211> LENGTH: 18
<212> TYPE: PRT
<213> ORGANISM: Loligo palei

<400> SEQUENCE: 240

Gly Tyr Gly Gly Tyr Gly Leu Gly Leu Gly Gly Leu Tyr Gly Gly Leu
1               5                   10                  15

His Tyr


<210> SEQ ID NO 241
<211> LENGTH: 18
<212> TYPE: PRT
<213> ORGANISM: Loligo palei

<400> SEQUENCE: 241
```

```
Gly Tyr Gly Gly Tyr Gly Leu Gly Phe Gly Gly Leu Tyr Gly Gly Phe
1               5                   10                  15

Gly Tyr


<210> SEQ ID NO 242
<211> LENGTH: 30
<212> TYPE: PRT
<213> ORGANISM: Loligo palei

<400> SEQUENCE: 242

Val Gly Tyr Ala Gly Tyr Gly Tyr Gly Leu Gly Ser Tyr Gly Gly Tyr
1               5                   10                  15

Ala Gly Leu Gly Leu Gly Leu Tyr Gly Ala Gly Tyr His Tyr
            20                  25                  30


<210> SEQ ID NO 243
<211> LENGTH: 17
<212> TYPE: PRT
<213> ORGANISM: Loligo palei

<400> SEQUENCE: 243

Tyr Ala Tyr Gly Gly Leu Tyr Gly Gly Tyr Gly Leu Gly Ala Tyr Gly
1               5                   10                  15

Tyr


<210> SEQ ID NO 244
<211> LENGTH: 30
<212> TYPE: PRT
<213> ORGANISM: Loligo palei

<400> SEQUENCE: 244

Val Gly Tyr Ala Gly Tyr Gly Tyr Gly Leu Gly Ala Tyr Gly Gly Tyr
1               5                   10                  15

Ala Gly Leu Gly Leu Gly Leu Tyr Gly Ala Gly Tyr His Tyr
            20                  25                  30


<210> SEQ ID NO 245
<211> LENGTH: 17
<212> TYPE: PRT
<213> ORGANISM: Loligo palei

<400> SEQUENCE: 245

Tyr Ala Tyr Gly Gly Leu Tyr Gly Gly Tyr Gly Leu Gly Ala Tyr Gly
1               5                   10                  15

Tyr


<210> SEQ ID NO 246
<211> LENGTH: 15
<212> TYPE: PRT
<213> ORGANISM: Loligo palei

<400> SEQUENCE: 246

Val Gly Tyr Gly Gly Phe Gly Leu Ala Gly Tyr Gly Tyr Gly Tyr
1               5                   10                  15


<210> SEQ ID NO 247
<211> LENGTH: 24
<212> TYPE: PRT
<213> ORGANISM: Loligo palei

<400> SEQUENCE: 247

Tyr Gly Tyr Gly Gly Leu Tyr Gly Gly Tyr Ala Gly Leu Gly Leu Gly
```

```
1               5                   10                  15

Leu Tyr Gly Ala Gly Tyr His Tyr
            20


<210> SEQ ID NO 248
<211> LENGTH: 17
<212> TYPE: PRT
<213> ORGANISM: Loligo palei

<400> SEQUENCE: 248

Tyr Ala Tyr Gly Gly Leu Tyr Gly Gly Tyr Gly Leu Gly Ala Tyr Gly
1               5                   10                  15

Tyr


<210> SEQ ID NO 249
<211> LENGTH: 30
<212> TYPE: PRT
<213> ORGANISM: Loligo palei

<400> SEQUENCE: 249

Val Gly Tyr Ala Gly Tyr Gly Tyr Gly Leu Gly Ala Tyr Gly Gly Tyr
1               5                   10                  15

Ala Gly Leu Gly Leu Gly Leu Tyr Gly Ala Gly Tyr His Tyr
            20                  25                  30


<210> SEQ ID NO 250
<211> LENGTH: 17
<212> TYPE: PRT
<213> ORGANISM: Loligo palei

<400> SEQUENCE: 250

Tyr Ala Tyr Gly Gly Leu Tyr Gly Gly Tyr Gly Leu Gly Ala Tyr Gly
1               5                   10                  15

Tyr


<210> SEQ ID NO 251
<211> LENGTH: 17
<212> TYPE: PRT
<213> ORGANISM: Loligo palei

<400> SEQUENCE: 251

Val Gly Tyr Ala Gly Tyr Gly Leu Gly Leu Tyr Gly Ala Gly Tyr His
1               5                   10                  15

Tyr


<210> SEQ ID NO 252
<211> LENGTH: 17
<212> TYPE: PRT
<213> ORGANISM: Loligo palei

<400> SEQUENCE: 252

Tyr Ala Tyr Gly Gly Leu Tyr Gly Gly Tyr Gly Leu Gly Ala Tyr Gly
1               5                   10                  15

Tyr


<210> SEQ ID NO 253
<211> LENGTH: 50
<212> TYPE: PRT
<213> ORGANISM: Loligo palei

<400> SEQUENCE: 253
```

```
Val Gly Tyr Ala Gly Tyr Gly Leu Gly Ala Tyr Gly Gly Tyr Ala Gly
1               5                   10                  15

Tyr Gly Leu Gly Ala Phe Gly Gly Tyr Ala Gly Tyr Gly Leu Gly Ala
            20                  25                  30

Phe Gly Gly Tyr Ala Gly Leu Gly Leu Gly Leu Tyr Gly Ala Gly Tyr
        35                  40                  45

His Tyr
    50


<210> SEQ ID NO 254
<211> LENGTH: 42
<212> TYPE: PRT
<213> ORGANISM: Loligo palei

<400> SEQUENCE: 254

Leu Gly Phe Gly Gly Leu Leu Gly Gly Tyr Gly Gly Leu His His Gly
1               5                   10                  15

Val Tyr Gly Leu Gly Gly Tyr Gly Gly Leu Tyr Gly Gly Tyr Gly Leu
            20                  25                  30

Gly Gly Tyr Gly Leu His Gly Leu His Tyr
        35                  40


<210> SEQ ID NO 255
<211> LENGTH: 58
<212> TYPE: PRT
<213> ORGANISM: Loligo palei

<400> SEQUENCE: 255

Leu Gly Phe Gly Gly Val Leu Gly Tyr Gly Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Gly Leu His Gly Ala Tyr Gly Leu Gly Gly Tyr Gly Gly
        35                  40                  45

Leu Tyr Gly Gly Tyr Gly Leu Gly Gly His
    50                  55


<210> SEQ ID NO 256
<211> LENGTH: 58
<212> TYPE: PRT
<213> ORGANISM: Loligo palei

<400> SEQUENCE: 256

Val Gly Tyr Gly Gly Tyr Gly Tyr Gly Gly Leu Gly Ala Tyr Gly His
1               5                   10                  15

Tyr Gly Gly Tyr Gly Leu Gly Gly Leu Tyr Gly Gly Tyr Gly Leu Gly
            20                  25                  30

Gly Ala Tyr Gly Gly Tyr Gly Leu Gly Gly Gly Tyr Gly Gly Tyr Gly
        35                  40                  45

Val Gly Val His Ser Arg Tyr Gly Val Gly
    50                  55


<210> SEQ ID NO 257
<211> LENGTH: 15
<212> TYPE: PRT
<213> ORGANISM: Loligo palei

<400> SEQUENCE: 257

Gly Tyr Gly Tyr Gly Gly Leu Leu Gly Gly Tyr Gly Leu His Tyr
1               5                   10                  15
```

<210> SEQ ID NO 258
<211> LENGTH: 29
<212> TYPE: PRT
<213> ORGANISM: Loligo palei

<400> SEQUENCE: 258

Tyr Gly Tyr Gly Leu Ala Gly Tyr Gly Gly Leu Tyr Gly Gly Leu His
1 5 10 15

Gly Ala Ala Tyr Gly Leu Gly Gly Tyr Gly Leu His Tyr
20 25

<210> SEQ ID NO 259
<211> LENGTH: 38
<212> TYPE: PRT
<213> ORGANISM: Loligo palei

<400> SEQUENCE: 259

Leu Gly Tyr Gly Leu Ala Gly Tyr Gly Gly Leu Tyr Gly Gly Leu Tyr
1 5 10 15

Gly Gly His Gly Leu Gly Gly Tyr Gly Gly Val Tyr Gly Gly Tyr Gly
20 25 30

Leu His Gly Leu His Tyr
35

<210> SEQ ID NO 260
<211> LENGTH: 14
<212> TYPE: PRT
<213> ORGANISM: Loligo palei

<400> SEQUENCE: 260

Leu Gly Phe Gly Gly Val Leu Gly Tyr Gly Gly Leu His His
1 5 10

<210> SEQ ID NO 261
<211> LENGTH: 57
<212> TYPE: PRT
<213> ORGANISM: Loligo palei

<400> SEQUENCE: 261

Gly Val Tyr Gly Leu Gly His Gly Ala Tyr Gly Leu Gly Gly Tyr Gly
1 5 10 15

Gly Leu His Gly Ala Tyr Gly Leu Gly Gly Tyr Gly Gly Leu Tyr Gly
20 25 30

Gly Tyr Gly Leu Gly Gly Tyr Gly Ala Leu His Gly Gly Leu Tyr Gly
35 40 45

Gly Tyr Gly Leu Gly Gly Gly Leu Leu
50 55

<210> SEQ ID NO 262
<211> LENGTH: 17
<212> TYPE: PRT
<213> ORGANISM: Loligo palei

<400> SEQUENCE: 262

Tyr Ser Tyr Gly Gly Leu Val Gly Gly Tyr Gly Gly Leu Tyr His His
1 5 10 15

Ala

<210> SEQ ID NO 263
<211> LENGTH: 48

<212> TYPE: PRT
<213> ORGANISM: Loligo palei

<400> SEQUENCE: 263

```
Leu Phe Gly Gly Ile Leu Gly Gly Tyr Gly Gly Val Leu Ala Gly Tyr
1               5                   10                  15

Gly Gly Leu His His Gly Ala Tyr Gly Leu Gly Gly Tyr Gly Gly Leu
            20                  25                  30

Tyr Gly Gly Tyr Gly Leu Gly Gly Tyr Gly Leu His Gly Leu His Tyr
        35                  40                  45
```

<210> SEQ ID NO 264
<211> LENGTH: 57
<212> TYPE: PRT
<213> ORGANISM: Loligo palei

<400> SEQUENCE: 264

```
Leu Gly Phe Gly Gly Val Leu Gly Tyr Gly Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Gly Leu His Gly Ala Tyr Gly Leu Gly Gly Tyr Gly Gly
        35                  40                  45

Leu Tyr Gly Gly Thr Leu Ser Thr Leu
    50                  55
```

<210> SEQ ID NO 265
<211> LENGTH: 16
<212> TYPE: PRT
<213> ORGANISM: Loligo palei

<400> SEQUENCE: 265

```
Gly Tyr Gly Tyr Gly Gly Leu Leu Gly Gly Leu Gly His Ala Val Gly
1               5                   10                  15
```

<210> SEQ ID NO 266
<211> LENGTH: 27
<212> TYPE: PRT
<213> ORGANISM: Loligo palei

<400> SEQUENCE: 266

```
Val Gly Tyr Gly Tyr Gly Gly Leu Leu Gly Gly Tyr Gly Gly Leu Tyr
1               5                   10                  15

Gly Gly Trp Gly Gly Val Tyr Gly Gly Leu Gly
            20                  25
```

<210> SEQ ID NO 267
<211> LENGTH: 21
<212> TYPE: PRT
<213> ORGANISM: Loligo palei

<400> SEQUENCE: 267

```
Val Gly Tyr Gly Tyr Gly Gly Phe Leu Gly Gly Tyr Gly Leu Gly Val
1               5                   10                  15

Tyr Gly His Gly Tyr
            20
```

<210> SEQ ID NO 268
<211> LENGTH: 38
<212> TYPE: PRT
<213> ORGANISM: Loligo palei

<400> SEQUENCE: 268

```
Leu Gly Tyr Gly Leu Ala Gly Tyr Gly Gly Leu Tyr Gly Gly Leu Tyr
1               5                   10                  15

Gly Gly His Gly Leu Gly Gly Tyr Gly Gly Val Tyr Gly Gly Tyr Gly
            20                  25                  30

Leu His Gly Leu His Tyr
        35
```

<210> SEQ ID NO 269
<211> LENGTH: 75
<212> TYPE: PRT
<213> ORGANISM: Loligo palei

<400> SEQUENCE: 269

```
Leu Gly Phe Gly Gly Val Leu Gly Tyr Gly Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Gly Leu His Gly Ala Tyr Gly Leu Gly Gly Tyr Gly Gly
        35                  40                  45

Leu Tyr Gly Gly Tyr Gly Leu Gly Gly Tyr Gly Ala Leu His Gly Gly
    50                  55                  60

Leu Tyr Gly Gly Tyr Gly Leu Gly Gly Gly Leu
65                  70                  75
```

<210> SEQ ID NO 270
<211> LENGTH: 15
<212> TYPE: PRT
<213> ORGANISM: Todarodes pacificus

<400> SEQUENCE: 270

```
Gly Tyr Gly Tyr Gly Gly Leu Leu Gly Gly Tyr Gly Leu His Tyr
1               5                   10                  15
```

<210> SEQ ID NO 271
<211> LENGTH: 24
<212> TYPE: PRT
<213> ORGANISM: Todarodes pacificus

<400> SEQUENCE: 271

```
Tyr Gly Tyr Gly Leu Ala Gly Tyr Gly Gly Leu Tyr Gly Gly Tyr Gly
1               5                   10                  15

Leu Gly Gly Tyr Gly Leu Gly Tyr
            20
```

<210> SEQ ID NO 272
<211> LENGTH: 38
<212> TYPE: PRT
<213> ORGANISM: Todarodes pacificus

<400> SEQUENCE: 272

```
Leu Gly Tyr Gly Leu Ala Gly Tyr Gly Gly Leu Tyr Gly Gly Leu Tyr
1               5                   10                  15

Gly Gly His Gly Leu Gly Gly Tyr Gly Gly Val Tyr Gly Gly Tyr Gly
            20                  25                  30

Leu His Gly Leu His Tyr
        35
```

<210> SEQ ID NO 273
<211> LENGTH: 47

```
<212> TYPE: PRT
<213> ORGANISM: Todarodes pacificus

<400> SEQUENCE: 273

Leu Gly Phe Gly Gly Val Leu Gly Tyr Gly Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Leu Gly Gly Phe His Gly Gly Tyr Gly Leu Gly Gly
        35                  40                  45


<210> SEQ ID NO 274
<211> LENGTH: 27
<212> TYPE: PRT
<213> ORGANISM: Todarodes pacificus

<400> SEQUENCE: 274

Val Gly Leu Gly Leu Gly Gly Phe His Gly Gly Tyr Gly Phe Gly Gly
1               5                   10                  15

Tyr Gly Leu Gly Gly Phe His Gly Gly Tyr Gly
            20                  25


<210> SEQ ID NO 275
<211> LENGTH: 38
<212> TYPE: PRT
<213> ORGANISM: Todarodes pacificus

<400> SEQUENCE: 275

Val Gly Phe Gly Gly Tyr Gly Tyr Gly Gly Ile Gly Gly Leu Tyr Gly
1               5                   10                  15

Gly His Tyr Gly Gly Tyr Gly Leu Gly Gly Ala Tyr Gly His Tyr Gly
            20                  25                  30

Gly Tyr Gly Leu Gly Gly
        35


<210> SEQ ID NO 276
<211> LENGTH: 16
<212> TYPE: PRT
<213> ORGANISM: Todarodes pacificus

<400> SEQUENCE: 276

Gly Tyr Gly Tyr Gly Gly Leu Leu Gly Gly Leu Gly His Ala Val Gly
1               5                   10                  15


<210> SEQ ID NO 277
<211> LENGTH: 26
<212> TYPE: PRT
<213> ORGANISM: Todarodes pacificus

<400> SEQUENCE: 277

Gly Tyr Gly Tyr Gly Gly Leu Leu Gly Gly Tyr Gly Gly Leu Tyr Gly
1               5                   10                  15

Gly Trp Gly Gly Val Tyr Gly Gly Leu Gly
            20                  25


<210> SEQ ID NO 278
<211> LENGTH: 21
<212> TYPE: PRT
<213> ORGANISM: Todarodes pacificus

<400> SEQUENCE: 278

Val Gly Tyr Gly Tyr Gly Gly Phe Leu Gly Gly Tyr Gly Leu Gly Val
```

```
1               5                   10                  15

Tyr Gly His Gly Tyr
            20


<210> SEQ ID NO 279
<211> LENGTH: 26
<212> TYPE: PRT
<213> ORGANISM: Todarodes pacificus

<400> SEQUENCE: 279

Leu Gly Tyr Gly Gly Leu Leu Gly Gly Tyr Gly Gly Leu Tyr Gly Gly
1               5                   10                  15

Tyr Gly Leu Gly Gly Tyr Gly Leu Gly Tyr
            20                  25


<210> SEQ ID NO 280
<211> LENGTH: 17
<212> TYPE: PRT
<213> ORGANISM: Todarodes pacificus

<400> SEQUENCE: 280

Tyr Gly Tyr Gly Leu Ala Gly Tyr Gly Gly Leu Tyr Gly Gly Leu Leu
1               5                   10                  15

His


<210> SEQ ID NO 281
<211> LENGTH: 38
<212> TYPE: PRT
<213> ORGANISM: Todarodes pacificus

<400> SEQUENCE: 281

Leu Gly Tyr Gly Leu Ala Gly Tyr Gly Gly Leu Tyr Gly Gly Leu Tyr
1               5                   10                  15

Gly Gly His Gly Leu Gly Gly Tyr Gly Gly Val Tyr Gly Gly Tyr Gly
            20                  25                  30

Leu His Gly Leu His Tyr
        35


<210> SEQ ID NO 282
<211> LENGTH: 52
<212> TYPE: PRT
<213> ORGANISM: Todarodes pacificus

<400> SEQUENCE: 282

Leu Gly Phe Gly Gly Val Leu Gly Tyr Gly Gly Leu His His Gly Ala
1               5                   10                  15

Tyr Gly Leu Gly Gly Tyr Gly Gly Leu Tyr Gly Gly Tyr Gly Leu Gly
            20                  25                  30

Gly Tyr Gly Gly Leu Tyr Gly Gly Tyr Gly Ala Leu His Gly Gly Tyr
        35                  40                  45

Gly Leu Gly Tyr
    50


<210> SEQ ID NO 283
<211> LENGTH: 15
<212> TYPE: PRT
<213> ORGANISM: Todarodes pacificus

<400> SEQUENCE: 283

Tyr Gly Leu Ala Gly Tyr Gly Gly Leu Tyr Gly Gly Leu Leu His
1               5                   10                  15
```

<210> SEQ ID NO 284
<211> LENGTH: 21
<212> TYPE: PRT
<213> ORGANISM: Todarodes pacificus

<400> SEQUENCE: 284

```
Thr Ala Leu Gly Tyr Gly Gly Leu Tyr Gly Gly Tyr Gly Leu Gly Ala
1               5                   10                  15

Tyr Gly Leu Gly Tyr
            20
```

<210> SEQ ID NO 285
<211> LENGTH: 26
<212> TYPE: PRT
<213> ORGANISM: Todarodes pacificus

<400> SEQUENCE: 285

```
Leu Gly Tyr Gly Gly Leu Leu Gly Gly Tyr Gly Gly Leu Tyr Gly Arg
1               5                   10                  15

Tyr Gly Val Gly Gly Tyr Gly Leu Gly Tyr
            20                  25
```

<210> SEQ ID NO 286
<211> LENGTH: 19
<212> TYPE: PRT
<213> ORGANISM: Todarodes pacificus

<400> SEQUENCE: 286

```
Gly Gly Tyr Gly Ser Leu Leu Gly Gly His Gly Gly Leu Tyr Gly Gly
1               5                   10                  15

Leu Gly Leu
```

<210> SEQ ID NO 287
<211> LENGTH: 13
<212> TYPE: PRT
<213> ORGANISM: Todarodes pacificus

<400> SEQUENCE: 287

```
Tyr Gly Tyr Gly Gly Val Leu Gly Gly Tyr Gly Gln Gly
1               5                   10
```

<210> SEQ ID NO 288
<211> LENGTH: 19
<212> TYPE: PRT
<213> ORGANISM: Todarodes pacificus

<400> SEQUENCE: 288

```
Leu Gly Tyr Gly Gly Leu Leu Gly Gly Tyr Gly Gly Leu His His Gly
1               5                   10                  15

Val Tyr Gly
```

<210> SEQ ID NO 289
<211> LENGTH: 39
<212> TYPE: PRT
<213> ORGANISM: Todarodes pacificus

<400> SEQUENCE: 289

```
Gly Gly Tyr Gly Gly Leu Tyr Gly Gly Tyr Gly Leu Gly Gly Tyr Gly
1               5                   10                  15

Gly Leu His Gly Ala Tyr Gly Leu Gly Gly Tyr Gly Gly Val Tyr Gly
            20                  25                  30
```

```
Gly Tyr Gly Leu Gly Gly His
        35


<210> SEQ ID NO 290
<211> LENGTH: 30
<212> TYPE: PRT
<213> ORGANISM: Todarodes pacificus

<400> SEQUENCE: 290

Val Gly Tyr Gly Gly Tyr Gly Tyr Gly Gly Leu Gly Ala Tyr Gly His
1               5                   10                  15

Tyr Gly Gly Tyr Gly Leu Gly Gly Leu Tyr Gly Gly Tyr Gly
            20                  25                  30


<210> SEQ ID NO 291
<211> LENGTH: 27
<212> TYPE: PRT
<213> ORGANISM: Todarodes pacificus

<400> SEQUENCE: 291

Val Gly Tyr Gly Tyr Gly Gly Leu Leu Gly Gly Tyr Gly Gly Leu Tyr
1               5                   10                  15

Gly Gly Trp Gly Gly Val Tyr Gly Gly Leu Gly
            20                  25


<210> SEQ ID NO 292
<211> LENGTH: 21
<212> TYPE: PRT
<213> ORGANISM: Todarodes pacificus

<400> SEQUENCE: 292

Val Gly Tyr Gly Tyr Gly Gly Phe Leu Gly Gly Tyr Gly Leu Gly Val
1               5                   10                  15

Tyr Gly His Gly Tyr
            20


<210> SEQ ID NO 293
<211> LENGTH: 38
<212> TYPE: PRT
<213> ORGANISM: Todarodes pacificus

<400> SEQUENCE: 293

Leu Gly Tyr Gly Leu Ala Gly Tyr Gly Gly Leu Tyr Gly Gly Leu Tyr
1               5                   10                  15

Gly Gly His Gly Leu Gly Gly Tyr Gly Gly Val Tyr Gly Gly Tyr Gly
            20                  25                  30

Leu His Gly Leu His Tyr
        35


<210> SEQ ID NO 294
<211> LENGTH: 46
<212> TYPE: PRT
<213> ORGANISM: Todarodes pacificus

<400> SEQUENCE: 294

Leu Gly Phe Gly Gly Val Leu Gly Tyr Gly Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Gly Leu Tyr Gly Gly Tyr Gly Leu Gly Gly His
        35                  40                  45
```

<210> SEQ ID NO 295
<211> LENGTH: 10
<212> TYPE: PRT
<213> ORGANISM: Todarodes pacificus

<400> SEQUENCE: 295

Val Tyr Gly Gly Tyr Gly Leu Gly Gly His
1               5                   10

<210> SEQ ID NO 296
<211> LENGTH: 33
<212> TYPE: PRT
<213> ORGANISM: Todarodes pacificus

<400> SEQUENCE: 296

Val Gly Tyr Gly Gly Tyr Gly Tyr Gly Gly Gly Leu Tyr Gly Gly His
1               5                   10                  15

Tyr Gly Gly Tyr Gly His Phe Gly Gly Val His Ser His Tyr Gly Val
            20                  25                  30

Gly

<210> SEQ ID NO 297
<211> LENGTH: 19
<212> TYPE: PRT
<213> ORGANISM: Todarodes pacificus

<400> SEQUENCE: 297

Tyr Gly Asp Val Tyr Gly Gly Leu Tyr Gly Gly Leu Tyr Gly Gly Leu
1               5                   10                  15

Leu Gly Ala

<210> SEQ ID NO 298
<211> LENGTH: 28
<212> TYPE: PRT
<213> ORGANISM: Todarodes pacificus

<400> SEQUENCE: 298

Leu Gly Tyr Gly Gly Leu Leu Gly Gly Tyr Gly Ala Leu His Gly Gly
1               5                   10                  15

Leu Tyr Gly Gly Tyr Gly Leu Gly Gly Leu His Tyr
            20                  25

<210> SEQ ID NO 299
<211> LENGTH: 199
<212> TYPE: PRT
<213> ORGANISM: artificial sequence
<220> FEATURE:
<223> OTHER INFORMATION: Recombinant protein

<400> SEQUENCE: 299

Met Thr Tyr Gly Tyr Gly Gly Leu Tyr Gly Gly Leu Tyr Gly Gly Leu
1               5                   10                  15

Gly Tyr Pro Ala Ala Ala Ser Val Ser Thr Val His His Pro Tyr Gly
            20                  25                  30

Tyr Gly Gly Leu Tyr Gly Gly Leu Tyr Gly Gly Leu Gly Tyr Pro Ala
        35                  40                  45

Ala Ala Ser Val Ser Thr Val His His Pro Tyr Gly Tyr Gly Gly Leu
    50                  55                  60

Tyr Gly Gly Leu Tyr Gly Gly Leu Gly Tyr Pro Ala Ala Ala Ser Val
65                  70                  75                  80

```
Ser Thr Val His His Pro Tyr Gly Tyr Gly Gly Leu Tyr Gly Gly Leu
                85                  90                  95

Tyr Gly Gly Leu Gly Tyr Pro Ala Ala Ala Ser Val Ser Thr Val His
            100                 105                 110

His Pro Tyr Gly Tyr Gly Gly Leu Tyr Gly Gly Leu Tyr Gly Gly Leu
        115                 120                 125

Gly Tyr Pro Ala Ala Ala Ser Val Ser Thr Val His His Pro Tyr Gly
    130                 135                 140

Tyr Gly Gly Leu Tyr Gly Gly Leu Tyr Gly Gly Leu Gly Tyr Pro Ala
145                 150                 155                 160

Ala Ala Ser Val Ser Thr Val His His Pro Tyr Gly Tyr Gly Gly Leu
                165                 170                 175

Tyr Gly Gly Leu Tyr Gly Gly Leu Gly Tyr Pro Ala Ala Ala Ser Val
            180                 185                 190

Ser Thr Val His His Pro Ser
        195
```

<210> SEQ ID NO 300
<211> LENGTH: 162
<212> TYPE: PRT
<213> ORGANISM: artificial sequence
<220> FEATURE:
<223> OTHER INFORMATION: Recombinant protein

<400> SEQUENCE: 300

```
Met Gly Thr Leu Ser Tyr Gly Tyr Gly Gly Leu Tyr Gly Gly Leu Tyr
1               5                   10                  15

Gly Gly Leu Gly Tyr Gly Pro Ala Ala Ala Ser Val Ser Thr Val His
            20                  25                  30

His Pro Ser Thr Gly Thr Leu Ser Tyr Gly Tyr Gly Gly Leu Tyr Gly
        35                  40                  45

Gly Leu Tyr Gly Gly Leu Gly Tyr Gly Pro Ala Ala Ala Ser Val Ser
    50                  55                  60

Thr Val His His Pro Ser Thr Gly Thr Leu Ser Tyr Gly Tyr Gly Gly
65                  70                  75                  80

Leu Tyr Gly Gly Leu Tyr Gly Gly Leu Gly Tyr Gly Pro Ala Ala Ala
                85                  90                  95

Ser Val Ser Thr Val His His Pro Ser Thr Gly Thr Leu Ser Tyr Gly
            100                 105                 110

Tyr Gly Gly Leu Tyr Gly Gly Leu Tyr Gly Gly Leu Gly Tyr Gly Pro
        115                 120                 125

Ala Ala Ala Ser Val Ser Thr Val His His Pro Ser Thr Gly Thr Leu
    130                 135                 140

Ser Tyr Gly Tyr Gly Gly Leu Tyr Gly Gly Leu Tyr Gly Gly Leu Gly
145                 150                 155                 160

Tyr Gly
```

<210> SEQ ID NO 301
<211> LENGTH: 268
<212> TYPE: PRT
<213> ORGANISM: artificial sequence
<220> FEATURE:
<223> OTHER INFORMATION: Recombinant protein

<400> SEQUENCE: 301

```
Met Gly Thr Leu Ser Tyr Gly Tyr Gly Gly Leu Tyr Gly Gly Leu Tyr
1               5                   10                  15
```

```
Gly Gly Leu Gly Tyr Gly Pro Ala Ala Ala Ser Val Ser Thr Val His
            20                  25                  30

His Pro Ser Thr Gly Thr Leu Ser Tyr Gly Tyr Gly Gly Leu Tyr Gly
        35                  40                  45

Gly Leu Tyr Gly Gly Leu Gly Tyr Gly Pro Ala Ala Ala Ser Val Ser
    50                  55                  60

Thr Val His His Pro Ser Thr Gly Thr Leu Ser Tyr Gly Tyr Gly Gly
65                  70                  75                  80

Leu Tyr Gly Gly Leu Tyr Gly Gly Leu Gly Tyr Gly Pro Ala Ala Ala
                85                  90                  95

Ser Val Ser Thr Val His His Pro Ser Thr Gly Thr Leu Ser Tyr Gly
            100                 105                 110

Tyr Gly Gly Leu Tyr Gly Gly Leu Tyr Gly Gly Leu Gly Tyr Gly Pro
        115                 120                 125

Ala Ala Ala Ser Val Ser Thr Val His His Pro Ser Thr Gly Thr Leu
    130                 135                 140

Ser Tyr Gly Tyr Gly Gly Leu Tyr Gly Gly Leu Tyr Gly Gly Leu Gly
145                 150                 155                 160

Tyr Gly Pro Ala Ala Ala Ser Val Ser Thr Val His His Pro Ser Thr
                165                 170                 175

Gly Thr Leu Ser Tyr Gly Tyr Gly Gly Leu Tyr Gly Gly Leu Tyr Gly
            180                 185                 190

Gly Leu Gly Tyr Gly Pro Ala Ala Ala Ser Val Ser Thr Val His His
        195                 200                 205

Pro Ser Thr Gly Thr Leu Ser Tyr Gly Tyr Gly Gly Leu Tyr Gly Gly
    210                 215                 220

Leu Tyr Gly Gly Leu Gly Tyr Gly Pro Ala Ala Ala Ser Val Ser Thr
225                 230                 235                 240

Val His His Pro Ser Thr Gly Thr Leu Ser Tyr Gly Tyr Gly Gly Leu
                245                 250                 255

Tyr Gly Gly Leu Tyr Gly Gly Leu Gly Tyr Gly Pro
            260                 265
```

<210> SEQ ID NO 302
<211> LENGTH: 443
<212> TYPE: PRT
<213> ORGANISM: artificial sequence
<220> FEATURE:
<223> OTHER INFORMATION: Recombinant protein

<400> SEQUENCE: 302

```
Met Gly Thr Leu Ser Tyr Gly Tyr Gly Gly Leu Tyr Gly Gly Leu Tyr
1               5                   10                  15

Gly Gly Leu Gly Tyr Gly Pro Ala Ala Ala Ser Val Ser Thr Val His
            20                  25                  30

His Pro Ser Thr Gly Thr Leu Ser Tyr Gly Tyr Gly Gly Leu Tyr Gly
        35                  40                  45

Gly Leu Tyr Gly Gly Leu Gly Tyr Gly Pro Ala Ala Ala Ser Val Ser
    50                  55                  60

Thr Val His His Pro Ser Thr Gly Thr Leu Ser Tyr Gly Tyr Gly Gly
65                  70                  75                  80

Leu Tyr Gly Gly Leu Tyr Gly Gly Leu Gly Tyr Gly Pro Ala Ala Ala
                85                  90                  95

Ser Val Ser Thr Val His His Pro Ser Thr Gly Thr Leu Ser Tyr Gly
            100                 105                 110
```

```
Tyr Gly Gly Leu Tyr Gly Gly Leu Tyr Gly Gly Leu Gly Tyr Gly Pro
        115                 120                 125

Ala Ala Ala Ser Val Ser Thr Val His His Pro Ser Thr Gly Thr Leu
    130                 135                 140

Ser Tyr Gly Tyr Gly Gly Leu Tyr Gly Gly Leu Tyr Gly Gly Leu Gly
145                 150                 155                 160

Tyr Gly Pro Ala Ala Ala Ser Val Ser Thr Val His His Pro Ser Thr
                165                 170                 175

Gly Thr Leu Ser Tyr Gly Tyr Gly Gly Leu Tyr Gly Gly Leu Tyr Gly
            180                 185                 190

Gly Leu Gly Tyr Gly Pro Ala Ala Ala Ser Val Ser Thr Val His His
        195                 200                 205

Pro Ser Thr Gly Thr Leu Ser Tyr Gly Tyr Gly Gly Leu Tyr Gly Gly
    210                 215                 220

Leu Tyr Gly Gly Leu Gly Tyr Gly Pro Ala Ala Ala Ser Val Ser Thr
225                 230                 235                 240

Val His His Pro Ser Thr Gly Thr Leu Ser Tyr Gly Tyr Gly Gly Leu
                245                 250                 255

Tyr Gly Gly Leu Tyr Gly Gly Leu Gly Tyr Gly Pro Ala Ala Ala Ser
            260                 265                 270

Val Ser Thr Val His His Pro Ser Thr Gly Thr Leu Ser Tyr Gly Tyr
        275                 280                 285

Gly Gly Leu Tyr Gly Gly Leu Tyr Gly Gly Leu Gly Tyr Gly Pro Ala
    290                 295                 300

Ala Ala Ser Val Ser Thr Val His His Pro Ser Thr Gly Thr Leu Ser
305                 310                 315                 320

Tyr Gly Tyr Gly Gly Leu Tyr Gly Gly Leu Tyr Gly Gly Leu Gly Tyr
                325                 330                 335

Gly Pro Ala Ala Ala Ser Val Ser Thr Val His His Pro Ser Thr Gly
            340                 345                 350

Thr Leu Ser Tyr Gly Tyr Gly Gly Leu Tyr Gly Gly Leu Tyr Gly Gly
        355                 360                 365

Leu Gly Tyr Gly Pro Ala Ala Ala Ser Val Ser Thr Val His His Pro
    370                 375                 380

Ser Thr Gly Thr Leu Ser Tyr Gly Tyr Gly Gly Leu Tyr Gly Gly Leu
385                 390                 395                 400

Tyr Gly Gly Leu Gly Tyr Gly Pro Ala Ala Ala Ser Val Ser Thr Val
                405                 410                 415

His His Pro Ser Thr Gly Thr Leu Ser Tyr Gly Tyr Gly Gly Leu Tyr
            420                 425                 430

Gly Gly Leu Tyr Gly Gly Leu Gly Tyr Gly Pro
        435                 440


<210> SEQ ID NO 303
<211> LENGTH: 195
<212> TYPE: PRT
<213> ORGANISM: Loligo vulgaris

<400> SEQUENCE: 303

Met Ala Ala Lys Leu Ile Thr Leu Leu Ala Val Ile Ala Leu Ser Asn
1               5                   10                  15

Tyr Ala Tyr Ala Leu Leu Pro Gly Leu Leu Gly Gly Tyr Gly Tyr Pro
            20                  25                  30

Ala Ala Thr Thr Tyr Arg Gln Thr Thr His His Gly Tyr Gly Gly Leu
```

-continued

```
        35                  40                  45

Tyr Gly Gly Leu Gly Tyr His Tyr Pro Ala Ala Thr Ala Val Ser His
    50                  55                  60

Thr Thr His His Ala Pro Tyr Gly Tyr Gly Gly Leu Tyr Gly Gly Leu
65                  70                  75                  80

Tyr Gly Gly Leu Gly Tyr Pro Ala Ala Ala Ser Val Ser Thr Val His
                85                  90                  95

His Pro Val Gly Tyr Gly Gly Tyr Gly Leu Gly Ala Tyr Gly Ala Tyr
            100                 105                 110

Gly Leu Gly Tyr Gly Leu His Tyr Pro Ala Ala Thr Ala Val Ser His
        115                 120                 125

Thr Thr His His Ala Pro Tyr Gly Tyr Gly Gly Leu Tyr Gly Gly Leu
    130                 135                 140

Tyr Gly Gly Leu Gly Ala Val Ser Thr Val Ser His Gly Leu Gly Tyr
145                 150                 155                 160

Gly Leu His His Pro Val Gly Tyr Ala Gly Tyr Gly Leu Gly Ala Thr
                165                 170                 175

Ala Val Ser His Thr Thr His His Ala Pro Tyr Gly Gly Phe Gly Tyr
            180                 185                 190

Gly Leu Tyr
        195


<210> SEQ ID NO 304
<211> LENGTH: 28
<212> TYPE: PRT
<213> ORGANISM: Loligo vulgaris

<400> SEQUENCE: 304

Tyr Gly Tyr Gly Gly Leu Tyr Gly Gly Leu Tyr Gly Gly Leu Gly Tyr
1               5                   10                  15

Pro Ala Ala Ala Ser Val Ser Thr Val His His Pro
            20                  25
```

DE NOVO STRUCTURAL PROTEIN DESIGN FOR MANUFACTURING HIGH STRENGTH MATERIALS

CROSS REFERENCE TO RELATED APPLICATION

This application claims priority to U.S. provisional patent application No. 62/152,437, filed Apr. 24, 2015, the disclosure of which is incorporated herein by reference.

STATEMENT REGARDING FEDERALLY SPONSORED RESEARCH

This invention was made with government support under Contract No. N00014-13-1-0595, awarded by the Office of Naval Research and Contract No. W911NF-16-1-0019, awarded by the Army Research Office. The Government has certain rights in the invention.

FIELD OF THE DISCLOSURE

The present disclosure relates generally to compositions and methods for designing and using high strength tunable protein-based materials.

BACKGROUND OF THE DISCLOSURE

Several attempts to commercialize recombinant biological fibers in the last two decades have failed, due to reliance on solution-based methods for production, which degrade their natural mechanical properties. This represents the biggest obstacle when trying to commercialize strong, pliable, and durable materials from biological fibers. There is accordingly an ongoing and unmet need for improved methods for designing protein-based materials, and for new protein-based materials that are modifications of naturally occurring biological proteins such that they have improved material properties. The present disclosure meets this need.

SUMMARY OF THE DISCLOSURE

The present disclosure provides a polypeptide comprising alternating repeats of crystallite-forming subsequences and amorphous subsequences. The polypeptide can be a supramolecular polypeptide exhibiting self-healing behavior. The crystallite-forming subsequences form crystallites comprising stacks of one or more β-sheets and the amorphous subsequences form a network of hydrogen bonds. The supramolecular polypeptides can exhibit crystallinity from 0% and 60%.

The disclosure provides compositions comprising a plurality of synthetic polypeptides comprising alternating repeats of crystallite-forming subsequences and amorphous subsequences, wherein the crystallite-forming subsequences form crystallites comprising stacks of one or more β-sheets and the amorphous subsequences form a network of hydrogen bonds. The polypeptides can be present in a suitable carrier such as a buffer. The plurality of polypeptides in a composition can be the same or can be distinct.

The present disclosure provides a method of making a synthetic or recombinant supramolecular polypeptide comprising crystallite-forming subsequences and amorphous subsequences. The method comprises selecting an amino acid sequence that is capable of forming the crystallite-forming subsequence, wherein the crystallite-forming subsequence is from about 2 nm to about 5 nm long, and selecting an amino acid sequence that is capable of forming amorphous subsequence which can have 10 to 60 amino acids, and forming the synthetic polypeptide by incorporating the amino acid sequence that is capable of forming the crystallite-forming subsequence and the sequence that is capable of forming the amorphous subsequence into the synthetic or recombinant polypeptide.

DETAILED DESCRIPTION

Figure 1:
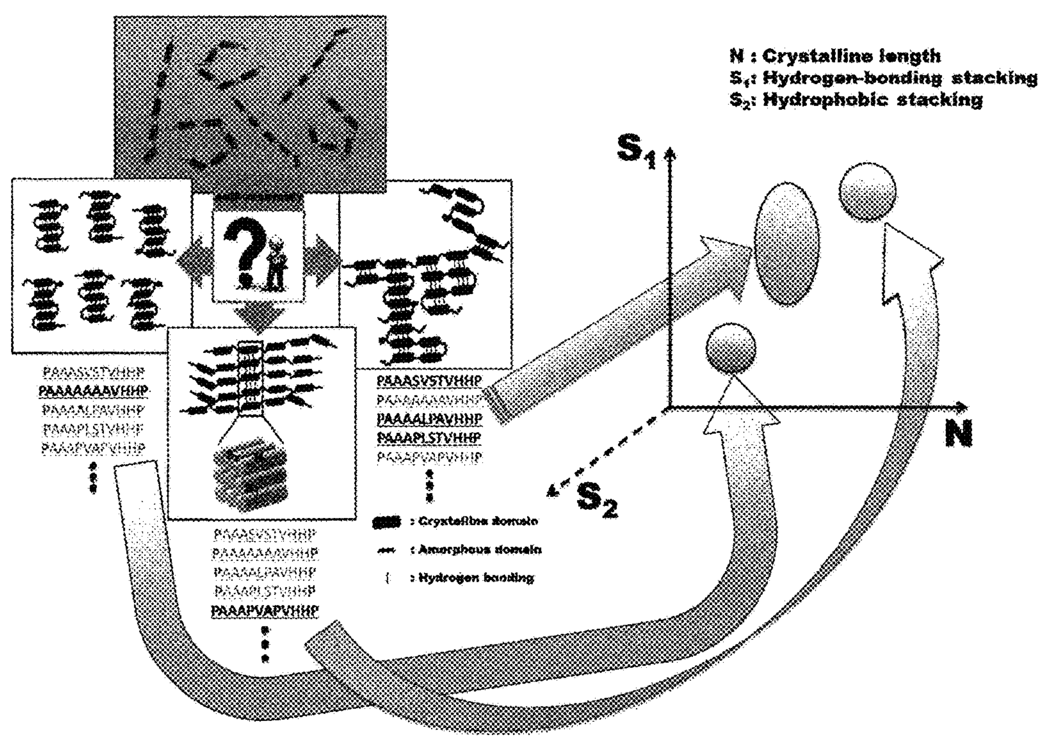
FIG. 1: Mapping of protein sequences to ordered structures for structural proteins. Amino acid modifications in ordered domains will affect intermolecular and intramolecular stacking of β-sheet formation. The amino acid sequences shown are: PAAAAAAAVHHP (SEQ ID NO:303), PAAAPVAPVHHP (SEQ ID NO:304); PAAASVSTVHHP (SEQ ID NO:305); PAAAALPAVHHP (SEQ ID NO:306); (SEQ ID NO:307) PAAAPLSTVHHP.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all polynucleotide and amino acid sequences described herein. Each RNA sequence includes its DNA equivalent, and each DNA sequence includes its RNA equivalent. Complementary and anti-parallel polynucleotide sequences are included. Every polypeptide disclosed herein includes every polynucleotide sequence that encodes the polypeptides.

The present disclosure provides compositions and methods, aspects of which relate to a new approach to elucidating the relationship between the protein sequence-structure of self-aggregating proteins. In particular embodiments, the disclosure includes methods for making polypeptides, the amino acid sequences of which are based in part on naturally occurring proteins, but have been modified such that the polypeptides have distinct properties relative to their naturally occurring counterparts. The disclosure includes compositions comprising homogenous polypeptide populations, meaning all the polypeptides in the composition share the same primary amino acid sequence, and also includes heterogeneous polypeptide populations, meaning the compositions comprise combinations of distinct polypeptides with different primary amino acid sequences. In embodiments, polypeptides provided by this disclosure differ from their natural counterparts by at least one property, such as having a distinct primary amino acid sequence, and/or a distinct modulus value. In embodiments, the modulus value that differs from a naturally occurring counterpart is a tensile modulus, an elastic modulus, a bulk modulus, or a shear modulus. In embodiments, polypeptides of this disclosure are made such that they comprise ordered and disordered domains which contribute favorably to their mechanical properties. In particular, an aspect of this disclosure relates to the production and screening of random protein libraries having member polypeptides that are modifications of naturally occurring proteins. By screening such libraries, those polypeptides with desirable properties that are related to the size and distribution of their crystalline and amorphous regions can be generated, identified, modified further if desired, and produced recombinantly. In embodiments, modifying the proteins, such as to produce a library for screening, comprises varying length of amino acid content in beta-sheet crystalline/ordered regions, or varying the length of Gly-rich amorphous region (e.g. segmented copolymer morphology depends on volume fractions), or varying the size of the repeating unit (amorphous+crystalline, "n") to modulate the molecular weight of the protein, or combinations thereof. In embodiments, the modifications comprise altering a crystal-forming polypeptide sequence (also referred to herein as the crystallite-forming subsequence or crystalline sequence or crystal domain) so that the wild-type amino acid is replaced with A, S, T, V, L, or P.

In embodiments, screening polypeptides comprises expressing the polypeptides recombinantly in a prokaryotic expression system, such as *E. coli*, selecting separate cultures each expressing distinct polypeptides, placing a plurality of samples of the cultures in separate sample test chambers, and subjecting the samples to a means of identifying protein structure in the samples, such as by chromatography, calorimetry, mass spectroscopy, IR or Raman spectroscopy, microscopy and X-Ray Diffraction (XRD), to obtain information on the protein structure, such as backbone and h-bond directions. It will be recognized that this approach is readily adaptable to high-throughput techniques. Once the protein information is obtained and analyzed, the stock clones can be grown, and the proteins likely to have desirable properties can be produced recombinantly and used for a variety of purposes, and/or for further characterized and optimization. Thus in one approach, the present disclosure comprises providing a template protein, generating a plurality of modified versions of the template protein, screening the plurality of modified polypeptides for crystalline and amorphous regions, selecting modified polypeptides with crystalline and amorphous sequences that are likely to impart desirable mechanical properties to the polypeptides, and producing the selected polypeptides recombinantly. Proteins produced according to this approach are included.

Also included in this disclosure are all amino acid sequences provided herewith, all polynucleotide sequences encoding the amino acid sequences, expression vectors encoding the polypeptide sequences, cells comprising the expression vectors, cells and cell cultures comprising the proteins expressed by the expression vectors, and cell media containing or separated from such cell cultures.

The disclosure includes the proteins designed and/or selected according to the present disclosure, compositions comprising the proteins, and methods of using the proteins.

In certain approaches the disclosure includes a database comprising at least one of the crystal-domain amino acid sequences (also referred to herein as crystallite-forming subsequences), and/or at least one of the amorphous-domain amino acid sequences (also referred to herein as amorphous subsequences), provided herein. Amino acid sequences capable of forming crystal domains and amorphous domains are provided. The database may be searchable, and may be configured to be searchable based on an input query, such as a query designed to identify and/or generate amino acid sequences that are capable of forming crystal-domains, amorphous-domains, and combinations thereof. The database can be configured to be searchable for one or more amino acid sequences for incorporating into a polypeptide or a population of polypeptides based on inputting any desirable properties, including but not necessarily limited to the physical length of the domains that are capable of forming. The database may be a component of a system in which the database is stored on a storage device in communication with a processor. The storage device can comprise any suitable storage medium, including but not necessarily limited to digital files, and may provide access to cloud-based files, etc. The system can include a computer program comprising an algorithm to facilitate database searching. The computer program may be configured to identify, retrieve and/or generate one or more polypeptide sequences that comprise a motif pattern of, for example, $(ca)_n$, $(ac)_n$, $a(ca)_n$, or $(ca)_n c$, wherein c is a crystal-forming domain block and a is an amorphous domain block, and n is the tandem-repeat number, and is an integer from 1 to 100, inclusive, and including all ranges of integers there between.

In another approach the disclosure includes a method of making a synthetic or recombinant polypeptide. A synthetic polypeptide is made without cell based translation systems. A recombinant polypeptide is made using cell based translation systems. The polypeptide contains segments capable of forming at least a first crystal-forming domain block and at least a first amorphous domain block. The method comprises selecting an amino acid sequence that is capable of forming the first crystal domain block, wherein the crystal domain block is from about 2 nm to about 5 nm long and comprises from 10 to 30 amino acids, and selecting an amino acid sequence that is capable of forming a first amorphous domain block, wherein the first amorphous domain block can comprise from 10 to 60 amino acids, and forming the synthetic polypeptide by incorporating the amino acid sequence that is capable of forming the first crystal-forming domain block and the sequence that is capable of forming the second amorphous domain block into the synthetic or recombinant polypeptide. Embodiments further comprise incorporating at least a second crystal-forming domain block, or at least a second amorphous domain block, or a combination thereof, into the single polypeptide. In certain approaches the method includes incorporating into the polypeptide: i) the first and second crystal-forming domain blocks each comprising the same amino acid sequence as each other; or ii) the first and second crystal-forming domain blocks each comprising distinct amino acid sequences from each other; or iii) the first and second amorphous domain blocks each comprising the same amino acid sequence as each other; or iv); the first and second amorphous domain blocks each comprising distinct amino acid sequences from each other. Those skilled in the art will recognize that additional domain blocks can be included according to the aforementioned $(ca)_n$, $(ac)_n$, $a(ca)_n$, or $(ca)_n c$ configuration. Blocks may also be referred to as subsequences.

In embodiments, selecting the amino acid sequence that is capable of forming the first crystallite-forming subsequence, and/or selecting the amino acid sequence that is capable of forming the first amorphous subsequence, or a combination thereof, comprises selecting an amino acid sequence from a database of amino acid sequences that comprise at least one sequence that comprises or consists of a sequence selected from the sequences in Table 5 and/or Table 6, and includes selecting sequences wherein between 1 and 4 amino acids in those sequences are altered, or wherein those sequences include an insertion or a deletion.

In non-limiting embodiments, the proteins of this disclosure are processed to form any of a variety of three-dimensional shapes/articles of manufacture, including but not necessarily limited to ribbons, lithographic patterns, and nano-scale objects such as nanotube arrays. In embodiments, the proteins are processed by, for example, heating to form a rubbery materials, and processing the rubber, including cooling the rubber, so that it forms a product, such as the three-dimensional article of manufacture. A "rubber" as the term is used herein does not refer to a phase transition, i.e., from solid to liquid. A "rubber" instead refers to a glass transition, which is not a physical thermodynamic phase transition. The glass transition is the change from one condensed state (glass) to another condensed state (rubber). The rubbery material is achieved at least in part by subjecting the protein to a heat treatment and pressure that facilitates the glass transition. In embodiments the product retains the capability of reversible transition to a rubber. In embodiments the disclosure includes making a product by extruding the protein rubber, electrospinning the protein rubber, coating the protein rubber onto a surface, molding the protein rubber, forming an adhesive layer, forming a film, fiber, ribbon or tube, and forming a film, such as forming a film on patterned surface. In embodiments, the protein is processed in a form such as a hot-melt, and in injection molded into a suitable mold. In various embodiments, the compositions of can include additives, such as a plasticizer. In embodiments, the disclosure includes forming powder comprising or consisting of a polypeptide by dissolving the polypeptide in a polar solvent and casting via the evaporation of the polar solvent.

Non-limiting embodiments of the present disclosure are illustrated using an anatomical feature of squid that is referred to in the art as Squid Ring Teeth (SRT). However, it will be recognized by those skilled in the art that any other naturally occurring protein that has desirable properties such that they are candidates for analysis and modification according to this disclosure can also be used. Such proteins include but are not necessarily limited to silks and other boil-elastomers.

As discussed above, the present disclosure provides polypeptides comprising at least two repeats of crystallite-forming subsequences and an amorphous subsequence. The amorphous subsequence is located between the crystallite-forming subsequences. The polypeptide can comprise a plurality of alternating crystallite-forming subsequences and amorphous subsequences. The polypeptide can also comprise other sequences—such as sequences derived from cloning. The sequences derived from cloning may be present as repeats. Although the amorphous subsequences are intervening between crystallite-forming subsequences, they do not necessarily need to be between two crystallite-forming subsequences. For example, an amorphous subsequence can flank a crystallite-forming subsequence at one end (C or N terminal) only. The length and makeup of crystallite-forming subsequences is such that it can provide hydrogen bonding with another crystallite-forming subsequence within the same polypeptide to result in ordered structures (such as beta sheet structures). The beta sheet structures can be stacked. The intervening amorphous subsequences provide flexibility between the crystallite-forming subsequences in the form of turns so that crystallite forming subsequences can be in close proximity with each other so as to be able to form hydrogen bonds—resulting in ordered structures. The resultant polypeptide can have semi-crystalline properties.

The amorphous subsequence allows the formation of a network of hydrogen bonds—within the same amorphous subsequence or with different amorphous subsequences. The ordered stacked beta sheet formations of the crystallite-forming subsequences and the network of hydrogen bonding of the amorphous subsequences provides for a supramolecular structure of the polypeptide. The supramolecular polypeptides exhibit self-healing properties. These molecules can recover their structural and functional properties following disruption. This is attributable, at least in part, to the network of hydrogen bonding of the amorphous subsequences.

The crystallite-forming and amorphous subsequences contribute to the mechanical properties of the polypeptide. The crystalline index of the polypeptide can be from 0 to 60%. For example, the crystalline index of the polypeptide can be from 1 to 60% (including all percentage values therebetween). In one embodiment, the crystalline index is from 30 to 50%. It will be recognized that the crystalline index is related to the sequence as well as the physical or chemical process. For the present polypeptides, for a given sequence, the crystalline index was not found to change significantly with molecular weight under similar conditions. For example, the crystalline index for exemplary polypeptides syn-n4, syn-n7 and syn-n11 was observed to be from 40 to 45%.

Figure 3:
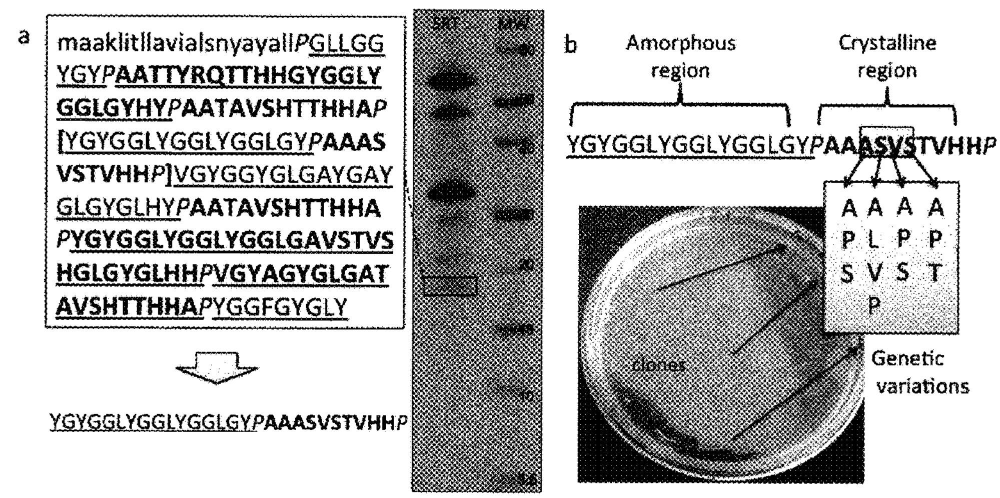
FIG. 3: (a) Segmented copolymer architecture of the protein sequence is marked as signal sequence: lower case, prolines: italics, amorphous: underlined, crystalline: bold, amorphous/crystalline: underlined and bold. The SDS-Page (middle) shows sizes of native SRT proteins. The 195 amino acid sequence is SEQ ID NO:303. The sequence YGYGGLYGGLYGGLGYPAAASVSTVHHP is SEQ ID NO:304. (b) The library is prepared based on the protein template of 18 kDa native sequence. (c) Tandem repeat construction strategy to control the length of synthetic protein. (d) Example of tandem repeat construction of N=13 with DNA and SDS-page gels.
Figure 3:
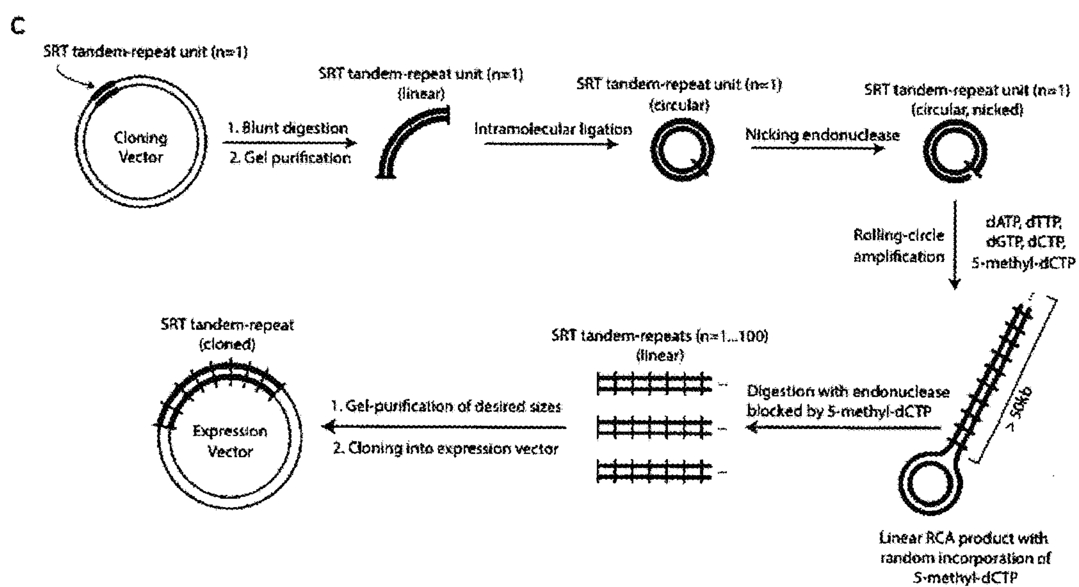
Figure 3:
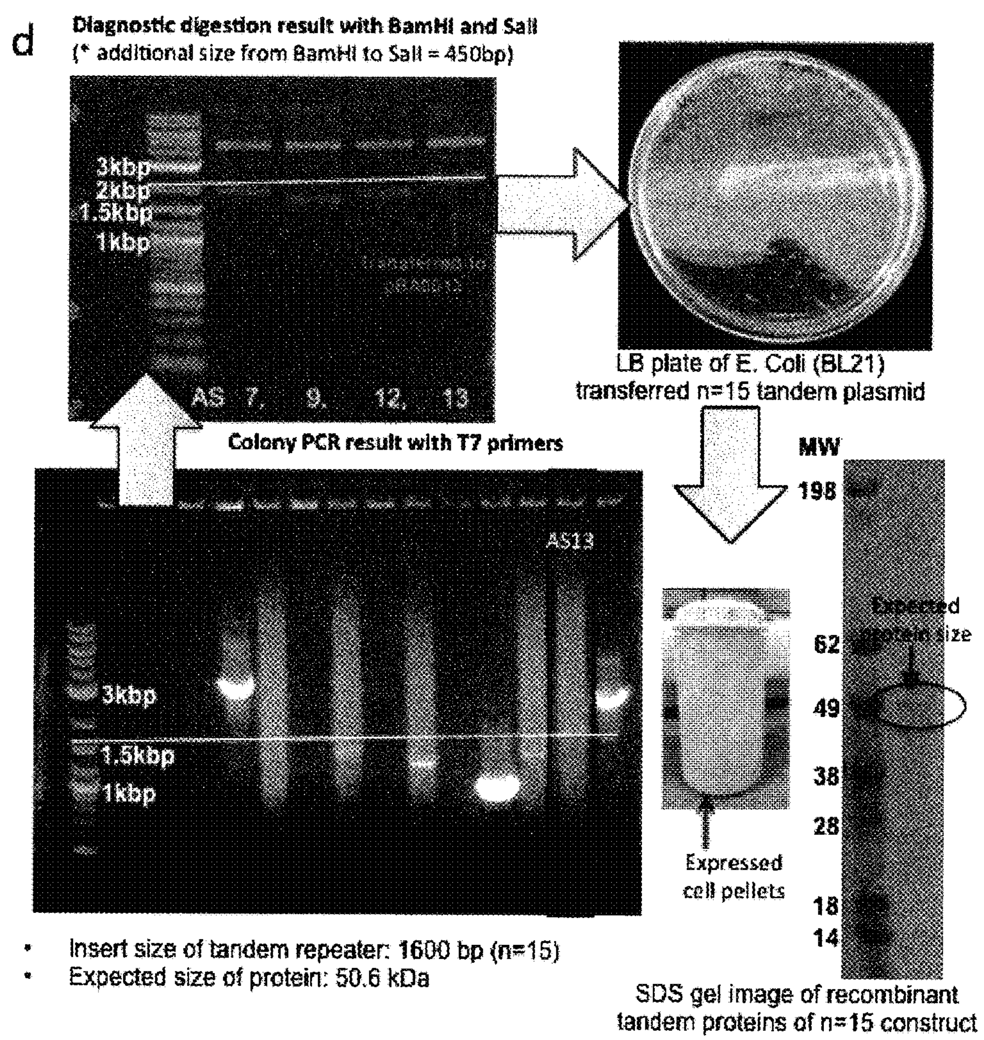

The crystallite-forming subsequence can be from about 2 nm to about 5 nm. This roughly corresponds to 10 to 30 amino acids. Thus, the crystallite-forming subsequence can have from 10 to 30 amino acids. For example, the crystallite-forming subsequence can have from 15 to 25 amino acids. Generally, amino acids that are known to be capable of participating in hydrogen bonding leading to ordered structures like beta sheet formation are preferred. Such amino acids include histidine, threonine, valine, alanine, serine and the like. An example of a crystallite-forming subsequence is shown in FIG. 3*b*, where the sequence is AA[XXXXXX] HH. The bracketed portion can comprise a variable AVSHT sequence. The variable sequence can be AASHT AAAHT, AAAAT, AAAAA and the like. The length of the bracketed portion is variable.

The amorphous subsequence is a glycine-rich sequence. The amorphous subsequence can assume different conformations. For example, it can be present as a random coil, a helix, or as a psi chain. It can comprise from 10 to 60 amino acids. For example, it can comprises from 10 to 56 amino acids. In addition to contributing to mechanical and other properties of the polypeptide, the amorphous subsequence also serve to connect the crystallite-forming subsequences.

The present polypeptides can have various arrangements of the crystallite-forming subsequences (c) and the amorphous subsequences (a). For example, the present disclosure provides polypeptides and methods of making a polypeptide sequence of the form $(ca)_n$, $(ac)_n$, $a(ca)_n$, or $(ca)_nc$, wherein c is a crystallite-forming subsequence and a is an amorphous subsequence, and n is the tandem-repeat number, is an integer from 1 to 100, inclusive, and including all ranges of integers there between. For example, it can have from 4 to 20 repeats (including all integer values therebetween). The crystallite-forming subsequence can be derived from a naturally occurring bio-elastomer, such as SRT, and the amorphous subsequence can be derived from a naturally occurring bio-elastomer protein. In embodiments, compositions comprising a polypeptide comprising a sequence of the form $(ca)_n$, $(ac)_n$, $a(ca)_n$, or $(ca)_nc$, where c is a crystallite-forming subsequence, a is an amorphous subsequence derived from a bio-elastomer protein, and n, the tandem-repeat number, is an integer from 1 to 100, inclusive, and including all ranges of integers there between. $(ca)_n$, $(ac)_n$, $a(ca)_n$, or $(ca)_nc$ can be similar or identical to a block (e.g. Repeating units are same) or segmented (e.g. Repeating units are different) polymer or co-polymer.

In one embodiment, the crystallite-forming subsequence c contains one or more amino acid substitutions in which the wild-type amino acid is replaced with one of the following amino acids: A, S, T, V, L, P. The disclosure includes combinations of such substitutions.

In one embodiment, the crystallite-forming subsequence and the amorphous subsequence are derived from SRT proteins from any of the following species: *Loligo vulgaris, Loligo pealei, Todarodes pacificus, Euprymna scolopes.*

In embodiments, the crystallite-forming subsequence c exhibits at least 50%, and up to 100% sequence identity, inclusive and including all integers and ranges there between, to a sequence identity to a sequence from Table 5, and/or the amorphous subsequence a exhibits at least 50% sequence identity, and up to 100% sequence inclusive and including all integers and ranges there between, identity to a sequence from Table 6 that contains Glycine rich sequences. Alternatively amorphous subsequences could be engineered synthetically based on amorphous known repeating structural domains such as beta-spiral $[GPGXX]_n$, linker $[GP(S,Y,G)]_n$ or $3_{10}$-helix $[GGX]_n$, or any combinatorial combination of these units, where n, is an integer from 1 to 100, inclusive, and including all ranges of integers there between, and X is typically A, S, V, T, Y amino acids or any combinatorial combination of these amino acids.

In embodiments, one or more polypeptides of this disclosure are formed into a powder, such as by dissolving the polypeptides in a polar solvent and casting via the evaporation of the polar solvent. In embodiments, polypeptide powder is formed or modified by heating to between 32° C. and 195° C. inclusive, and including all integers and ranges therebetween, and subjecting to a pressure treatment, such as a pressure treatment between 1 kPa and 1 GPa, inclusive and including all integers and ranges therebetween. In embodiments, a plasticizer is included in the process. Suitable plasticizer include, but are not limited to, water, glycerol, 1,4-Butanediol, Dibutyl tartrate, Dibutyl phthalate, Lactic acid, Octanoic acid, Plamitic acid, Sorbitol, Sucrose, and diacetyl tartaric acid ester of monodiglycerides (DATEM).

In embodiments, the disclosure includes processing polypeptides of the disclosure or compositions comprising them by forming an adhesive, self-healing, or cohesive layer techniques. In embodiments, the disclosure comprises forming a film, fiber, ribbon, colloid, capsule, ribbon or tube.

In illustrative and non-limiting embodiments, the disclosure provides synthetic peptide sequences built based on de novo design of thermoplastic SRT proteins. SRT proteins have amorphous and ordered domains. Based on preexisting SRT ordered templates, our approach generates new protein sequences, which directly correlate to crystal properties (FIG. 1). The approach is adaptable to other proteins and can be used accordingly by those skilled in the art, given the benefit of the present disclosure.

The following specific examples are provided to illustrate the invention, but are not intended to be limiting in any way.

Example 1

SRT proteins from *Loligo vulgaris* were identified using a next generation sequencing approach and transcriptome assembly (FIG. 3*a*). A segmented block is selected for tandem repeat construction strategy (FIG. 3*b*). Randomized gene libraries based on the block segment were designed and implemented as a combinatorial plasmid library by PCR and ligation. FIG. 3*c* shows the amplification strategy for producing tandem repeats the desired length, N, of the library members (e.g., DNA and protein gels for N=13 are shown in FIG. 3*d*). A description of a combinatorial library of crystalline-region variants is given below for the polypeptide termed SynE3.

Example 2

Tunable mechanical properties are one of the key challenges for product development. Protein-based materials modified according to the present disclosure provide a solution to this problem due to the ease of molecular scale engineering. In fact, it is known that the toughness of semi-crystalline proteins increases with respect to number of β-sheets. Notably, fibrous proteins (e.g., silk and SRT proteins) contain hard and brittle crystalline domains and amorphous flexible regions. Each of these functional regions is assembled via hydrogen bonds and van der Waals forces. The backbones of these repeating units neatly align by forming a dense hydrogen bond network, resulting in two-dimensional β-sheets. Multiple β-sheets, in turn align in parallel to form a three dimensional stack of a few nanometers in size. Here, the hydrophobic forces play a major role by keeping the β-sheets together. Native SRT proteins already show considerable diversity (variable AVSTH-rich) in their crystal-forming sequences, and their physical properties vary significantly.

We designed new sequences based on three parameters:

(i) varying length of amino acid content in beta-sheet crystalline/ordered regions (ii) varying the length of Gly-rich amorphous region (e.g. segmented copolymer morphology depends on volume fraction), and (iii) varying the size of the repeating unit (amorphous+crystalline, "n") to modulate the molecular weight of the protein.

Thermoplastic processes, used in the plastic industry, are preferred because drying steps could be eliminated; thus reducing their process time. Utilization of extrusion and injection-molding technologies offer the advantages of low cost and versatile production systems. We demonstrated the thermal processing of high-strength recombinant SRT proteins via extrusion, injection molding and hot-press processing. Water is a plasticizer for the recombinant SRT protein. The extrusion process is performed with protein powder. Glass transition temperature for the recombinant protein is 32° C. when the sample is immersed in water (e.g., saturated water content of 24%). Extruded SRT shows an elastic modulus of ~0.4 GPa at room temperature but they are highly brittle and the decrease in the modulus is most likely due to cracks formed during the cooling process at RT. The DMA was repeated after hot-press cycles with increased dynamic elastic modulus to 2 GPa. Unique to SRT, the stiffness value is preserved in both wet and dry conditions even after multiple recycles of the protein. In contrast, other high modulus bioelastomers such as recombinant silk have drastic drops in their elastic moduli for wet conditions due to the swelling and relaxation of non-crystalline domains. The overall strength of intermolecular interactions and their relative intermolecular ordering in SRT give rise to a high-strength material. The shear modulus of a protein network can be calculated as $G=\nu k T$, with a contribution of kT per strand. Estimating 2 strands per molecule gives a strand density of $\nu=0.033\text{-}0.044$ strands $nm^{-3}$, the shear modulus is calculated as $G=\nu kT=1.55\text{-}2.06\times10^5$ Pa, which agrees with the experimental data. This result is significant for thermal processing of recombinant SRT proteins compared to silk, which is very hard (~2 GPa) above its glass transition temperature.

It has been shown that mechanical properties of semi-crystalline proteins changes with respect to size of β-sheets. Using the results of previous work for synthetic spider silk analogs as well as modeling, we can measure the mechanical and rheological properties of selected clones as a function of temperature (i.e., 20° C. to 250° C.) and humidity (i.e., 0-100%).

Example 3

In this example, we developed an alternative tandem-repeat DNA-assembly method to: (i) produce TR sequences of various lengths in a single reaction, (ii) offer better control over the resulting lengths, and (iii) allow pooled processing of unit-sequence libraries. In this approach, long TR products from a short sequence unit are produced by rolling-circle amplification (RCA). The RCA reaction is tuned to incorporate noncanonical nucleotides at random positions. These nucleotides block digestion by key restriction endonucleases; the resulting partial-digestion products can be separated by size and cloned into an expression vector for protein production. This method, which we call "protected digestion of rolling-circle amplicons" (PD-RCA), can be used to prepare a library of TR sequences with a controlled distribution of lengths in a single cloning step.

We applied PD-RCA and recombinant expression in *E. coli* to produce a panel of artificial SRT-based proteins that vary only in the repeat number, but not in the lengths or compositions of their crystalline and amorphous regions. We demonstrate that the toughness and flexibility of these synthetic SRT-mimics increase as a function of molecular weight while the elastic modulus and yield strength remain unchanged. These results suggest that artificial proteins produced by PD-RCA can help to illuminate the genetic basis of protein material behavior, and that SRT proteins provide a promising platform for the design of new materials with custom properties.

Results and Discussions

Figure 4:
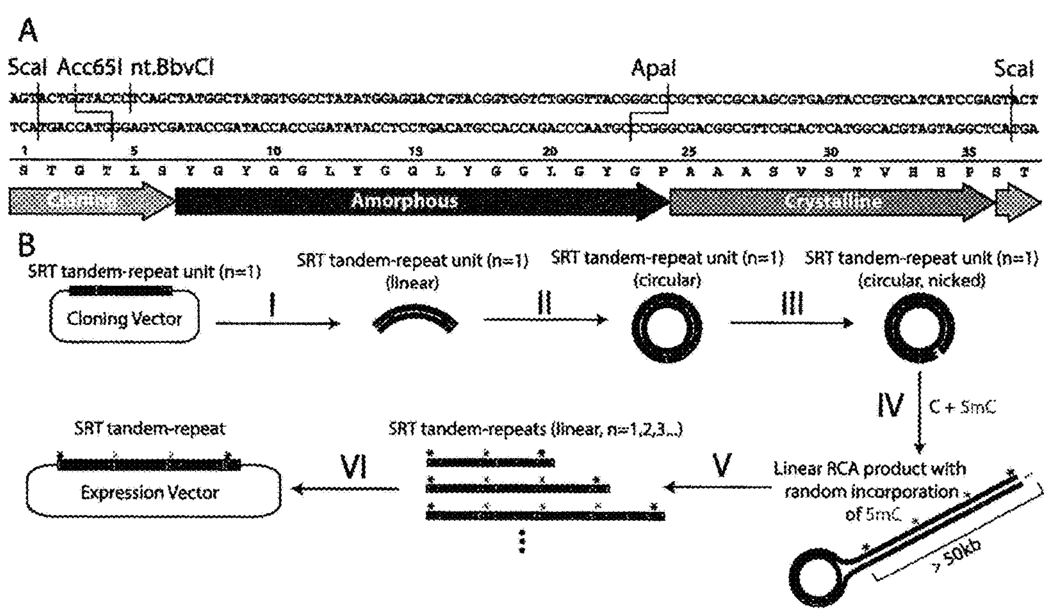
FIG. 4. Tandem-repeat (TR) construction strategy to control the length of synthetic SRT proteins. (A) DNA and protein sequence of the tandem-repeat unit (n=1). Restriction sites introduced for DNA manipulation are indicated. Protein sequence is STGTLSYGYGGLYGGLYGGLGYGPAAASVSTVHHPST (SEQ ID NO:308). The top strand DNA sequence is AGTACTGGTACCCTCAGCTATGGCTATGGTGGCCTATATGGAGGACTGTACGGTGGT CTGGGTTACGGGCCCGCTGCCGCAAGCGTGAGTACCGTGCATCATCCGAGTACT (SEQ ID NO:309) and the bottom strand is GGATATACCTCCTGACATGCCACCAGACCCAATGCCCGGGCGACGGCGTTCGCACT CATGGCACGTAGTAAGGCTCATGA (SEQ ID NO:310; given in the 5'-3' direction). (B) The tandem-repeat procedure. I: The TR unit is removed from its vector by digestion and gel purification. II: The TR unit is circularized by intramolecular ligation. III: The circular unit is nicked to create a priming site for rolling-circle amplification (RCA). IV: RCA in the presence of standard dNTPs plus 5-methyl dCTP causes 5-methylcytosine to be incorporated into the RCA product at random cytosine positions. V: Digestion of the RCA product with restriction enzymes that are blocked by 5-methylcytosine yields TR products with a distribution of different lengths. VI: The mixture of TR products is separated on a gel; the size range of interest is gel-purified and cloned into an expression vector.

In this example, we used crystal-forming polypeptide sequence PAAASVSTVHHP (SEQ ID NO:29) and the amorphous polypeptide sequence YGYGGLYGGLYGGLGY (FIG. 4A; SEQ ID NO:182). This unit is one of several possible consensus sequences derived by inspection of the alignments from squid species. We used this unit to construct three TR sequences that differ only by their repeat numbers, and hence by their total lengths. These sequences, with repeat numbers of 4, 7, and 11, are named Syn-n4, Syn-n7, and Syn-n11. Similar to native SRT proteins, these polypeptides comprise ordered crystalline and disordered amorphous domains, which contribute to their mechanical properties.

Figure 6:
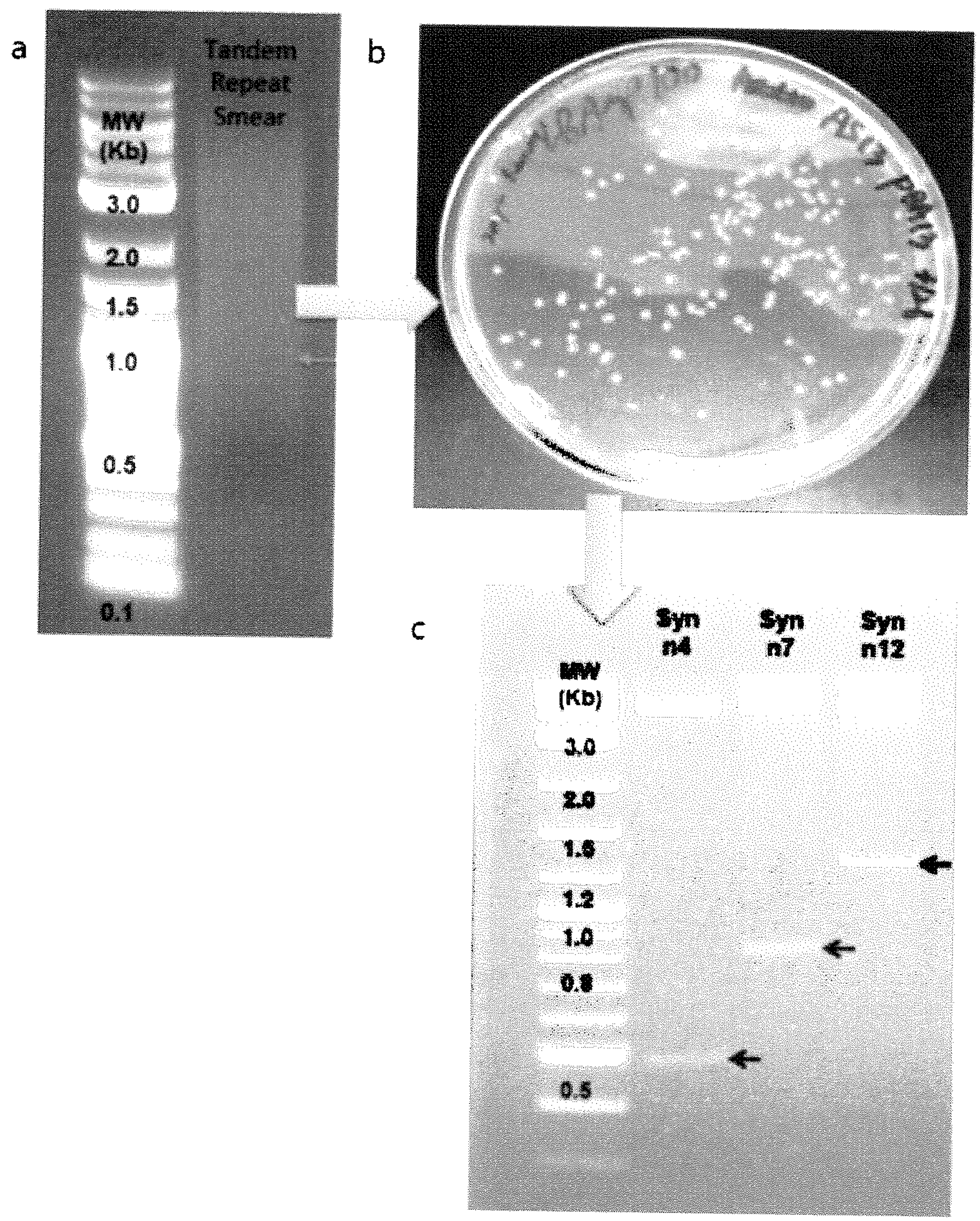
FIG. 6. (a). Synthetic polypeptides are obtained using the rolling circle amplification method, which created a smear band in the DNA gel. Once the sequence of interest is identified, the resulting gene sequence is then ligated into a cloning vector and recombinantly expressed in *E. Coli* (b). Examples of tandem repeat construction of n=4, 7 12 with DNA gels are shown in (c).

To construct this panel of TR sequences, we sought a convenient method to produce them simultaneously in a single cloning step (FIG. 4B). Rolling-circle amplification (RCA) generates high-molecular-weight TR products from short, circular DNA templates. We used a strategy similar to the incorporation of 5-methylcytosine (5 mC) to facilitate the partial digestion of PCR amplicons, to allow the partial digestion of RCA products, yielding TR sequences of various lengths that could be size-selected and cloned (FIG. 6). We reasoned that the ratio of 5 mC to cytosine in the RCA reaction would control the length distribution of the resulting partial digests. Additionally, the mechanism of RCA precludes the formation of mixed TR products when applied to a pool of template sequences, allowing the construction of pooled libraries, although we did not exploit that feature in this work. We analyzed cloned TR genes by diagnostic digestion and Sanger sequencing, and then expressed and purified in *E. coli* by standard methods.

Figure 5:
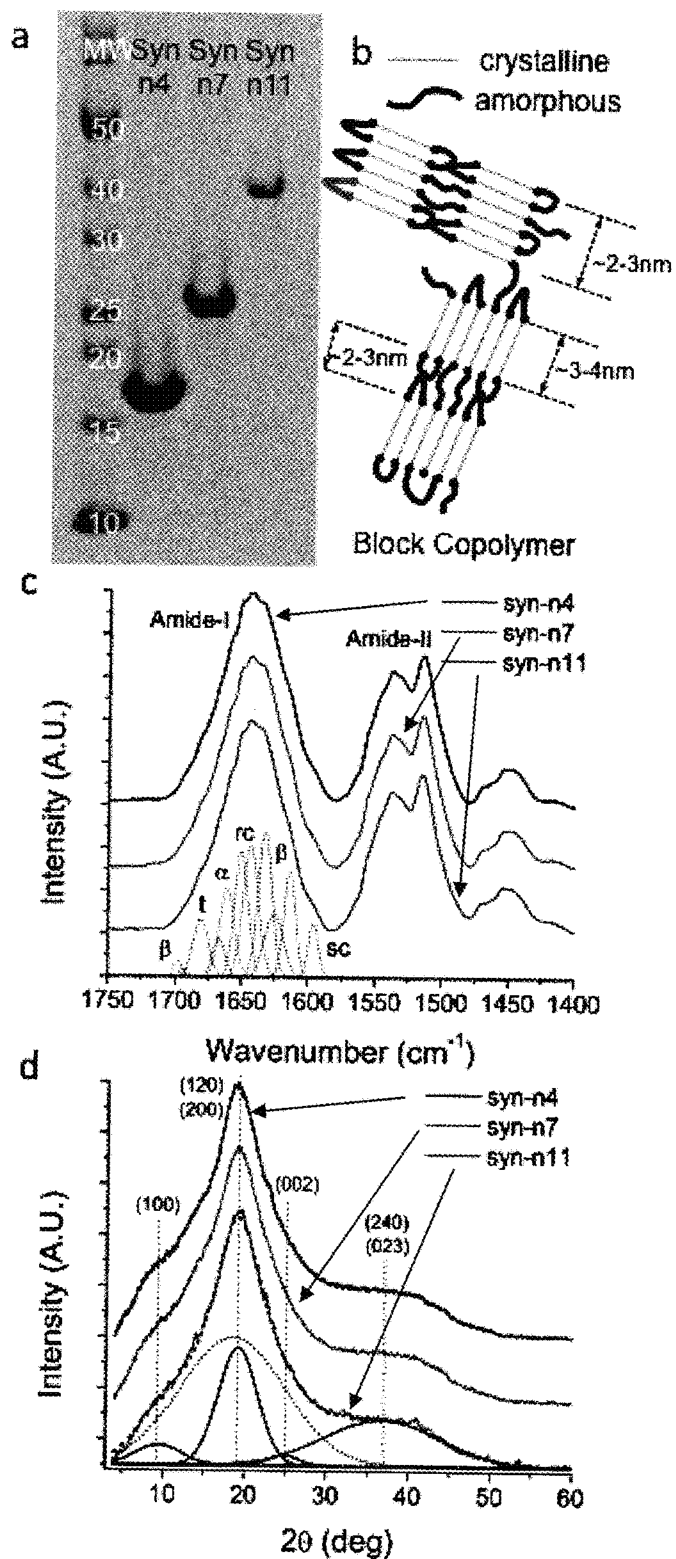
FIG. 5. (a) SDS-Page showing the sizes of the synthetic proteins with n=4, 7, 11. (b) Cartoon representation of the segmented polymer architecture of assembled polypeptides containing ordered β-sheet crystals and amorphous Gly-rich regions. Amorphous and crystalline are colored in green and red respectively. The FTIR (c) and XRD (d) spectra for all three samples are shown.

We utilized Fourier-transform infrared spectroscopy (FTIR), X-Ray Diffraction (XRD), and Dynamic Mechanical Analysis (DMA) to characterize the structures of the protein materials. Molecular sizes of synthetic sequences produced by our PD-RCA are listed in Table 1, and the corresponding protein SDS gels are shown in FIG. 5*a*. These three synthetic polypeptides have molecular weights varying between 15-40 kDa, similar to the polydispersed molecular weight distribution of native SRT complex (i.e., 15-55 kDa). The differences in chain length effect different mechanical responses as discussed below.

XRD and FTIR results revealed that these polypeptide chains contain ordered and amorphous domains. FIGS. 5*c* and 6 show the FTIR spectra for synthetic polypeptides. The amide I bands have been analyzed by using Fourier self-deconvolution and Gaussian fitting. FTIR peaks were assigned to secondary-structure elements. The relative areas of the single bands were used in the calculation of the fraction of the secondary structure features. A total of 11 bands were fitted to the deconvoluted spectra. The band centered at 1595 $cm^{-1}$ is assigned to the side chains of the protein (marked as sc). The absorption peak in this region is related to the aromatic ring in the side chains of tyrosine (Tyr) and histidine (His). Tyr and His are likely to contribute strongly to this band since their respective amino acid fractions are 15.3% and 4.9% for the synthetic polypeptides. A triplet of bands (marked as β) is fitted to the deconvoluted spectra between 1600 and 1637 $cm^{-1}$, which are assigned to β-sheets. Specifically, the band centered at 1613 $cm^{-1}$, 1626 $cm^{-1}$, and 1632 $cm^{-1}$ are assigned to intermolecular β-sheets formed by molecular aggregation, intermolecular β-sheets or stacking of antiparallel β-sheets in crystallized proteins, and the formation of intramolecular β-sheets respectively. A set of bands between the major β-sheet bands and the minor β-sheet band (1635-1700 $cm^{-1}$ range) are attributed to random coils, α-helices and turns secondary structures. The two bands centered at 1643 $cm^{-1}$ and 1650 $cm^{-1}$ are assigned to random coil conformations. The band centered at 1661 $cm^{-1}$ is assigned to α-helix secondary structures. These two secondary structural elements are attributed to the amorphous segments of the protein chains (Gly-rich) that connect the β-sheet crystals with each other. The three remaining bands centered at 1667, 1680 and 1693 $cm^{-1}$ are assigned to turn structures. The turn structure is attributed to the amorphous segments of the protein chains (Gly-rich) that allow the formation of intramolecular antiparallel β-sheets. Another small β-sheet band is observed at 1698 $cm^{-1}$, which is also observed in FTIR studies of silk fibroin. Although this band overlaps with the bands assigned to turn structures and is difficult to differentiate from them, it represents less than the 2% of the total amide I region. The fraction of secondary structure elements is determined by calculating the ratio of the fitted bands area to the total deconvoluted amide I band area. The secondary structure composition of synthetic polypeptides is summarized in Table 2.

Representative XRD spectra for three synthetic proteins are shown in FIG. 5*d*. The diffraction spectra for all three synthetic proteins are very similar. The crystallite size (i.e., 3.9×2.2 nm) is estimated from XRD according to Scherrer equation. The Miller indices are assigned consistently with the native SRT from a related species (*Dosidicus gigas*). The major crystalline peaks can be observed at 2Θ=9.50°, 19.15° and 24.85° corresponding to lattice distances $d_{100}$=9.31 Å, $d_{200}$=4.63 Å and $d_{002=3.58}$ Å (FIG. 3*e*). Additionally, a weak diffraction peak is observed at 2Θ=36.73° with lattice distance $d_{240}$=2.44 Å accompanied with a broad peak. The intense peak at 2Θ=19.15° is attributed to the combination of (120) and (200) reflections and the peak at 20=36.73° to the combination of (240) and (023) reflections. These lattice distances are 9.1 Å, 4.72 Å and 2×3.5 Å corresponding to the hydrogen-bond distance between two β-sheet chains, the distance between alternating β-sheet chains (i.e., unit cell dimension in the hydrogen-bond direction fitting two β-sheet chains) and the chain length of a single amino acid in an antiparallel β-sheet structure (with a two-residue repeat distance of 7.0 Å), respectively. According to the XRD results, β-sheet crystals can accommodate 11±2 amino acid residues along the backbone direction and 4.6±0.6 strands along the hydrogen bonding direction, which agrees well with the initial sequence design (i.e., 10 amino acid length between proline residues in crystalline segments). The β-sheet crystal structure is fitted into an orthorhombic unit cell referencing to other known β-sheet crystals such as silk. Although (0 k0) diffraction peaks cannot be resolved in the current diffraction pattern, the unit cell dimension b (amino acid side chain direction) is calculated from the $d_{120}$, $d_{240}$ and $d_{023}$ spacing values. The unit cell parameters obtained by the diffraction data are a=9.31 Å (H-bond direction), b=11.06 Å (amino acid side chain direction) and c=7.16 Å (chain backbone direction). The crystalline segments of synthetic polypeptides are rich in Ala, Thr, Val, Ser and His amino acids, which increase the complexity in the inter-sheet stacking (especially when incorporating large side groups such as His). We calculated the crystallinity percentage of the synthetic polypeptides by fitting the crystalline and amorphous peaks in the Lorentz-corrected WAXS intensity data. The crystallinity index is calculated as the ratio of the deconvoluted crystalline area to the total area. The crystallinity index of these proteins is in between 43-45% as listed in Table 3. This is slightly higher than the FTIR results due to increased noise inherent to WAXS analysis.

We studied the mechanical response of all three synthetic polypeptide using DMA. Syn-n4 is brittle, and shows linear elastic behavior at low strains and then fracture. In contrast both syn-n7 and syn-n11 can be deformed to larger strains compared to syn-n4, and they exhibit irreversible plastic deformation. The drawability of the syn-n11 was significantly larger than other two samples. Quantitative stress-strain analysis was carried out where the DMA analysis was repeated at least three times for each sample. Young modulus (~0.7-0.8 GPa) for the synthetic polypeptides was estimated from the linear region of the stress-strain curve. Compared to elastic modulus of recombinant 18 kDa SRT protein from *Loligo vulgaris* (~1-2 GPa) this value is slightly lower. The lower modulus could be due to ambient water in the sample (~5%) or trace amounts of HFIP retained from casting (<%1). Although the elastic modulus and the yield strength for three samples are similar (i.e., ~14 MPa for syn-n4 and syn-n7 and slightly higher value of 18 MPa for syn-n11), their toughness (i.e., 0.14, 0.46, and 2.37 $MJ/m^3$ respectively) and extensibility (i.e., 2, 4.5, and 15% respectively) increases as a function of polypeptide molecular weight.

Following the structure-property relationship for the yield stress of thermoplastics ($\sigma_y$=0.025·E), we estimate the yield strength of the synthetic proteins as 17.5 MPa, which agrees well with the experimental data of 14-18 MPa. The amorphous region of the synthetic protein has a loose network of chains that are tied together through secondary interactions (e.g., hydrogen bonds and van der Waals interactions). Therefore, we propose that the amorphous chains and reordering of β-sheets should dominate the fracture mechanism and the secondary bonds are broken upon tensile deformation. Deconvoluted FTIR spectrum shows that the crystallinity content of deformed syn-n11 samples doesn't change (Table 4), whereas individual β-sheet peaks vary (i.e., reorganization of crystalline domains), the turn content increases and α-helix content decreases. This agrees well with the observed macroscopic tensile behavior of an initial linear elastic regime followed by a large plateau regime at which the secondary bonds break.

We designed and characterized a new polypeptide sequence based on the native amino-acid content of semi-crystalline SRT proteins, and then generated tandem repeats of this sequence with a range of chain lengths using our PD-RCA approach. We demonstrate that toughness and extensibility of the synthetic polypeptides increase as a function of their molecular weights whereas the elastic modulus and yield strength remain unchanged.

From the description and data provided herein, polypeptides of varying size and composition of crystalline repeats can be produced. Such proteins can have considerable diversity (variable AVSTH-rich) in their crystal-forming sequences. Designing novel synthetic polypeptides with diverse semi-crystalline structure will help to elucidate repetition and composition rules for structural proteins. Similar to their natural and recombinant counterparts, synthetic SRT-mimics such as those described here can be processed to form any of a variety of three-dimensional shapes, including but not necessarily limited to ribbons, lithographic patterns, and nano-scale objects such as nanotube arrays. The ability to easily manufacture protein-based materials with tunable self-healing properties will find applications in a broad array of useful applications including textiles, cosmetics, and medicine.

An exemplary peptide sequence below is given to illustrate variations that can be made, for example, in crystalline domains. In particular, the following polypeptide (SynE3) was used as a basis for introducing variations in the crystalline region shown in italics: MTYGYGGLYGGLYGGLGYPAAASVSTVHHPYGYGGLYGGLYGGLGYPA AASVSTVHHPYGYGGLYGGLYGGLGYPAAASVST-VHHPYGYGGLYGGLYGGLGYPAAAS VSTVHHPY-GYGGLYGGLYGGLGYPAAASVSTVHHPYGYGGLYG-GLYGGLGYPAAASVST VHHPYGYGGLYGGLYGGLGYPAAASVSTVHHPS (SEQ ID NO:299). We determined variations can be introduced in at least positions S23, V24, S25, T26 (where the numbering begins counting the first N-terminal Gas amino acid number 1). Combinations of these variations were identified such that over 150 distinct polypeptide sequences were generated. The variations changed the SynE3 amino acid to a Pro, Leu or Ala. We also produced sequences containing insertions and deletions.

Sequences of an additional three exemplary polypeptides are provided below. Underlined amino acids denote amorphous region; Italicized amino acids denote crystalline region and lower case amino acids denote cloning region. The polypeptides are labeled as syn-n4 containing 4 repeats, syn-n7 containing 7 repeats and syn-n11 containing 11 repeats.

Syn-n4 (15 kDa)

(SEQ ID NO: 300)

MgtlsYGYGGLYGGLYGGLGYGPAAASVSTVHHPstgtlsYGYGG
LYGGLYGGLGYGPAAASVSTVHHPstgtlsYGYGGLYGGLYGGLG
YGPAAASVSTVHHPstgtlsYGYGGLYGGLYGGLGYGPAAASVST
VHHPstgtlsYGYGGLYGGLYGGLGYGP Syn-n7 (25 kDa)

(SEQ ID NO: 301)

MgtlsYGYGGLYGGLYGGLGYGPAAASVSTVHHPstgtlsYGYGG
LYGGLYGGLGYGPAAASVSTVHHPstgtlsYGYGGLYGGLYGGLG
YGPAAASVSTVHHPstgtlsYGYGGLYGGLYGGLGYGPAAASVST
VHHPstgtlsYGYGGLYGGLYGGLGYGPAAASVSTVHHPstgtls
YGYGGLYGGLYGGLGYGPAAASVSTVHHPstgtlsYGYGGLYGGL
YGGLGYGPAAASVSTVHHPstgtlsYGYGGLYGGLYGGLGYGP Syn-n11 (42 kDa)

-continued (SEQ ID NO: 302)

MgtlsYGYGGLYGGLYGGLGYGPAAASVSTVHHPstgtlsYGYGG
LYGGLYGGLGYGPAAASVSTVHHPstgtlsYGYGGLYGGLYGGLG
YGPAAASVSTVHHPstgtlsYGYGGLYGGLYGGLGYGPAAASVST
VHHPstgtlsYGYGGLYGGLYGGLGYGPAAASVSTVHHPstgtls
YGYGGLYGGLYGGLGYGPAAASVSTVHHPstgtlsYGYGGLYGGL
YGGLGYGPAAASVSTVHHPstgtlsYGYGGLYGGLYGGLGYGPAA
ASVSTVHHPstgtlsYGYGGLYGGLYGGLGYGPAAASVSTVHHPs
tgtlsYGYGGLYGGLYGGLGYGPAAASVSTVHHPstgtlsYGYGG
LYGGLYGGLGYGPAAASVSTVHHPstgtlsYGYGGLYGGLYGGLG
YGPAAASVSTVHHPstgtlsYGYGGLYGGLYGGLGYGP Materials and Methods Construction of a Tandem-Repeat Template:

A 111-bp gene fragment (FIG. 2A) encoding an 18-amino-acid amorphous region and an 11-amino-acid crystalline region was synthesized by Genewiz, cloned into plasmid pCR-Blunt by standard methods, and verified by Sanger sequencing. The insert contains five restriction sites to enable the PD-RCA process described below: two ScaI sites, to allow the insert to be removed from its vector by digestion; a BbvCI site, to allow a phi29-polymerase priming site to be generated by the nicking enzyme nt.BbvCI; and, an Acc65I and an ApaI site, which can each be blocked through the incorporation of 5-methylcytosine in place of cytosine. A circular, nicked version of the insert sequence was prepared as a template for rolling circle amplification (RCA), as follows. The plasmid was digested with ScaI-HF and the resulting 105-bp fragment was isolated on a 1% agarose-TAE gel and purified with an Omega Bio-Tek E.Z.N.A gel extraction kit. The purified 105-bp fragment was then circularized with T4 ligase at room temperature, followed by 10 minutes at 65° C. to inactivate the ligase. 1 μL of the heat-inactivated ligation reaction was then nicked using nt.BbvCI to create a priming site for RCA. The nicking enzyme reaction was heat-inactivated for 20 minutes at 80° C.

Rolling-Circle Amplification:

1.5 μL of the heat-inactivated nicking reaction was used as the template in a 10-μL rolling-circle amplification reaction with 1×NEB phi29 polymerase buffer, 1 μg BSA, 1 mM dATP, 1 mM dGTP, 1 mM dTTP, 0.5 mM dCTP, 0.5 mM 5-methyl-dCTP, and 2.5 units NEB phi29 polymerase. The reaction was incubated at 30° C. for 24 hours, and then heat-inactivated for 10 minutes at 65° C.

Figure 2:
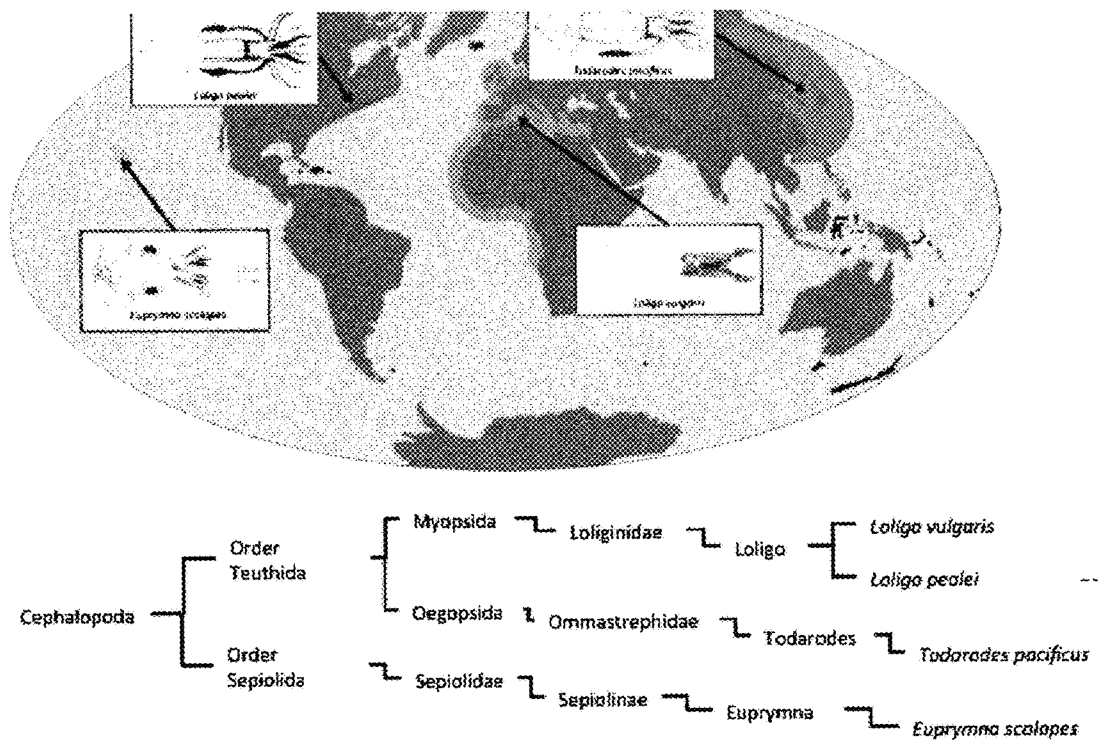
FIG. 2: Fishery information for four squid species, and corresponding protein gels, genetic relationship and optical images of squid ring teeth (SRT) are shown.
Figure 2:
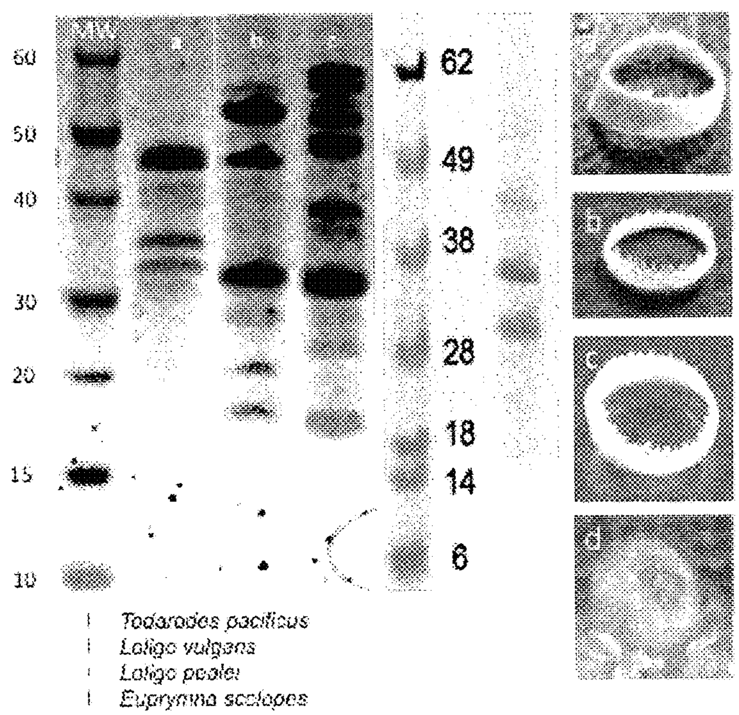

Sizing and Cloning of Tandem-Repeat Products:

The heat-inactivated RCA reaction was sequentially digested with ApaI and Acc65I, yielding tandem repeats of various sizes due to the random protection of their recognition sites by 5-methylcytosine (FIG. 2B). Tandem-repeat fragments between 500 bp and 1500 bp were isolated from a 1% agarose-TAE gel and purified with an Omega Bio-Tek E.Z.N.A gel extraction kit. The purified fragments were cloned via the Acc65I and ApaI sites into the open-reading frame of an expression vector prepared by site-directed mutagenesis of pET14b. Colony PCR was used to screen for clones with inserts of the desired sizes; diagnostic digestion and Sanger sequencing confirmed the lengths and compositions of the clones after plasmid isolation.

Protein Expression of TR-Syn:

A single colony was inoculated and grown overnight in 5 mL of LB with ampicillin (100 μg/mL). The overnight culture were scaled up to 2 L (i.e., four 500 mL LB media) and was grown on a shaker at 210 rpm and 37° C. for 5 hours. When the cultures reached OD600 of 0.7-0.9, IPTG was added to the final concentration of 1 mM and shaking was continued at 37° C. for 4 hours. Then, the cells were pelleted at 12,000 rpm for 15 minutes and stored at −80° C. After thawing, cell pellets were resuspended in 300 mL of lysis buffer (50 mM Tris pH 7.4, 200 mM NaCl, 1 mM PMSF, and 2 mM EDTA), and lysed using a high-pressure homogenizer. The lysate was pelleted at 14,000 rpm for 1 hour at 4° C. The lysed pellet was washed twice with 100 mL of urea extraction buffer (100 mM Tris pH 7.4, 5 mM EDTA, 2 M Urea, 2% (v/v) Triton X-100), and then washed with 100 mL of washing buffer (100 mM Tris pH 7.4, 5 mM EDTA). Protein collection in washing step (urea extraction and final wash) was performed by centrifugation at 5000 rpm for 15 minutes. The resulting recombinant-protein pellet was dried with a lyophilizer (Labconco, FreeZone 6 plus) for 12 hours. The final yield of expressed protein was approximately 15 mg per liter of bacterial culture.

Protein Gel Preparation:

0.2 mg of SRT is dissolved in 1 mL of 5% acetic acid/2 M urea solution, and subjected to sodium dodecyl sulfate polyacrylamide gel electrophoresis (SDS-PAGE) for protein separation. In each lane 10-30 μg of synthetic proteins were used together with SDS gel loading buffer that have either 6.7 M urea without acetic acid or 3.4 M urea with 2% acetic acid final concentration. The protein gels were stained with Coomassie blue dye.

Sample Preparation:

Syn-n4, Syn-n7, or Syn-n11 protein was dissolved in 1,1,1,3,3,3-Hexafluoro-2-propanol (HFIP) to a concentration of 50 mg/mL in a sonication bath for 1 hour. The solution was then cast into polydimethylsiloxane (PDMS) dog-bone shaped molds to produce the desired geometry for mechanical testing and solvent was evaporated at room temperature under a fume hood overnight. Resulting films were 50 μm in thickness, 2 mm in width and approximately 15 mm in length.

XRD:

X-Ray Diffraction (Wide Angle X-ray Scattering, WAXS) data was collected in a Rigaku DMAX-Rapid II Microdiffractometer (wavelength λ=0.154 nm) using a Cu Kα source and a 30 μm collimator with 10 minute exposure at 50 kV and 40 mA. The scattering angle 2Θ was collected from 3° to 75°. 2D WAXS diffraction patterns were converted to a one-dimensional pattern by integration across all azimuthal angles (avoiding the beam stop). The crystallinity index is calculated as the ratio of the area of crystal peaks to the total area by fitting the Lorentz-corrected WAXS intensity data using Gaussian functions. The data is analyzed with MDI Jade X-ray diffraction software and peak fitting was performed in OriginPro 8.5 software.

ATR-FTIR (attenuated total reflectance Fourier transform infrared spectroscopy): Spectral data were collected (Thermo Scientific Nicolet 6700 FT-IR) under attenuated total reflection (diamond crystal) mode using Happ-Genzel apodization with 4 $cm^{-1}$ resolution from 400 to 4000 $cm^{-1}$. For each spectrum, 256 scans were co-added. Fourier self-deconvolution (FSD) and second derivative evaluation of the amide I band (1580-1706 cm') were performed using the OMNIC software (Thermo Scientific, v7.3). Second derivatives were obtained from the original amide I spectra and a nine-point Savitsky-Golay smoothing filer of polynomial degree 5 was applied. FSD was performed with Lorentzian line shape with 25 $cm^{-1}$ bandwidth and an enhancement factor of 2. Curve fitting was performed. Individual bands were fitted to the deconvoluted spectra and were assigned to secondary structural components. The number and position of the fitted bands were obtained from the second derivative spectra, where the minima in the second derivative spectra corresponded to the fitted band maxima in the deconvoluted spectra. Gaussian curve fitting was performed in OriginPro 8.5 software by using a nonlinear least-squares method. First, the initial band positions (taken from the second derivatives) were fixed and the width and height were left as free parameters. Then, the band positions were allowed to change within a ±1 $cm^{-1}$ range using the built-in Levenberg-Marquardt algorithm. The relative areas of the single bands were used in the secondary-structure composition calculations.

Mechanical Testing:

Mechanical analysis was performed with a TA 800Q DMA instrument with film-tension clamps. Stress-strain curves were obtained at a constant strain rate of 1% per minute and a preload of 0.01 N.

RNA Isolation Protocol:

Suction cups were defrosted and RNALater solution was decanted. Any remaining SRT in the suction cups was removed to reduce protein contamination. The tissues samples were homogenized by slicing them into smaller pieces with a clean razor inside a biological hood and resuspended in RNAlater solution. The homogenized tissue was disrupted by adding 600 μL of RLT Plus lysis buffer (Qiagen), and kept in room temperature for 2 min (or until the solution color turned yellow) in eppendorf tubes. The solution was centrifuged for 3 min at high speed. For the DNA elimination, the lysate supernatant from last step was transferred to a DNA Eliminator spin column (Qiagen, RNAeasy Mini Kit), and centrifuged for 30 s at 10 000 rpm. 600 μL of 70% ethanol solution was added to the flow through and mixed well by pipetting without centrifugation. For RNA filtering, the solution was transferred to a RNAeasy spin column (Qiagen, RNAeasy Mini Kit) and centrifuged for 15 s at 1000 rpm. Three wash buffer steps were performed according to the Mini Kit user manual. Finally, RNA extraction was completed by adding 50 μL of RNase-free water directly to the spin column membrane, and by collecting the solution via centrifugation for 1 minute at 10 000 rpm. The solution was stored in the fridge for sequencing.

Dataset:

Details of the mRNA separation and conversion to cDNA can be found in our earlier publication (Pena-Francesch A, et al. (2014) Materials Fabrication from Native and Recombinant Thermoplastic Squid Proteins. *Advanced Functional Materials* 24(47):7401-7409) The isolated RNA was sequenced on an Illumina Hiseq instrument. European common squid (*Loligo vulgaris*) dataset contained 10, 160, 143 paired-end reads of 250 bp. *Loligo pealei, Todarodes pacificus*, and *Euprymna scolopes* datasets contained on average 12 million (i.e., 19207485, 10035062, 7652668 respectively) paired-end reads of 150 bp.

Bioinformatics Analyses: We used Trimmomatic (Bolger A M, Lohse M, & Usadel B (2014) Trimmomatic: a flexible trimmer for Illumina sequence data. *Bioinformatics: btu*170) for the quality control. Adaptor sequences and polyAs were removed from reads. Sliding-window trimming was performed, cutting once the average quality within a window size of 4 base pairs falls below 25. Very short reads of <36 base pairs were removed.

Transcript Assembly:

The quality controlled data sets were assembled using Trinity (Grabherr M G, et al. (2011) Full-length transcriptome assembly from RNA-Seq data without a reference genome. *Nature biotechnology* 29(7):644-652) with strand specific RNA sequencing library specification. Trinity assembly produced 33180, 42937, 48555, and 63562 transcripts from *Loligo vulgaris, Loligo pealei, Todarodes pacificus*, and *Euprymna scolopes* datasets respectively.

Blast Search and Short Read Mapping:

ORFs were extracted from trinity-assembled transcripts using transdecoder. Peptide sequences from the protein of interest were sequenced using mass-spectrometry (LC-MS/MS). From this, peptides with a confidence score of >50 were searched against transdecoder identified ORFs using tblastn. The blast hits that had alignments with >90% of the length of the peptide and with >=80% sequence identity were identified as the best hits. These best-hit transcripts were again searched for beta sheets (e.g, ASHVT-rich) using tblastn. The identified transcripts that had both peptide and beta-sheet sequence matches were extracted. From this set, we have chosen as candidate transcripts the sequences that have high glycine content and have polypeptide pattern P?*P (eg: PAAASVSTVHHP) in the length range of 7 to 26. However, since most of the assembled transcripts were not long enough to contain the complete coding sequences, further steps were necessary to identify and refine these. Our iterative process consisted of aligning the reads to each of the candidate transcripts using bwa-mem algorithm then extending the transcript according to the consensus sequences of the nucleotides extending past the end of the alignment. The resulting extended alignment was then again used as candidate in an identical subsequent step. This process of alignment, consensus call and extension was repeated until a stop codon was encountered that indicated that coding sequence of the transcript has been terminated. The process can be thought of as a supervised assembly method were we relied on automated processes to produce candidate extensions but have had to resort to manually curating the results. The manual curation was necessary because the automated transcript assemblies were not sufficiently sensitive and required fine tuning the results. The resulting candidate transcripts were aligned using Clustalw.

TABLE 1

Synthetically produced polypeptides and corresponding sizes based on mass spectroscopy analysis

| Sample | Designed Tandem Repeat (n) | Mass Spec Protein Size (kDa) |
|---|---|---|
| Syn-n4 | 4 | 15.6 |
| Syn-n7 | 7 | 25.7 |
| Syn-n11 | 11 | 40.5 |

TABLE 2

FTIR analysis of synthetic polypeptides

| | Syn-n4 | Syn-n7 | Syn-n11 |
|---|---|---|---|
| β-sheet | 41.6 ± 0.1% | 40.7 ± 1.3% | 41.8 ± 1.2% |
| Random Coil | 31.5 ± 1.2% | 33.1 ± 3.1% | 32.1 ± 3.3% |
| α-helix | 11.8 ± 0.6% | 11.7 ± 1.7% | 11.5 ± 0.4% |
| turns | 15.1 ± 0.5% | 14.6 ± 0.1% | 14.5 ± 2.5% |

TABLE 3

Percent of crystallinity of synthetic polypeptides from XRD analysis and their comparison to FTIR.

| Sample | C.I. (XRD) | C.I. (FTIR) |
|---|---|---|
| Syn-n4 | 45% | 41.6 ± 0.1% |
| Syn-n7 | 43% | 40.7 ± 1.3% |
| Syn-n11 | 45% | 41.8 ± 1.2% |

TABLE 4

FTIR analysis of Amide-I band for pristine and stretched syn-n11 samples.

| Syn-n11 | Pristine | Stretched |
|---|---|---|
| β-sheet | 41.8 ± 1.2% | 43.0 ± 2.1% |
| random coil | 32.1 ± 3.3% | 30.6 ± 1.1% |
| α-helix | 11.5 ± 0.4% | 6.4 ± 0.5% |
| turns | 14.5 ± 2.5% | 19.9 ± 0.7% |

TABLE 5

YYRKSVSTVSHGAHY (SEQ ID NO: 1)

VSSSVSHVSHGAHY (SEQ ID NO: 2)

AATAVSHTTHGIHH (SEQ ID NO: 3)

AATTAVTHH (SEQ ID NO: 4)

HVGTSVHSVSHGA (SEQ ID NO: 5)

HVGTSVHSVSHGV (SEQ ID NO: 6)

VTSAVHTVS (SEQ ID NO: 7)

AATTAVTQTHH (SEQ ID NO: 8)

AATTAVTHH (SEQ ID NO: 9)

AATAVSHTTHHA (SEQ ID NO: 10)

AVSTVSHGLGYGLHH (SEQ ID NO: 11)

RSVSHTTHSA (SEQ ID NO: 12)

YYRRSFSTVSHGAHY (SEQ ID NO: 13)

VSSVRTVSHGLHH (SEQ ID NO: 14)

AATAVSHTTHH (SEQ ID NO: 15)

VGAAVSTVHH (SEQ ID NO: 16)

AATAVSHNSS (SEQ ID NO: 17)

YIGRSVSTVSHGSHY (SEQ ID NO: 18)

MSSSVSHVSHTAHS (SEQ ID NO: 19)

VVSHVTHTI (SEQ ID NO: 20)

VGASVSTVSHGIGH (SEQ ID NO: 21)

VGQSVSTVSHGVHA (SEQ ID NO: 22)

TGSSISTVSHGV (SEQ ID NO: 23)

VGAAVSTVHH (SEQ ID NO: 24)

AATAVSHTTHH (SEQ ID NO: 25)

GAAAYSHTVHH (SEQ ID NO: 26)

TABLE 5-continued

| |
|---|
| AATTYRQTTHH (SEQ ID NO: 27) |
| AATAVSHTTHHA (SEQ ID NO: 28) |
| AAASVSTVHH (SEQ ID NO: 29) |
| AATAVSHTTHHA (SEQ ID NO: 30) |
| AVSTVSHGLGYGLHH (SEQ ID NO: 31) |
| ATAVSHTTHHA (SEQ ID NO: 32) |
| YIGRSVSTVSHGSHY (SEQ ID NO: 33) |
| MSSSVSHVSHTAHS (SEQ ID NO: 34) |
| VVSHVTHTI (SEQ ID NO: 35) |
| TGASVNTVSHGISHA (SEQ ID NO: 36) |
| ASTSVSHTTHSV (SEQ ID NO: 37) |
| VGASVSTVSHGIGH (SEQ ID NO: 38) |
| HTVSHVSHG (SEQ ID NO: 39) |
| VAHHGTISRRYAI (SEQ ID NO: 40) |
| VTHYSHVSHDVHQ (SEQ ID NO: 41) |
| AVGHTTVTHAV (SEQ ID NO: 42) |
| AATSVKTVSHGFH (SEQ ID NO: 43) |
| VGSTISHTTHGVHH (SEQ ID NO: 44) |
| AATSVSHTTHGVHH (SEQ ID NO: 45) |
| AASSVTHTTHGVAH (SEQ ID NO: 46) |
| GLLGAAATTYKHTTHHA (SEQ ID NO: 47) |
| AATTYSHTAHHA (SEQ ID NO: 48) |
| AAASTVSTVHH (SEQ ID NO: 49) |
| AATYSHTTHHA (SEQ ID NO: 50) |
| AAASVSTAHH (SEQ ID NO: 51) |
| AATSYSHALHH (SEQ ID NO: 52) |
| GLLGAAATTYKHTTHHA (SEQ ID NO: 53) |
| AATTYSHTAHHA (SEQ ID NO: 54) |
| AAASTVSTVHH (SEQ ID NO: 55) |
| AATYSHTTHHA (SEQ ID NO: 56) |
| AAAASVSTVHH (SEQ ID NO: 57) |
| AATSFSHTAHHA (SEQ ID NO: 58) |
| AAASTVSTVHH (SEQ ID NO: 59) |
| AATYSHTTHHA (SEQ ID NO: 60) |
| SVATRRVVY (SEQ ID NO: 61) |
| AVSHVTHTI (SEQ ID NO: 62) |
| AATSVSHTTHSV (SEQ ID NO: 63) |
| VGASVSTVSHGVHA (SEQ ID NO: 64) |
| VIHGGATLSTVSHGV (SEQ ID NO: 65) |
| TGTSVSTVSHGV (SEQ ID NO: 66) |

TABLE 5-continued

| |
|---|
| HSVSTVSHGA (SEQ ID NO: 67) |
| AGSSISTVSHGVHA (SEQ ID NO: 68) |
| TGSSISTVSHGVHS (SEQ ID NO: 69) |
| HIGTSVSSVSHGA (SEQ ID NO: 70) |
| HVGTSVHSVSHGV (SEQ ID NO: 71) |
| HASTTTHSIGL (SEQ ID NO: 72) |
| HSVSHVSHG (SEQ ID NO: 73) |
| VAHHGTISRRYAI (SEQ ID NO: 74) |
| HSVSHVSHG (SEQ ID NO: 75) |
| VAHHGTISRRYAI (SEQ ID NO: 76) |
| SHGVSHTAGYSSHY (SEQ ID NO: 77) |
| GHAVTHTVHH (SEQ ID NO: 78) |
| SAGGTTVSHSTHGV (SEQ ID NO: 79) |
| AVSHVTHTIHA (SEQ ID NO: 80) |
| HAVSTVAHGIH (SEQ ID NO: 81) |
| AATSVSHTTHSV (SEQ ID NO: 82) |
| AVRHTTVTHAV (SEQ ID NO: 83) |
| AATSVKTVSHGYH (SEQ ID NO: 84) |
| VGSTSVSHTTHGVHH (SEQ ID NO: 85) |
| AATTVSHTTHGAHH (SEQ ID NO: 86) |
| AASSVTHTTHGVAH (SEQ ID NO: 87) |
| SSYYGRSASTVSHGTHY (SEQ ID NO: 88) |
| TSVSQVSHTAHS (SEQ ID NO: 89) |
| VRYHGYSIGH (SEQ ID NO: 90) |
| AVSHVTHTIHA (SEQ ID NO: 91) |
| AATSVSHTTHSV (SEQ ID NO: 92) |
| VGASVSTVSHGVHA (SEQ ID NO: 93) |
| TGTSVSTVSHGV (SEQ ID NO: 94) |
| TGASVSTVSHGL (SEQ ID NO: 95) |
| AGSSISTVSHGVHA (SEQ ID NO: 96) |
| ATASVSHTTHGVHH (SEQ ID NO: 97) |
| AATTVSHSTHAV (SEQ ID NO: 98) |
| AATTVSHSTHAV (SEQ ID NO: 99) |
| GATTYSHTTHAV (SEQ ID NO: 100) |
| AVSHVTHTI (SEQ ID NO: 101) |
| AATSVSHTTHSV (SEQ ID NO: 102) |
| VIHGGATLSTVSHGV (SEQ ID NO: 103) |
| AGSSISTVSHGVHA (SEQ ID NO: 104) |
| GHAVTHTVHH (SEQ ID NO: 105) |
| SAGGTTVSHSTHGV (SEQ ID NO: 106) |

TABLE 5-continued

| |
|---|
| AVRHTTVTHAV (SEQ ID NO: 107) |
| AATSVKTVSHGYH (SEQ ID NO: 108) |
| VGSTSVSHTTHGVHH (SEQ ID NO: 109) |
| GAAFHY (SEQ ID NO: 110) |
| AATTVSHTTHGAHH (SEQ ID NO: 111) |
| AASSVTHTTHGVAH (SEQ ID NO: 112) |
| AAAVSHTTHHA (SEQ ID NO: 113) |
| AATAVSHTTHH (SEQ ID NO: 114) |
| VGAAVSTVHH (SEQ ID NO: 115) |
| VGGAVSTVHH (SEQ ID NO: 116) |
| GVAAYSHSVHH (SEQ ID NO: 117) |
| VSSVSTVSHGLHH (SEQ ID NO: 118) |
| VGAAVSTVHH (SEQ ID NO: 119) |
| VGGAVSTVHH (SEQ ID NO: 120) |
| GVAAYSHSVHH (SEQ ID NO: 121) |
| VASSVSHTTHGVHH (SEQ ID NO: 122) |
| AATTVSRTTHHA (SEQ ID NO: 123) |
| AATAVSHVTHHA (SEQ ID NO: 124) |
| AATSVSRTTHHA (SEQ ID NO: 125) |
| ATAAVSHTTHHA (SEQ ID NO: 126) |
| AATAVSHTTHHA (SEQ ID NO: 127) |
| AATAVSHTTHHA (SEQ ID NO: 128) |
| AATTVSRTTHHA (SEQ ID NO: 129) |
| AAAVSHVTHHA (SEQ ID NO: 130) |
| AATSVSHTTHHA (SEQ ID NO: 131) |
| AATAVSHTTHHA (SEQ ID NO: 132) |
| AATAVSHTTHHA (SEQ ID NO: 133) |
| AATSVSRTTHHA (SEQ ID NO: 134) |
| ATAAVSHTTHHA (SEQ ID NO: 135) |
| AATAVSHTTHHA (SEQ ID NO: 136) |
| AATAVSHVTHHA (SEQ ID NO: 137) |
| HTVSHVSHG (SEQ ID NO: 138) |
| VAHHSVVSRRYAI (SEQ ID NO: 139) |
| AATSVSHTTHHA (SEQ ID NO: 140) |
| AATAVSHTTHHA (SEQ ID NO: 141) |
| AATAVSHTTHHA (SEQ ID NO: 142) |
| AATAVSHTTHHA (SEQ ID NO: 143) |
| AAAVSHVTHHA (SEQ ID NO: 144) |
| AATAVHTTHHA (SEQ ID NO: 145) |
| VGAAVSHVTHHA (SEQ ID NO: 146) |
| VATSVSRTTHHA (SEQ ID NO: 147) |
| AATAVSHTTHHA (SEQ ID NO: 148) |
| SATAVSHTSH (SEQ ID NO: 149) |
| ASSAVSHTSHH (SEQ ID NO: 150) |
| VATVTSQTSHHV (SEQ ID NO: 151) |
| AASAVSTSTH (SEQ ID NO: 152) |
| VATSVSRTTHHA (SEQ ID NO: 153) |
| AATAVSHVTHHA (SEQ ID NO: 154) |
| VAHHSVVSRRYAI (SEQ ID NO: 155) |
| HAVGAVSTLHH (SEQ ID NO: 156) |
| HSVAVGVHH (SEQ ID NO: 157) |
| AATAVSHTTHHA (SEQ ID NO: 158) |
| AATAVSHVTHHA (SEQ ID NO: 159) |
| VAHHSVVSRRYAI (SEQ ID NO: 160) |

TABLE 6

| |
|---|
| GYGLGGLYGGYGLGGLHYGGYGLGGLHYGGYGLHY (SEQ ID NO: 161) |
| GVGGLYGGYGLGGLHGGYGLGGIYGGYGAHY (SEQ ID NO: 162) |
| GVGGYGMGGLYGGYGLGGVYGGYGLGG (SEQ ID NO: 163) |
| GYGLGVGL (SEQ ID NO: 164) |
| LGLGYGGYGLGLGYGLGHGYGLGLGAGI (SEQ ID NO: 165) |
| GLGLGYGYGLGHGLG (SEQ ID NO: 166) |
| GLGLGYGLGLGL (SEQ ID NO: 167) |
| MGGLYGGYGLGGVYGGYGLGGIYGGYGAHY (SEQ ID NO: 168) |
| GVGGLYGGYGLGGLYGGYGLGGLHGGYSLGGLYGGYGAHY (SEQ ID NO: 169) |
| GVGGLYGGYGLGGLHYGGYGLGGLHYGGYGLHY (SEQ ID NO: 170) |
| YGYGGLYGGLYGGLG (SEQ ID NO: 171) |
| YGYGGLYGGLYGGLG (SEQ ID NO: 172) |
| VAYGGWGYGLGGLHGGWGYGLGGLHGGWGYALGGLYGGLHY (SEQ ID NO: 173) |
| VGLGYGGLYGGLHY (SEQ ID NO: 174) |
| VGYGGFGLGFGGLYGGLHY (SEQ ID NO: 175) |
| SLGAYGGYGLGGLIGGHSVYH (SEQ ID NO: 176) |
| SLGAYGGYGLGGIVGGYGAYN (SEQ ID NO: 177) |
| VGYGGFGLGFGGLYGGLHY (SEQ ID NO: 178) |
| VGLGYGGFGLGYGGLYGGFGY (SEQ ID NO: 179) |
| VAYGGLGYGFGF (SEQ ID NO: 180) |
| GYGGLYGGLGYHY (SEQ ID NO: 181) |

TABLE 6-continued

YGYGGLYGGLYGGLGY (SEQ ID NO: 182)

VGYGGYGLGAYGAYGLGYGLHY (SEQ ID NO: 183)

YGYGGLYGGLYGGLG (SEQ ID NO: 184)

VGYAGYGLG (SEQ ID NO: 185)

YGGFGYGLY (SEQ ID NO: 186)

GYGGLYGHYGGYGLGGAYGH (SEQ ID NO: 187)

GIGGVYGHGIGGLGGVYGHGIGGVYGHGIGGLYGHGFGGAYGGYGGYGIGG (SEQ ID NO: 188)

VTYGGLGLGGLGYGGLGYGGLGYGGLGYGGLGYGGLGYGGLGYGGLGAGGLYG (SEQ ID NO: 189)

GAVGLGYGLGGGYGGLYGLHL (SEQ ID NO: 190)

ALGLGLYGGAHL (SEQ ID NO: 191)

GLGLNYGVYGLH (SEQ ID NO: 192)

GYGGWGYGLGGWGHGLGGLG (SEQ ID NO: 193)

YGGIGLGGLYGGYGAHF (SEQ ID NO: 194)

HSVGWGLGGWGGYGLGYGVHA (SEQ ID NO: 195)

ALGAYGGYGFGGIVGGHSVYH (SEQ ID NO: 196)

ALGGYGGYGLGGIVGG (SEQ ID NO: 197)

ALGAYGGYGLGGLVGGFGAYH (SEQ ID NO: 198)

VGFGGYGLGGYGLGGYGLGGYGLGGYGLGGLVGGYGSYH (SEQ ID NO: 199)

VGYGGYGLGGYGGYGLGGLTGGYGV (SEQ ID NO: 200)

GYGLGLGYGLGLGAG (SEQ ID NO: 201)

LGLGYGYGLGLGYGLGLGAGI (SEQ ID NO: 202)

HLGLGLGYGYGLGHGLG (SEQ ID NO: 203)

GLGLGYGLGLGYGYGV (SEQ ID NO: 204)

GYGLGLGLGGAGYGY (SEQ ID NO: 205)

VGGYGGFGLGGYGGYGLGG (SEQ ID NO: 206)

VGYGGLYGHYGGYGLGGVYGHGVGLGGVYGHGIGGAYGGYGLGVGGLYGGYGGYGIGG (SEQ ID NO: 207)

VGGYGGFGLGGYGGYGLGG (SEQ ID NO: 208)

VGYGGLYGHYGGYGLGGVYGHGVGLGGVYGHGVGLGGVYSH (SEQ ID NO: 209)

GIGGAYGGYGLGVGGLYGGYGGYGIGG (SEQ ID NO: 210)

VLSGGLGLSGLSGGYGTYR (SEQ ID NO: 211)

GYGGVGYGGLGYGGLGYGVGGLYGLQY (SEQ ID NO: 212)

GYGGWGYGLGGWGHGLGGLGSYGLHY (SEQ ID NO: 213)

HSVGWGLGGWGGYGLGYGVRS (SEQ ID NO: 214)

YGDVYGGLYGGLYGGLLGA (SEQ ID NO: 215)

VAYGGLGLGALGYGGLGYGGLGYGGLGAGGLYGLHY (SEQ ID NO: 216)

GYGLGLGLYGAHL (SEQ ID NO: 217)

AYGGWGYSLGRWGQGLGGLGTYGLHY (SEQ ID NO: 218)

HSVGWGLGGWGGYGLGYGVHA (SEQ ID NO: 219)

ALGGYGGYGLGGIVGGHSVYH (SEQ ID NO: 220)

ALGEYGGYGLGGIVGGH (SEQ ID NO: 221)

GFGGYGLGGYGLGGYGLGGYG (SEQ ID NO: 222)

IGFGGWGHGYGYSGLGFGGWGHGLGGWGHGYGY (SEQ ID NO: 223)

HAVGFGGWGHGIGLGHGFGY (SEQ ID NO: 224)

HAVGFGGWGHGFGY (SEQ ID NO: 225)

HSVSYGGWGFGHGGLYGLH (SEQ ID NO: 226)

HADYGVSGLGGYVSSY (SEQ ID NO: 227)

HSVGWGLGGWGGYGLGYGVHA (SEQ ID NO: 228)

ALGAYGGYGFGGIVGGHSVYH (SEQ ID NO: 229)

VGFGGYGLGGYGLGGYGLGGYGLGGYGLGGVVGGFGGYH (SEQ ID NO: 230)

FGYGGVGYGGLGYGGLGYGVGGLYGLQY (SEQ ID NO: 231)

VAYGGLGLGALGYGGLGYGGLGAGGLYGLHY (SEQ ID NO: 232)

AGLGYGLGGVYGGYGLHA (SEQ ID NO: 233)

YGYGGLYGGLGYHAGYGLGGYGLGYGLHY (SEQ ID NO: 234)

VGWGLGGLYGGLHH (SEQ ID NO: 235)

GYGGYGLGLGGLYGGLHY (SEQ ID NO: 236)

GYGGYGLGFGGLYGGFGY (SEQ ID NO: 237)

AYGYGYGLGGYGGYGLYGGYGLHH (SEQ ID NO: 238)

VAYGGWGYGLGGLHGGWGYGLGGLYGGLH (SEQ ID NO: 239)

GYGGYGLGLGGLYGGLHY (SEQ ID NO: 240)

VGYAGYGYGLGSYGGYAGLGLGLYGAGYHY (SEQ ID NO: 242)

YAYGGLYGGYGLGAYGY (SEQ ID NO: 243)

VGYAGYGYGLGAYGGYAGLGLGLYGAGYHY (SEQ ID NO: 244)

YAYGGLYGGYGLGAYGY (SEQ ID NO: 245)

VGYGGFGLAGYGYGY (SEQ ID NO: 246)

YGYGGLYGGYAGLGLGLYGAGYHY (SEQ ID NO: 247)

YAYGGLYGGYGLGAYGY (SEQ ID NO: 248)

VGYAGYGYGLGAYGGYAGLGLGLYGAGYHY (SEQ ID NO: 249)

YAYGGLYGGYGLGAYGY (SEQ ID NO: 250)

VGYAGYGLGLYGAGYHY (SEQ ID NO: 251)

YAYGGLYGGYGLGAYGY (SEQ ID NO: 252)

VGYAGYGLGAYGGYAGYGLGAFGGYAGYGLGAFGGYAGLGLGLYGAGYHY (SEQ ID NO: 253)

LGFGGLLGGYGGLHHGVYGLGGYGGLYGGYGLGGYGLHGLHY (SEQ ID NO: 254)

LGFGGVLGYGGLHHGVYGLGGYGGLHGAYGLGGYGGLHGAYGLGGY

TABLE 6-continued

GGLYGGYGLGGH (SEQ ID NO: 255)

VGYGGYGYGGLGAYGHYGGYGLGGLYGGYGLGGAYGGYGLGGGYGG YGVGVHSRYGVG (SEQ ID NO: 256)

GYGYGGLLGGYGLHY (SEQ ID NO: 257)

YGYGLAGYGGLYGGLHGAAYGLGGYGLHY (SEQ ID NO: 258)

LGYGLAGYGGLYGGLYGGHGLGGYGGVYGGYGLHGLHY (SEQ ID NO: 259)

LGFGGVLGYGGLHH (SEQ ID NO: 260)

GVYGLGHGAYGLGGYGGLHGAYGLGGYGGLYGGYGLGGYGALHGGL YGGYGLGGGLL (SEQ ID NO: 261)

YSYGGLVGGYGGLYHHA (SEQ ID NO: 262)

LFGGILGGYGGVLAGYGGLHHGAYGLGGYGGLYGGYGLGGYGLHGL HY (SEQ ID NO: 263)

LGFGGVLGYGGLHHGVYGLGGYGGLHGAYGLGGYGGLHGAYGLGGY GGLYGGTLSTL (SEQ ID NO: 264)

GYGYGGLLGGLGHAVG (SEQ ID NO: 265)

VGYGYGGLLGGYGGLYGGWGGVYGGLG (SEQ ID NO: 266)

VGYGYGGFLGGYGLGVYGHGY (SEQ ID NO: 267)

LGYGLAGYGGLYGGLYGGHGLGGYGGVYGGYGLHGLHY (SEQ ID NO: 268)

LGFGGVLGYGGLHHGVYGLGGYGGLHGAYGLGGYGGLHGAYGLGGY GGLYGGYGLGGYGALHGGLYGGYGLGGGL (SEQ ID NO: 269)

GYGYGGLLGGYGLHY (SEQ ID NO: 270)

YGYGLAGYGGLYGGYGLGGYGLGY (SEQ ID NO: 271)

LGYGLAGYGGLYGGLYGGHGLGGYGGVYGGYGLHGLHY (SEQ ID NO: 272)

LGFGGVLGYGGLHHGVYGLGGYGGLHGAYGLGGYGLGGFHGGYGLG G (SEQ ID NO: 273)

VGLGLGGFHGGYGFGGYGLGGFHGGYG (SEQ ID NO: 274)

VGFGGYGYGGIGGLYGGHYGGYGLGGAYGHYGGYGLGG (SEQ ID NO: 275)

GYGYGGLLGGLGHAVG (SEQ ID NO: 276)

GYGYGGLLGGYGGLYGGWGGVYGGLG (SEQ ID NO: 277)

TABLE 6-continued

VGYGYGGFLGGYGLGVYGHGY (SEQ ID NO: 278)

LGYGGLLGGYGGLYGGYGLGGYGLGY (SEQ ID NO: 279)

YGYGLAGYGGLYGGLLH (SEQ ID NO: 280)

LGYGLAGYGGLYGGLYGGHGLGGYGGVYGGYGLHGLHY (SEQ ID NO: 281)

LGFGGVLGYGGLHHGAYGLGGYGGLYGGYGLGGYGGLYGGYGALHG GYGLGY (SEQ ID NO: 282)

YGLAGYGGLYGGLLH (SEQ ID NO: 283)

TALGYGGLYGGYGLGAYGLGY (SEQ ID NO: 284)

LGYGGLLGGYGGLYGRYGVGGYGLGY (SEQ ID NO: 285)

GGYGSLLGGHGGLYGGLGL (SEQ ID NO: 286)

YGYGGVLGGYGQGL (SEQ ID NO: 287)

LGYGGLLGGYGGLHHGVYG (SEQ ID NO: 288)

GGYGGLYGGYGLGGYGGLHGAYGLGGYGGVYGGYGLGGH (SEQ ID NO: 289)

VGYGGYGYGGLGAYGHYGGYGLGGLYGGYG (SEQ ID NO: 290)

VGYGYGGLLGGYGGLYGGWGGVYGGLG (SEQ ID NO: 291)

VGYGYGGFLGGYGLGVYGHGY (SEQ ID NO: 292)

LGYGLAGYGGLYGGLYGGHGLGGYGGVYGGYGLHGLHY (SEQ ID NO: 293)

LGFGGVLGYGGLHHGVYGLGGYGGLHGAYGLGGYGGLYGGYGLGGH (SEQ ID NO: 294)

VYGGYGLGGH (SEQ ID NO: 295)

VGYGGYGYGGGLYGGHYGGYGHFGGVHSHYGVG (SEQ ID NO: 296)

YGDVYGGLYGGLYGGLLGA (SEQ ID NO: 297)

LGYGGLLGGYGALHGGLYGGYGLGGLHY (SEQ ID NO: 298)

While the invention has been described through specific embodiments, routine modifications will be apparent to those skilled in the art and such modifications are intended to be within the scope of the present invention.

What is claimed is:

1. A polypeptide comprising alternating repeats of crystallite-forming subsequences and amorphous subsequences, wherein the crystallite-forming subsequences form crystallites comprising stacks of one or more β-sheets, and wherein the amorphous subsequences form a network of hydrogen bonds, and wherein the sequence of the polypeptide has at least 80% sequence identity to SEQ ID NO: 300, SEQ ID NO: 301 or SEQ ID NO: 302.

2. The polypeptide of claim 1, wherein the polypeptide comprises from 4 to 20 repeats of the crystallite-forming subsequences.

3. The polypeptide of claim 1, wherein the crystallite-forming subsequence is from about 2 nm to about 5 nm long.

4. The polypeptide of claim 1, wherein the polypeptide sequence exhibits crystallinity between 0% and 60%.

5. The polypeptide of claim 1, wherein the amorphous subsequence comprises from 10 to 60 amino acids.

6. The polypeptide of claim 1, wherein the polypeptide exhibits self-healing behavior.

7. A composition comprising a plurality of the polypeptide of claim 1.

8. The composition of claim 7, wherein the plurality of the polypeptide comprises distinct polypeptides.

* * * * *